United States Patent [19]

Ok et al.

[11] Patent Number: 5,317,017
[45] Date of Patent: May 31, 1994

[54] N-BIPHENYL-3-AMIDO SUBSTITUTED BENZOLACTAMS STIMULATE GROWTH HORMONE RELEASE

[75] Inventors: Hyun O. Ok; William R. Schoen, both of Edison; Matthew Wyvratt, Mountainside, all of N.J.

[73] Assignee: Merck & Co., Inc., Rahway, N.J.

[21] Appl. No.: 954,220

[22] Filed: Sep. 30, 1992

[51] Int. Cl.$^5$ .................... A61K 31/55; C07D 243/10; C07D 267/02; C07D 281/02; C07D 401/02; C07D 413/02; C07D 417/02

[52] U.S. Cl. .................... 514/211; 514/213; 540/490; 540/491; 540/524; 540/527

[58] Field of Search .............. 540/524, 490, 491, 527; 514/211, 213

[56] References Cited

U.S. PATENT DOCUMENTS

| | | | |
|---|---|---|---|
| 3,239,345 | 2/1966 | Hodge et al. | 548/309.1 X |
| 4,036,979 | 7/1977 | Asato | 548/309.1 X |
| 4,411,890 | 10/1983 | Momany | 548/309.1 X |

FOREIGN PATENT DOCUMENTS

| | | | |
|---|---|---|---|
| 253310 | 1/1988 | European Pat. Off. | 548/309.1 |
| 291969 | 11/1988 | European Pat. Off. | 548/309.1 |
| 324377 | 7/1989 | European Pat. Off. | 548/309.1 |
| 166357 | 1/1990 | European Pat. Off. | 544/105 |
| 349949 | 10/1990 | European Pat. Off. | 540/240 |

OTHER PUBLICATIONS

Jones, et al J. Chem. Soc. c. pp. 2176–2181 (1969).
Davis, et al Arch. Biochem. Biophys 102 pp. 48–51.
Wattley, et al J. Med. Chem. 28 pp. 1511–1516 (1985).
Slade, et al J. Med. Chem. 28 pp. 1517–1521 (1985).
Huang, et al Synthesis, 10 p. 851 (1984).
Stewart, Australia J. Chem. 33 pp. 633–640 (1980).
Still, et al J. Org. Chem 43, p. 2923 (1978).
Parsons, W. H., Med. Chem. vol. 32, pp. 1681–1685.
J. Med. Chem., 35, 756, 733, 780 (1992) Lakanen et al, Floyd et al.
Aszmeimittel-Forsch 21, 1338 (1971) Sato et al.
Ott, Arch Pharm (Weinheim) 323, 601–603 (1990).

*Primary Examiner*—Floyd D. Higel
*Attorney, Agent, or Firm*—David L. Rose; Joseph F. DiPrima

[57] ABSTRACT

There are disclosed certain compounds identified as N-biphenyl-3-amido substituted benzolactams which promote the release of growth hormone in humans and animals. This property can be utilized to promote the growth of food animals to render the production of edible meat products more efficient, and in humans, to increase the stature of those afflicted with a lack of a normal secretion of natural growth hormone. Growth promoting compositions containing such benzolactams as the active ingredient thereof are also disclosed.

13 Claims, No Drawings

N-BIPHENYL-3-AMIDO SUBSTITUTED BENZOLACTAMS STIMULATE GROWTH HORMONE RELEASE

BACKGROUND OF THE INVENTION

Growth hormone, which is secreted from the pituitary, stimulates growth of all tissues of the body that are capable of growing. In addition, growth hormone is known to have the following basic effects on the metabolic process of the body:

1. Increased rate of protein synthesis in all cells of the body;
2. Decreased rate of carbohydrate utilization in cells of the body;
3. Increased mobilization of free fatty acids and use of fatty acids for energy.

A deficiency in growth hormone secretion can result in various medical disorders, such as dwarfism.

Various ways are known to release growth hormone. For example, chemicals such as arginine, L-3,4-dihydroxyphenylalanine (L-DOPA), glucagon, vasopressin, and insulin induced hypoglycemia, as well as activities such as sleep and exercise, indirectly cause growth hormone to be released from the pituitary by acting in some fashion on the hypothalamus perhaps either to decrease somatostatin secretion or to increase the secretion of the known secretagogue growth hormone releasing factor (GRF) or an unknown endogenous growth hormone-releasing hormone or all of these.

In cases where increased levels of growth hormone were desired, the problem was generally solved by providing exogenous growth hormone or by administering an agent which stimulated growth hormone production and/or release. In either case the peptidyl nature of the compound necessitated that it be administered by injection. Initially the source of growth hormone was the extraction of the pituitary glands of cadavers. This resulted in a very expensive product and carried with it the risk that a disease associated with the source of the pituitary gland could be transmitted to the recipient of the growth hormone. Recently, recombinant growth hormone has become available which, while no longer carrying any risk of disease transmission, is still a very expensive product which must be given by injection or by a nasal spray.

Other compounds have been developed which stimulate the release of endogenous growth hormone such as analogous peptidyl compounds related to GRF or the peptides of U.S. Pat. No. 4,411,890. These peptides, while considerably smaller than growth hormones are still susceptible to various proteases. As with most peptides, their potential for oral bioavailability is low. The instant compounds are non-peptidyl agents for promoting the release of growth hormone which may be administered parenterally, nasally or by the oral route.

SUMMARY OF THE INVENTION

The instant invention covers certain benzo-fused lactam compounds which have the ability to stimulate the release of natural or endogenous growth hormone. The compounds thus have the ability to be used to treat conditions which require the stimulation of growth hormone production or secretion such as in humans with a deficiency of natural growth hormone or in animals used for food production where the stimulation of growth hormone will result in a larger, more productive animal. Thus, it is an object of the instant invention to describe the benzo-fused lactam compounds. It is a further object of this invention to describe procedures for the preparation of such compounds. A still further object is to describe the use of such compounds to increase the secretion of growth hormone in humans and animals. A still further object of this invention is to describe compositions containing the benzo-fused lactam compounds for the use of treating humans and animals so as to increase the level of growth hormone secretions. Further objects will become apparent from a reading of the following description.

DESCRIPTION OF THE INVENTION

The novel benzo-fused lactams of the instant invention are best described in the following structural formula I:

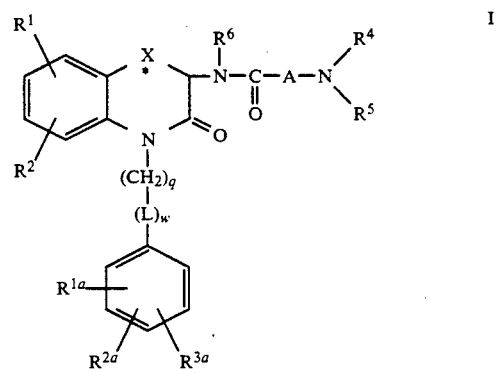

where
L is

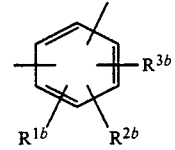

q is 0 to 4;
w is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, $R^{7b}$O(CH$_2$)$_v$—, $R^{7b}$COO(CH$_2$)$_v$—, $R^{7b}$OCO(CH$_2$)$_v$—, $R^4R^5$N(CH$_2$)$_v$—, $R^{7b}$CON(R$^4$)(CH$_2$)$_v$—, $R^4R^5$NCO(CH$_2$)$_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3; $R^{3a}$ and $R^{3b}$ are independently hydrogen, $R^9$, $C_1$-$C_6$ alkyl substituted with $R^9$, phenyl substituted with $R^9$, or phenoxy substituted with $R^9$;
m is 0 to 2;
$R^9$ is:

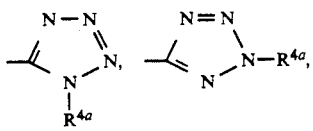 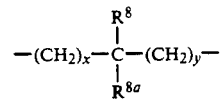

$R^{7b}O(CH_2)_v$—, $R^{7b}COO(CH_2)_v$—, $R^{7b}OCO(CH_2)_v$—, $R^{7b}CO(CH_2)_v$—, $R^{7b}O(CH_2)_vCO$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^4R^5NN(R^5)CS(CH_2)_v$—, $R^{7b}CON(R^4)N(R^5)CO(CH_2)_v$—, $R^{7b}CON(R^4)N(R^5)CS(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CSN(R^{12c})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$, or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3 and $R^1$ and $R^{10}$ are as defined;

$R^{13}$ is $C_1$-$C_3$ perfluoroalkyl, $C_1$-$C_6$ alkyl, substituted $C_1$-$C_6$ alkyl, where the substitutents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl- $C_1$-$C_6$ alkyl;

X is —$CH_2CH(R^{20})$—, —$CH(R^{21})CH_2$—, —$CH(R^{21})CH(R^{20})$—, —$CH=C(R^{20})$—, —$C(R^{21})=CH$—, —$C(R^{21})=C(R^{20})$—, —$S(O)_mCH(R^{20})$— or —$OCH(R^{20})$—; $R^{20}$ and $R^{21}$ are independently hydrogen, $R^1$, $R^2$ independently disubstituted phenyl, $R^1$, $R^2$ independently disubstituted thiophenyl, $C_1$-$C_{10}$ alkyl, substituted $C_1$-$C_{10}$ alkyl, $C_2$-$C_{10}$ alkenyl, substituted $C_2$-$C_{10}$ alkenyl, $C_2$-$C_{10}$ alkynyl, substituted $C_2$-$C_{10}$ alkynyl where the substituents on the alkyl, alkenyl and alkynyl are from 1 to 3 of hydroxy, $C_1$-$C_6$ alkoxy, fluoro, $R^1$ substituted phenyl, —$NR^{10}R^{11}$, carboxy, $C_1$-$C_5$ alkoxycarbonyl or formyl where $R^1$, $R^{10}$, $R^{11}$ and m are as defined above; or $R^{20}$ and $R^{21}$ can be taken together to form —$(CH_2)_rB(CH_2)_s$— where B, r and s are as defined above, with the proviso that $R^{20}$ and $R^{21}$ cannot both be hydrogen;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, $C_3$-$C_{10}$ alkenyl, substituted $C_3$-$C_{10}$ alkenyl, $C_3$-$C_{10}$ alkynyl, or substituted $C_3$-$C_{10}$ alkynyl where the substituents on the phenyl, alkyl, alkenyl or alkynyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$ alkanoyloxy, $C_1$-$C_5$ alkoxycarbonyl, carboxy, formyl, or —$NR^{10}R^{11}$; or $R^4$ and $R^5$ can be taken together to form —$(CH_2)_rB(CH_2)_s$— where B, r, s, $R^1$, $R^2$, $R^{10}$ and $R^{11}$ are as defined above;

$R^6$ is hydrogen, $C_1$-$C_{10}$ alkyl, phenyl or phenyl $C_1$-$C_{10}$ alkyl;

A is where x and y are independently 0–3;

$R^8$ and $R^{8a}$ are independently hydrogen, $C_1$-$C_{10}$ alkyl, trifluoromethyl, phenyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $C_3$-$C_7$ cycloalkyl, $R^1$, $R^2$ independently disubstituted phenyl $C_1$-$C_3$ alkoxy, $R^1$, $R^2$ independently disubstituted phenyl, $C_1$-$C_5$-alkanoyloxy, $C_1$-$C_5$ alkoxycarbonyl, carboxy, formyl, or —$NR^{10}R^{11}$ where $R^1$, $R^2$, $R^{10}$ and $R^{11}$ are as defined above; or $R^8$ and $R^{8a}$ can be taken together to form —$(CH_2)_t$— where t is 2 to 6; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

In the above structural formula and throughout the instant specification, the following terms have the indicated meanings:

The alkyl groups specified above are intended to include those alkyl groups of the designated length in either a straight or branched configuration. Exemplary of such alkyl groups are methyl, ethyl, propyl, isopropyl, butyl, sec-butyl, tertiary butyl, pentyl, isopentyl, hexyl, isohexyl, and the like.

The alkoxy groups specified above are intended to include those alkoxy groups of the designated length in either a straight or branched configuration. Exemplary of such alkoxy groups are methoxy, ethoxy, propoxy, isopropoxy, butoxy, isobutoxy, tertiary butoxy, pentoxy, isopentoxy, hexoxy, isohexoxy and the like.

The term "halogen" is intended to include the halogen atom fluorine, chlorine, bromine and iodine.

Certain of the above defined terms may occur more than once in the above formula and upon such occurrence each term shall be defined independently of the other.

Preferred compounds of the instant invention are realized when in the above structural formula:

q is 0 to 2;

w is 0 or 1;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

m is 0 to 2;

$R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl; phenyl and v is 0 to 2;

$R^{3a}$ and $R^{3b}$ are independently hydrogen, $R^9$, $C_1$-$C_6$ alkyl substituted with $R^9$, phenyl substituted with $R^9$, or phenoxy substituted with $R^9$;

$R^9$ is:

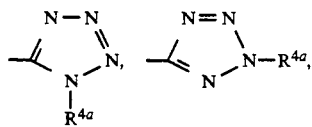

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4R^5NN(R^5)CO(CH_2)_v$—, $R^{7b}CON(R^4)N(R^5)CO(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 3;

$R^{12a}$, $R^{12b}$ and $R^{12c}$ are independently $R^{5a}$, $OR^{5a}$, or $COR^{5a}$; $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 3, $R^1$ is as defined above and $R^{10}$ is hydrogen, $C_1$-$C_6$ alkyl, phenyl $C_1$-$C_6$ alkyl or $C_1$-$C_5$ alkanoyl-$C_1$-$C_6$ alkyl;

$R^{13}$ is $C_1$-$C_3$ perfluoroalkyl, $C_1$-$C_6$ alkyl, substituted $C_1$-$C_6$ alkyl, where the substituents are hydroxy, —$NR^{10}R^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

X is as defined above;

$R^4$, $R^{4a}$, $R^{4b}$, $R^5$ and $R^{5a}$ are independently hydrogen, phenyl, substituted phenyl, $C_1$-$C_{10}$ alkyl, substituted $C_1$-$C_{10}$ alkyl, where the substituents on the alkyl or phenyl are from 1 to 5 of hydroxy, $C_1$-$C_6$ alkoxy, $C_3$-$C_7$ cycloalkyl, fluoro, $R^1$, $R^2$ independently disubstituted phenyl $C_1$-$C_3$ alkoxy, $R^1$, $R^2$ independently disubstituted phenyl, $C_1$-$C_{20}$-alkanoyloxy, $C_1$-$C_5$ alkoxycarbonyl, carboxy or formyl;

$R^4$ and $R^5$ can be taken together to form —$(CH_2)_r$B$(CH_2)_s$— where B is $CHR^1$, O, $S(O)_m$ or N—$R^{10}$, r and s are independently 1 to 3 and $R^1$ and $R^{10}$ are as defined above;

$R^6$ is hydrogen, $C_1$-$C_{10}$ alkyl or phenyl $C_1$-$C_{10}$ alkyl;

A is

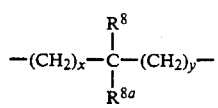

where x and y are independently 0-2;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy, formyl or —$NR^{10}R^{11}$ where $R^{10}$ and $R^{11}$ are independently hydrogen, $C_1$-$C_6$ alkyl, or $C_1$-$C_5$ alkanoyl-$C_1$-$C_6$ alkyl; or $R^8$ and $R^{8a}$ can be taken together to form —$(CH_2)_t$— where t is 2 to 4; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms; and pharmaceutically acceptable salts thereof.

Additional preferred compounds are realized in the above structural formula when:

q is 0 to 2;
w is 0 or 1;

$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, —$S(O)_mR^{7a}$, $R^{7b}O(CH_2)_v$—, $R^{7b}COO(CH_2)_v$—, $R^{7b}OCO(CH_2)_v$—, phenyl or substituted phenyl where the substituents are from 1 to 3 of halogen, $C_1$-$C_6$ alkyl, $C_1$-$C_6$ alkoxy, or hydroxy;

m is 0 or 1;

$R^{7a}$ and $R^{7b}$ are independently hydrogen, $C_1$-$C_6$ alkyl, substituted $C_1$-$C_6$ alkyl, where the substituents are phenyl and v is 0 to 2;

$R^{3a}$ and $R^{3b}$ are independently hydrogen, $R^9$, $C_1$-$C_6$ alkyl substituted with $R^9$, phenyl substituted with $R^9$, or phenoxy substituted with $R^9$;

$R^9$ is:

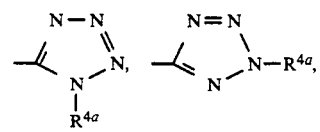

$R^{7b}O(CH_2)_v$—, $R^{7b}COO(CH_2)_v$—, $R^{7b}OCO(CH_2)_v$—, $R^{7b}CO(CH_2)_v$—, $R^4R^5N(CH_2)_v$—, $R^{7b}CON(R^4)(CH_2)_v$—, $R^4R^5NCO(CH_2)_v$—, $R^4R^5NCS(CH_2)_v$—, $R^4N(OR^{7b})CO(CH_2)_v$—, $R^{7a}CON(OR^{7b})CO(CH_2)_v$—, $R^{4b}R^{12a}NCON(R^{12b})(CH_2)_v$—, $R^{4b}R^{12a}NCSN(R^{12b})(CH_2)_v$—, $R^{4b}R^{12a}NN(R^{12b})CON(R^{12c})(CH_2)_v$—, $R^{4b}R^{12a}NN(R^{12b})COO(CH_2)_v$—, $R^{4b}R^{12a}NCOO(CH_2)_v$— or $R^{13}OCON(R^{12b})(CH_2)_v$—, where v is 0 to 2;

$R^{12a}$, $R^{12b}$ and $R^{12c}$ are independently $R^{5a}$ or $OR^{5a}$ $R^{12a}$ and $R^{12b}$, or $R^{12b}$ and $R^{12c}$, or $R^{13}$ and $R^{12b}$ or $R^{12a}$ and $R^{4b}$ can be taken together to form —$(CH_2)_r$—B—$(CH_2)_s$— where B is $CHR^1$, O, $S(O)_m$ or $NR^{10}$, m is 0, 1 or 2, r and s are independently 0 to 2, $R^1$ is as defined above and $R^{10}$ is hydrogen, $C_1$-$C_6$ alkyl or $C_1$-$C_5$ alkanoyl-$C_1$-$C_6$ alkyl;

$R^{13}$ is $C_1$-$C_6$ alkyl, substituted $C_1$-$C_6$ alkyl, where the substituents are phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy;

X is as defined above;

$R^4$, $R^{4a}$, $R^{4b}$, $R^5$ and $R^{5a}$ are independently hydrogen, $C_1$-$C_{10}$ alkyl, substituted $C_1$-$C_{10}$ alkyl, where the substituents on the alkyl are from 1 to 5 of hydroxy, $C_1$-$C_6$ alkoxy, fluoro, $R^1$, $R^2$ independently disubstituted phenyl, $C_1$-$C_{20}$-alkanoyloxy, $C_1$-$C_5$ alkoxycarbonyl or carboxy;

$R^6$ is hydrogen or $C_1$-$C_{10}$ alkyl;

A is

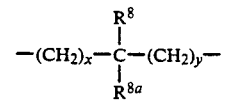

where x and y are independently 0-1;

$R^8$ and $R^{8a}$ are independently hydrogen, $C_1$-$C_{10}$ alkyl, substituted $C_1$-$C_{10}$ alkyl where the substituents are from 1 to 3 of imidazolyl, indolyl, hydroxy, fluoro, $S(O)_mR^{7a}$, $C_1$-$C_6$ alkoxy, $R^1$, $R^2$ independently disubstituted phenyl, $C_1$-$C_5$-alkanoyloxy, $C_1$-$C_5$ alkoxycarbonyl, carboxy; or $R^8$ and $R^{8a}$ can be taken together to form —(CH$_2$)$_t$— where t is 2; or $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Still further preferred compounds of the instant invention are realized when in the above structural formula:

q is 1;

w is 1;

$R^1$, $R^2$, $R^{1a}$, $R^{2a}$, $R^{1b}$, and $R^{2b}$ are independently hydrogen, halogen, C$_1$-C$_7$ alkyl, C$_1$-C$_3$ perfluoroalkyl, —S(O)$_m$R$^{7a}$, R$^{7b}$O(CH$_2$)$_v$—, R$^{7b}$COO(CH$_2$)$_v$—, phenyl or substituted phenyl where the substituents are from 1 to 3 of halogen, C$_1$-C$_6$ alkyl, C$_1$-C$_6$ alkoxy, or hydroxy;

m is 0 or 1;

$R^{7a}$ and $R^{7b}$ are independently hydrogen, C$_1$-C$_6$ alkyl, substituted C$_1$-C$_6$ alkyl, where the substituents are phenyl and v is 0 or 1;

$R^{3a}$ and $R^{3b}$ are independently hydrogen, $R^9$, or C$_1$-C$_6$ alkyl substituted with $R^9$;

$R^9$ is

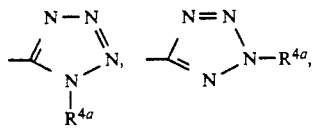

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{7b}$CON(R$^4$)(CH$_2$)$_v$—, R$^4$R$^5$NCO(CH$_2$)$_v$—, R$^4$N(OR$^{7b}$)CO(CH$_2$)$_v$—, R$^{4b}$R$^{12a}$NCON(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 1;

$R^{12a}$, $R^{12b}$ and $R^{12c}$ are independently $R^{5a}$ $R^{12a}$ and $R^{12b}$, or $R^{12b}$ and $R^{12c}$, or $R^{13}$ and $R^{12b}$ or $R^{12a}$ and $R^{4b}$ can be taken together to form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$-C$_6$ alkyl or C$_1$-C$_5$ alkanoyl-C$_1$-C$_6$ alkyl;

$R^{13}$ is C$_1$-C$_6$ alkyl, substituted C$_1$-C$_6$ alkyl, where the substituents are phenyl or substituted phenyl; phenyl or substituted phenyl where the substituents on the phenyl are from 1 to 3 of halogen, C$_1$-C$_6$ alkyl, C$_1$-C$_6$ alkoxy or hydroxy;

X is as defined above;

$R^4$, $R^{4a}$, $R^{4b}$, $R^5$, and $R^{5a}$ are independently hydrogen, C$_1$-C$_{10}$ alkyl, substituted C$_1$-C$_{10}$ alkyl, where the substituents on the alkyl are from 1 to 3 of hydroxy, C$_1$-C$_3$ alkoxy, fluoro, R$^1$, R$^2$ independently disubstituted phenyl, C$_1$-C$_{20}$ alkanoyloxy, C$_1$-C$_5$ alkoxycarbonyl or carboxy;

$R^6$ is hydrogen;

A is

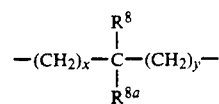

where x and y are independently 0-1;

$R^8$ and $R^{8a}$ are independently hydrogen, C$_1$-C$_{10}$ alkyl, substituted C$_1$-C$_{10}$ alkyl where the substituents are from 1 to 3 of imidazolyl, indolyl, hydroxy, fluoro, S(O)$_m$R$^{7a}$, C$_1$-C$_6$ alkoxy, R$^1$, R$^2$ independently disubstituted phenyl, C$_1$-C$_5$-alkanoyloxy, C$_1$-C$_5$ alkoxycarbonyl, carboxy; or $R^8$ and $R^{8a}$ can be taken together to form —(CH$_2$)$_t$— where t is 2; and $R^8$ and $R^{8a}$ can independently be joined to one or both of $R^4$ and $R^5$ to form alkylene bridges between the terminal nitrogen and the alkyl portion of the A group wherein the bridge contains from 1 to 5 carbon atoms;

and pharmaceutically acceptable salts thereof.

Representative examples of the nomenclature employed are given below:

3-Amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide

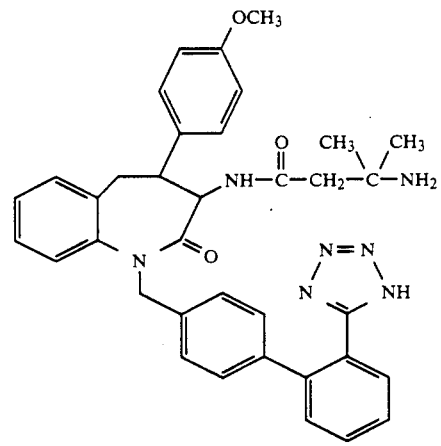

N-Ethyl-4'-[[3-[(2-amino-2-methyl-1-oxopropyl)amino]-2,3,4,5-tetrahydro-2-oxo-5-methyl-1H-1-benzazepin-1-yl]methyl][1,1'-biphenyl]-2-carboxamide

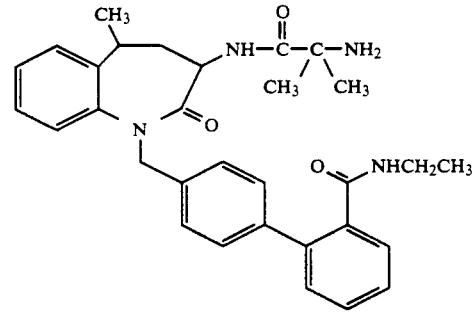

N-[1-[[2'-[(Methylaminocarbonyl)amino][1,1'-biphenyl]-4-yl]methyl]-2,3,-dihydro-2-oxo-4-phenyl-1H-1-benzazepin-3-yl]-3-(2(R)-hydroxypropyl)amino-3-methylbutanamide

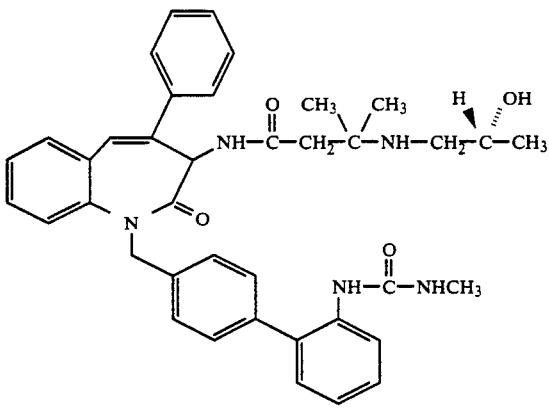

N-[5-[[2'-[(Methylaminocarbonyl)oxy][1,1'-biphenyl]-4-yl]methyl]-2,3,4,5-tetrahydro-4-oxo-2-(4-hydroxyphenyl)-5H-1,5-benzothiazepin-3-yl]-3-[2(S),3-dihydroxypropyl]amino-3-methylbutanamide

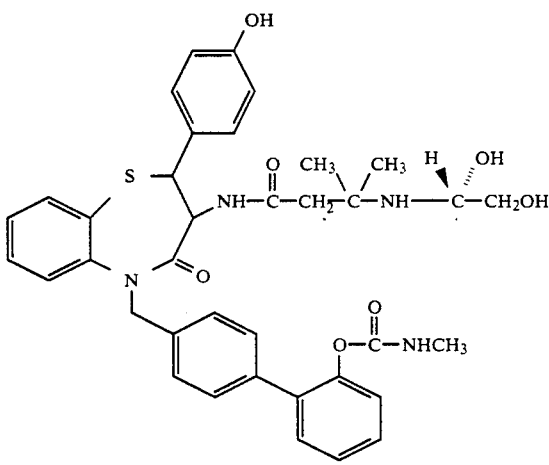

Representative preferred growth hormone releasing compounds of the present invention include the following:

1. 3-Amino-3-methyl-N-[2,3,4,5-tetrahydro-2-oxo-4-(4-methoxyphenyl)-1-[[2'-(1H-tetrazol-5-yl)[1,-1'-biphenyl]-4-yl]methyl]-1H-1-benzazepin-3-yl]butanamide
2. 3-Amino-3-methyl-N-[2,3,4,5-tetrahydro-2-oxo-4-(4-hydroxyphenyl)-1-[[2'-(1H-tetrazol-5-yl)[1,-1'-biphenyl]-4-yl]methyl]-1H-1-benzazepine-3-yl]butanamide
3. 3-Amino-3-methyl-N-[2,3,4,5-tetrahydro-2-oxo-4-phenyl-1-[[2'-(1H-tetrazol-5-yl)[1,1'-biphenyl]-4-yl]methyl-1H-1-benzazepin-3-yl]-butanamide
4. 3-[2(R)-Hydroxypropyl]amino-3-methyl-N-[2,3 4,5-tetrahydro-2-oxo-4-phenyl-1-[[2'-(1H-tetrazol-5-yl)[1,1'-biphenyl]-4-yl]methyl]-1H-1-benzazepin-3-yl]-butanamide
5. 3-Amino-3-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-butanamide
6. 3-Amino-3-methyl-N-[7-trifluoromethyl-2,3,4,5-tetrahydro-2-oxo-5-methyl-1-[[2'-(1H-tetrazol-5-yl)[1,1'-biphenyl]-4-yl]methyl]-1H-1-benzazepin-3yl]-butanamide
7. 3-Amino-3-methyl-N-[7-fluoro-2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide
8. 3-Amino-3-methyl-N-[7-methylthio-2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide
9. 3-[2(R)-Hydroxypropyl]amino-3-methyl-N-[2,3,4,5-tetrahydro-2-oxo-4-phenylthio-1-[[2'-(1H-tetrazol-5-yl)[1,1'-biphenyl]-4-yl]methyl-1H-1-benzazepin-3-yl]-butanamide
10. 3-[2(R)-Hydroxypropyl]amino-3-methyl-N-[2,3,4,5-tetrahydro-2-oxo-5-phenylthio-1-[[2'-(1H-tetrazol-5-yl)[1,1'-biphenyl]-4-yl]methyl-1H-1-benzazepin-3-yl]-butanamide
11. 3-[2(R)-Hydroxypropyl]amino-3-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-butanamide
12. 3-[2(S),3-Dihydroxypropyl]amino-3-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-butanamide
13. 3-Amino-3-methyl-N-[2,3,4,5-tetrahydro-2-oxo-4-methyl-1-[[2'-(1H-tetrazol-5-yl)[1,1'-biphenyl]-4-yl]methyl-1H-1-benzazepin-3-yl]-butanamide
14. 3-[2(R)-Hydroxypropyl]amino-3-methyl-N-[2,3,4,5-tetrahydro-2-oxo-4-methyl-1-[[2'-(1H-tetrazol-5-yl)[1,1'-biphenyl]-4-yl]methyl-1H-1-benzazepin-3-yl]-butanamide
15. 3-Amino-3-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-butanamide
16. 3-[2(R)-Hydroxypropyl]amino-3-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-butanamide
17. 3-[2(S),3-Dihydroxypropyl]amino-3-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-butanamide
18. 2-Amino-2-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-propanamide
19. 2-Amino-2-methyl-N-[7-methylthio-2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-propanamide
20. 2-Amino-2-methyl-N-[2,3,4,5-tetrahydro-2-oxo-4-phenyl-1-[[2'-(1H-tetrazol-5-yl)[1,1'-biphenyl]-4-yl]methyl-1H-1-benzazepin-3-yl]-propanamide
21. 2-Amino-2-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-propanamide
22. 2-Amino-2-methyl-N-[2,3,4,5-tetrahydro-2-oxo-4-methyl-1-[[2'-(1H-tetrazol-5-yl)[1,1'-biphenyl]-4-yl]methyl-1H-1-benzazepin-3-yl]-propanamide
23. 2-Amino-2-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-propanamide
24. 2-Amino-2-methyl-N-[7-fluoro-2,3,4,5-tetrahydro-2-oxo-5-methyl-1-[[2'-(1H-tetrazol-5-yl)[1,1'-biphenyl]-4-yl]methyl-1H-1-benzazepin-3-yl]-propanamide
25. 2-Amino-2-methyl-N-[7-trifluoromethyl-2,3,4,5-tetrahydro-2-oxo-4-methyl-1-[[2'-(1H-tetrazol-5-yl)[1,1'-biphenyl]-4-yl]methyl-1H-1-benzazepin-3-yl]-propanamide 26. N-Ethyl-4'-[[3-[(3-amino-3-methyl-1-oxobutyl)-amino]-2,3,4,5-tetrahydro-2-oxo-4-methyl-1H-1-benzazepin-1-yl]methyl][1,1'-biphenyl]-2-carboxamide
27. 4'-[[3-[(3-Amino-3-methyl-1-oxobutyl)amino]-2,3,4,5-tetrahydro-2-oxo-5-methyl-1H-1-benzazepin-1-yl]methyl][1,1'-biphenyl]-2-carboxamide
28. N-Ethyl-4'-[[3-[(3-amino-3-methyl-1-oxobutyl)amino]-2,3,4,5-tetrahydro-2-oxo-4,5-dimethyl-1H-1-benzazepin-1-yl]methyl][1,1'-biphenyl]-2-carboxamide
29. N-Ethyl-4'-[[3-[(3-amino-3-methyl-1-oxobutyl)amino]-2,3,4,5-tetrahydro-2-oxo-4-(4-methoxyphenyl)-1H-1-benzazepin-1-yl]methyl][1,1'-biphenyl]-2-carboxamide
30. 4'-[[3-[(3-Amino-3-methyl-1-oxobutyl)amino]-2,3,4,5-tetrahydro-2-oxo-5-phenylthio-1H-1-benzazepin-1-yl]methyl][1,1'-biphenyl]-2-carboxamide
31. N-Ethyl-4'-[[3-[(2-amino-2-methyl-1-oxopropyl)amino]-2,3,4,5-tetrahydro-2-oxo-4-methyl-1H-1-benzazepin-1-yl]methyl][1,1'-biphenyl]-2-carboxamide
32. N-Ethyl-4'-[[3-[(2-amino-2-methyl-1-oxopropyl)amino]-2,3,4,5-tetrahydro-2-oxo-5-methyl-1H-1-benzazepin-1-yl]methyl][1,1'-biphenyl]-2-carboxamide
33. N-Ethyl-4'-[[3-[(2-amino-2-methyl-1-oxopropyl)amino]-7-fluoro-2,3,4,5-tetrahydro-2-oxo-5-methyl-1H-1-benzazepin-1-yl]methyl][1,1'-biphenyl]-2-carboxamide
34. N-Ethyl-4'-[[3-[(2-amino-2-methyl-1-oxopropyl)amino]-2,3,4,5-tetrahydro-2-oxo-4,5-dimethyl-1H-1-benzazepin-1-yl]methyl][1,1'-biphenyl]-2-carboxamide
35. N-Ethyl-4'-[[3-[(2-amino-2-methyl-1-oxopropyl)amino]-2,3,4,5-tetrahydro-2-oxo-4-(4-methoxyphenyl)-1H-1-benzazepin-1-yl]methyl][1,1'-biphenyl]-2-carboxamide
36. N-Ethyl-4'-[[3-[[3-[2(R)-hydroxypropylamino]-3-methyl-1-oxobutyl]amino]-2,3,4,5-tetrahydro-2-oxo-4-methyl-1H-1-benzazepln-1-yl]methyl][1,1'-biphenyl]-2-carboxamide
37. N-4'-[[3-[[3-[2(R)-Hydroxypropylamino]-3-methyl-1-oxobutyl]amino]-2,3,4,5-tetrahydro-2-oxo-5-phenyl-1H-1-benzazepin-1-yl]methyl][1,1'-biphenyl]-2-carboxamide
38. N-4'-[[3-[[3-[2(R)-Hydroxypropylamino]-3-methyl-1-oxobutyl]amino]-7-fluoro-2,3,4,5-tetrahydro-2-oxo-5-methyl-1H-1-benzazepin-1-yl]methyl][1,1'-biphenyl]-2-carboxamide
39. N-Ethyl-4'-[[3-[(3-[[3-[2(R)-hydroxypropylamino]-3-methyl-1-oxobutyl) amino]-2,3,4,5-tetrahydro-2-oxo-4,5-dimethyl-1H-1-benzazepin-1-yl]methyl][1,1'-biphenyl]-2-carboxamide
40. N-Ethyl-4'-[[3-[(3-[[3-[2(R)-hydroxypropylamino]-3-methyl-1-oxobutyl) amino]-2,3,4,5-tetrahydro-2-oxo-4-(4-methoxyphenyl)-1H-1-benzazepin-1-yl]methyl][1,1'-biphenyl]-2-carboxamide
41. 4'-[[3-[(3-[[3-[2(R)-Hydroxypropylamino]-3-methyl-1-oxobutyl) amino]-2,3,4,5-tetrahydro-2-oxo-5-phenylthio-1H-1-benzazepin-1-yl]methyl][1,1'-biphenyl]-2-carboxamide
42. N-Ethyl-4'-[[3-[(3-[2(S),3-dihydroxypropylamino]-3-methyl-1-oxobutyl) amino]-2,3,4,5-tetrahydro-2-oxo-4-methyl-1H-1-benzazepin-1-yl]methyl][1,1'-biphenyl]-2-carboxamide
43. 4'-[[3-[(3-[2(S),3-Dihydroxypropylamino]-3-methyl-1-oxobutyl) amino]-2,3,4,5-tetrahydro-2-oxo-5-methyl-1H-1-benzazepin-1yl]methyl][1,1'-biphenyl]-2-carboxamide
44. N-Ethyl-4'-[[3-[(3-[2(S),3-dihydroxypropylamino]-3-methyl-1-oxobutyl)amino]-2,3,4,5-tetrahydro-2-oxo-4-(4-methoxyphenyl)-1H-1-benzazepin-1-yl]methyl][1,1'-biphenyl]-2-carboxamide
45. N-[1-[[2'-[(Methylaminocarbonyl)amino][1,1'-biphenyl]-4-yl]methyl]-2,3,4,5-tetrahydro-2-oxo-4-methyl-1H-1-benzazepin-3-yl]-3-amino-3-methylbutanamide
46. N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-3-amino-3-methylbutanamide
47. N-[1-[[2'-[(Morpholinocarbonyl)amino][1,1'-biphenyl]-4-yl]methyl]-2,3,4,5-tetrahydro-2-oxo-5-methyl-1H-1-benzazepin-3-yl]-3-amino-3-methylbutanamide
48. N-[1-[[2'-[[(2-Hydroxyethylamino)carbonyl]amino][1,1'-biphenyl]-4-yl]methyl]-2,3,4,5-tetrahydro-2-oxo-4-methyl-1H-1-benzazepin-3-yl]-3-amino-3-methylbutanamide
49. N-[1-[[2'-[[(2-Hydroxyethylamino)carbonyl]amino][1,1'-biphenyl]-4-yl]methyl]-2,3,4,5-tetrahydro-2-oxo-5-methyl-1H-1-benzazepin-3-yl]-3-amino-3-methylbutanamide
50. N-[1-[[2'-[[(2-Hydroxyethylamino)carbonyl]amino][1,1'-biphenyl]-4-yl]methyl]-2,3,4,5-tetrahydro-2-oxo-4-(4-methoxyphenyl)-1H-1-benzazepin-3-yl]-3-amino-3-methylbutanamide
51. N-[1-[[2'-[[(2-Hydroxyethylamino)carbonyl]amino][1,1'-biphenyl]-4-yl]methyl]-2,3,4,5-tetrahydro-2-oxo-5-phenyl-1H-1-benzazepin-3-yl]-3-amino-3-methylbutanamide
52. N-[1-[[2'-[[(2-Hydroxyethylamino)carbonyl]amino][1,1'-biphenyl]-4-yl]methyl]-2,3,4,5-tetrahydro-2-oxo-4,5-dimethyl-1H-1-benzazepin-3-yl]-3-amino-3-methylbutanamide
53. N-[1-[[2'-[(Methylaminocarbonyl)oxy][1,1'-biphenyl]-4-yl]methyl]-2,3,4,5-tetrahydro-2-oxo-5-methyl-1H-1-benzazepin-3-yl]-3-amino-3-methylbutanamide
54. N-[1-[[2'-[2-[(Methylaminocarbonyl)amino]phenoxy][1,1'-biphenyl]-4-yl]methyl]-2,3,4,5-tetrahydro-2-oxo-4-methyl-1H-1-benzazepin-3-yl]-3-amino-3-methylbutanamide
55. N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-3-(2(R)-hydroxypropyl)amino-3-methylbutanamide 
56. N-[1-[[2'-(Methylaminocarbonyl)amino][1,1'-biphenyl]-4-yl]methyl]-2,3,4,5-tetrahydro-2-oxo-5-methyl-1H-1-benzazepin-3-yl]-3-[2(S),3-dihydroxypropyl]amino-3-methylbutanamide
57. N-[1-[[2'-[(Morpholinocarbonyl)amino][1,1'-biphenyl]-4-yl]methyl]-2,3,4,5-tetrahydro-2-oxo-5-methyl-1H-1-benzazepin-3-yl]-3-(2(R)-hydroxypropyl)amino-3-methylbutanamide
58. N-[1-[[2'-[(Morpholinocarbonyl)amino][1,1'-biphenyl]-4-yl]methyl]-2,3,4,5-tetrahydro-2-oxo-5-methyl-1H-1-benzazepin-3-yl]-3-[2(S),3-dihydroxypropyl]amino-3-methylbutanamide
59. N-[1-[[2'-[[(2-Hydroxyethylamino)carbonyl]amino][1,1'-biphenyl]-4-yl]methyl]-2,3,4,5-tetrahydro-2-oxo-5-methyl-1H-1-benzazepin-3-yl]-3-(2(R)-hydroxypropyl)amino-3-methylbutanamide
60. N-[1-[[2'-[[(2-Hydroxyethylamino)carbonyl]amino][1,1'-biphenyl]-4-yl]methyl]-2,3,4,5-tetrahydro-2-oxo-5-methyl-1H-1-benzazepin-3-yl]-3-[2(S),3-dihydroxypropyl]amino-3-methylbutanamide 61. N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-2-amino-2-methylpropanamide
62. N-[1-[[2'-[(Methylaminocarbonyl)amino][1,1'-biphenyl]-4-yl]methyl]-7-fluoro-2,3,4,5-tetrahydro-2-oxo-5-methyl-1H-1-benzazepin-3-yl]-2-amino-2-methylpropanamide
63. N-[1-[[2'-[(Methylaminocarbonyl)amino][1,1'-biphenyl]-4-yl]methyl]-2,3,4,5-tetrahydro-2-oxo-5-phenyl-1H-1-benzazepin-3-yl]-2-amino-2-methylpropanamide
64. N-[1-[[2'-[(Methylaminocarbonyl)amino][1,1'-biphenyl]-4-yl]methyl]-2,3,4,5-tetrahydro-2-oxo-4-methyl-1H-1-benzazepin-3-yl]-2-amino-2-methylpropanamide
65. N-[1-[[2'-[(Morpholinocarbonyl)amino][1,1'-biphenyl]-4-yl]methyl]-2,3,4,5-tetrahydro-2-oxo-4-(4-methoxyphenyl)-1H-1-benzazepin-3-yl]-2-amino-2-methylpropanamide
66. N-[1-[[2'-[[(2-Hydroxyethylamino)carbonyl]amino][1,1'-biphenyl]-4-yl]methyl]-2,3,4,5-tetrahydro-2-oxo-4-(4-methoxyphenyl)-1H-1-benzazepin-3-yl]-2-amino-2-methylpropanamide
67. N-[1-[[2'-[(Methylaminocarbonyl)amino][1,1'-biphenyl]-4-yl]methyl]-7-fluoro-2,3,4,5-tetrahydro-2-oxo-4-methyl-1H-1-benzazepin-3-yl]-3-(2(R)-hydroxypropyl)amino-3-methylbutanamide
68. N-[1-[[2'-[(Methylaminocarbonyl)amino][1,1'-biphenyl]-4-yl]methyl]-7-fluoro-2,3,4,5-tetrahydro-2-oxo-5-methyl-1H-1-benzazepin-3-yl]-3-(2(R)-hydroxypropyl)amino-3-methylbutanamide
69. N-[1-[[2'-[(Methylaminocarbonyl)amino][1,1'-biphenyl]-4-yl]methyl]-7-fluoro-2,3,4,5-tetrahydro-2-oxo-4-phenyl-1H-1-benzazepin-3-yl]-3-[2(S),3-dihydroxypropyl]amino-3-methylbutanamide
70. N-[1-[[2'-[[(2-Hydroxyethylamino)carbonyl]amino][1,1'-biphenyl]-4-yl]methyl]-7-fluoro-2,3,4,5-tetrahydro-2-oxo-5-methyl-1H-1-benzazepin-3-yl]-3-(2(R)-hydroxypropyl)amino-3-methylbutanamide
71. 3-Amino-3-methyl-N-[2,3,4,5-tetrahydro-2-oxo-4-(4-methoxyphenyl)-1-[[2'-hydroxymethyl[1,1'-biphenyl]-4-yl]methyl]-1H-1-benzazepin-3-yl]-butanamide
72. 3-Amino-3-methyl-N-[2,3,4,5-tetrahydro-2-oxo-5-methyl-1-[[2'-hydroxymethyl[1,1'-biphenyl]-4-yl]methyl-1H-1-benzazepin-3-yl]-butanamide
73. 3-Amino-3-methyl-N-[2,3,4,5-tetrahydro-2-oxo-4-methyl-1-[[2'-hydroxymethyl[1,1'-biphenyl]-4-yl]methyl-1H-1-benzazepin-3-yl]-butanamide
74. 3-[2(R)-Hydroxypropyl]amino-3-methyl-N-[2,3,4,5-tetrahydro-2-oxo-5-methyl-1-[[2'-hydroxymethyl[1,1'-biphenyl]-4-yl]methyl-1H-1-benzazepin-3-yl]-butanamide
75. 2-Amino-2-methyl-N-[2,3,4,5-tetrahydro-2-oxo-5-methyl-1-[[2'-hydroxymethyl[1,1'-biphenyl]-4-yl]methyl-1H-1-benzazepin-3-yl]-propanamide
76. 3-Amino-3-methyl-N-[2,3-dihydro-2-oxo-5-methyl-1-[[2'-(1H-tetrazol-5-yl)[1,1'-biphenyl]-4-yl]methyl]-1H-1-benzazepin-3-yl]-butanamide
77. 3-Amino-3-methyl-N-[2,3-dihydro-2-oxo-4-(4-methoxyphenyl)-1-[[2'-(1H-tetrazol-5-yl)[1,1'-biphenyl]-4-yl]methyl-1H-1-benzazepin-3-yl]-butanamide
78. 3-[2(R)-Hydroxypropyl]amino-3-methyl-N-[2,3-dihydro-2-oxo-5-methyl-1-[[2'-(1H-tetrazol-5-yl)[1,1'-biphenyl]-4-yl]methyl-1H-1-benzazepin-3-yl]-butanamide
79. 2-Amino-2-methyl-N-[2,3-dihydro-2-oxo-5-methyl-1-[[2'-(1H-tetrazol-5-yl)[1,1'-biphenyl]-4-yl]methyl-1H-1-benzazepin-3-yl]-propanamide
80. N-Ethyl-4'-[[3-[(3-amino-3-methyl-1-oxobutyl) amino]-2,3-dihydro-2-oxo-5-methyl-1H-1-benzazepin-1-yl]methyl][1,1'-biphenyl]-2-carboxamide
81. N-[1-[[2'-[(Methylaminocarbonyl)amino][1,1'-biphenyl]-4-yl]methyl]-2,3-dihydro-2-oxo-5-methyl-1H-1-benzazepin-3-yl]-3-amino-3-methylbutanamide
82. N-[1-[[2'-[(Methylaminocarbonyl)oxy][1,1'-biphenyl]-4-yl)methyl]-2,3-dihydro-2-oxo-5-methyl-1H-1-benzazepin-3-yl]-3-amino-3-methylbutanamide
83. 3-Amino-3-methyl-N-[2,3-dihydro-2-oxo-5-methyl-1-[[2'-hydroxymethyl[1,1'-biphenyl]-4-yl]methyl-1H-1-benzazepin-3-yl]-butanamide
84. 3-Amino-3-methyl-N-[2,3,4,5-tetrahydro-4-oxo-2-(4-methoxyphenyl)-5-[[2'-(1H-tetrazol-5-yl)[1,-1'-biphenyl]-4-yl]methyl-5H-1,5-benzothiazepin-3-yl]-butanamide
85. 3-Amino-3-methyl-N-[2,3,4,5-tetrahydro-4-oxo-2-methyl-5-[[2'-(1H-tetrazol-5-yl)[1,1'-biphenyl]-4-yl]methyl-5H-1,5-benzothiazepin-3-yl]-butanamide
86. 2-Amino-2-methyl-N-[2,3,4,5-tetrahydro-4-oxo-2-methyl-5-[[2'-(1H-tetrazol-5-yl)[1,1'-biphenyl]-4-yl]methyl-5H-1,5-benzothiazepin-3-yl]-propanamide
87. 3-Amino-3-methyl-N-[2,3,4,5-tetrahydro-4-oxo-2-methyl-5-[[2'-hydroxymethyl[1,1'-biphenyl]-4-yl]methyl-5H-1,5-benzothiazepin-3-yl]-butanamide
88. N-Ethyl-4'-[[3-[(3-amino-3-methyl-1-oxobutyl) amino]-2,3,4,5-tetrahydro-4-oxo-2-methyl-5H-5-benzothiazepin-5-yl]methyl][1,1'-biphenyl]-2-carboxamide
89. 4'-[[3-[(3-[2(S),3-Dihydroxypropylamino]-3-methyl-1-oxobutyl)amino]-2,3,4,5-tetrahydro-4-oxo-2-methyl-5H-5-benzothiazepin-5-yl]methyl]-[1,1'-biphenyl]-2-carboxamide
90. N-[5-[[2'-[(Methylamino)carbonyl]amino][1,1'-biphenyl]-4-yl]methyl]-2,3,4,5-tetrahydro-2-methyl-4-oxo-5H-1,5-benzothiazepin-3-yl]-3-amino-3-methylbutanamide
91. N-[5-[[2'-[(2-Hydroxyethylamino)carbonyl]amino][1,1'-biphenyl]-4-yl]methyl]-2,3,4,5-tetrahydro-4-oxo-1,5-benzothiazepin-3-yl]-3-amino-3-methylbutanamide
92. N-[5-[[2'-[(Methylamino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide
93. N-[5-[[2'-[(Morpholino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide
94. N-[5-[[2'-[(2-Hydroxyethylamino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide
95. N-5-[[2'-[(Methylamino)carbonyl]amino][1,1'-biphenyl]-4-yl]methyl]-2,3,4,5-tetrahydro-4-oxo-1,5-benzothiazepin-3-yl]-3-[2(S),3-dihydroxypropyl]amino-3-methylbutanamide The compounds of the instant invention all have at least one asymmetric center as noted by the asterisk in the structural Formula I above. Additional asymmetric centers may be present on the molecule depending upon the nature of the various substituents on the molecule. Each such asymmetric center will produce two optical isomers and it is intended that all such optical isomers, as separated, pure or partially purified optical isomers or racemic mixtures thereof, be included within the ambit of the instant invention. In the case of the asymmetric center represented by the asterisk in Formula I, it has been found that the compound in which the 3-amino substituent is above the plane of the structure, as seen in Formula Ia, is more active and thus more preferred over the compound in which the 3-amino substituent is below the plane of the structure. This center will be designated according to the R/S rules as either R or S depending upon the value of X.

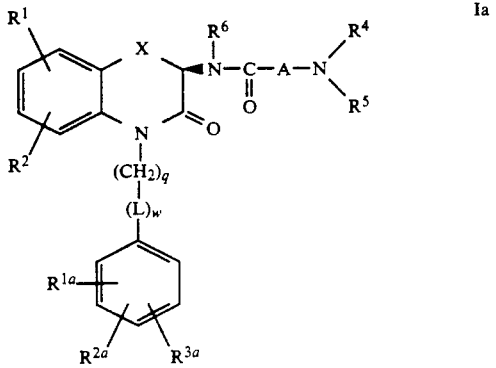

The instant compounds are generally isolated in the form of their pharmaceutically acceptable acid addition salts, such as the salts derived from using inorganic and organic acids. Examples of such acids are hydrochloric, nitric, sulfuric, phosphoric, formic, acetic, trifluoroacetic, propionic, maleic, succinic, malonic and the like. In addition, certain compounds containing an acidic function such as a carboxy or tetrazole, can be isolated in the form of their inorganic salt in which the counterion can be selected from sodium, potassium, lithium, calcium, magnesium and the like, as well as from organic bases.

Compounds I of the present invention are prepared from aminolactam intermediates such as those of formula II. The preparation of these intermediates is described in the following Schemes.

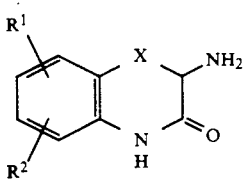

Benzo-fused lactams 7 of formula I wherein X is —CH($R^{21}$)CH$_2$— are prepared from substituted tetralones 6 using known procedures. The substituted tetralones are, in some cases, commercially available or can be prepared from a suitably substituted derivative of 4-phenylbutyric acid 5 as shown in Scheme 1.

SCHEME 1

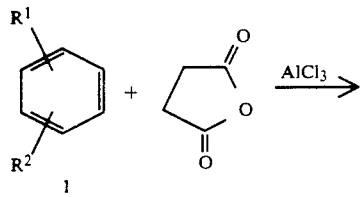

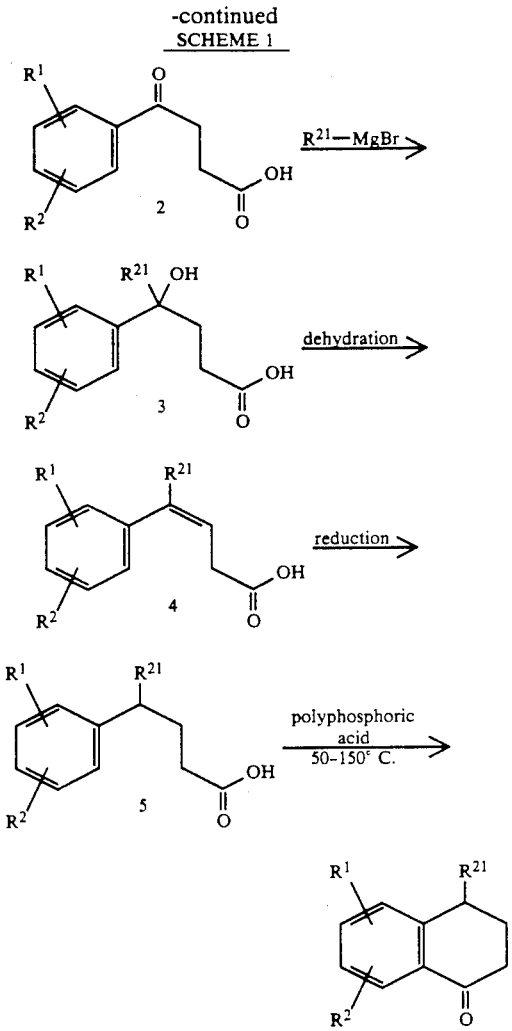

Acylation of 1 with succinic anhydride gives keto-acid 2 which can be reacted with an organometallic species, such as the Grignard reagent $R^{21}$-MgBr, to afford a tertiary alcohol 3. Dehydration to give olefin 4 can be achieved under conditions known in the literature and familiar to one skilled in the art. Reduction of the double bond of 4 is achieved by hydrogenation in the presence of a platinum or palladium catalyst, in a polar solvent such as methanol. Cyclization of 5 can be achieved by a number of methods well known in the art including treatment with polyphosphoric acid at elevated temperatures as shown. An alternate route to 5 would involve Wittig reaction of keto-acid 2 followed by reduction and cyclization by the aforementioned procedures.

Conversion of tetralones 6 to benzolactams 7 can be achieved by a number of methods familiar to those skilled in the art. A suitable method involves the use of hydrazoic acid (Schmidt reaction) to effect rearrangement as illustrated in Scheme 2. A preferred route proceeds through an intermediate oxime (Beckman rearrangment). Formation of the oxime 8 by treatment with hydroxylamine is conveniently carried out in high yield under mild conditions. Rearrangement to the desired benzolactam 7 is achieved by treatment with a strong acid, such as methanesulfonic acid.

SCHEME 2

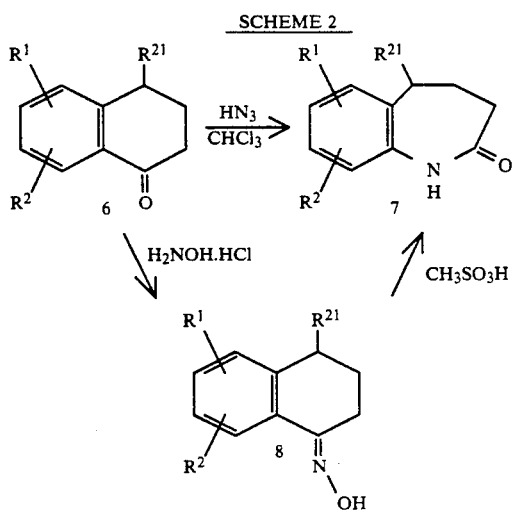

Compounds of formula I wherein X is —CH$_2$CH(R$^{20}$)— are prepared from substituted tetralones using an analogous route as shown in Scheme 3. Alkylation of keto-ester 9 can be achieved by a variety of routes known in the literature and familiar to one skilled in the art. A convenient route involves formation of the enolate of 9 with a strong base, such as lithium diisopropylamide, in a polar solvent, such as tetrahydrofuran, followed by alkylation with R$^{20}$—Y, wherein Y is a leaving group. Subsequent reduction, dehydration, saturation of the double bond, hydrolysis, cyclization and benzolactam formation are accomplished by the methods described in Schemes 1 and 2.

SCHEME 3

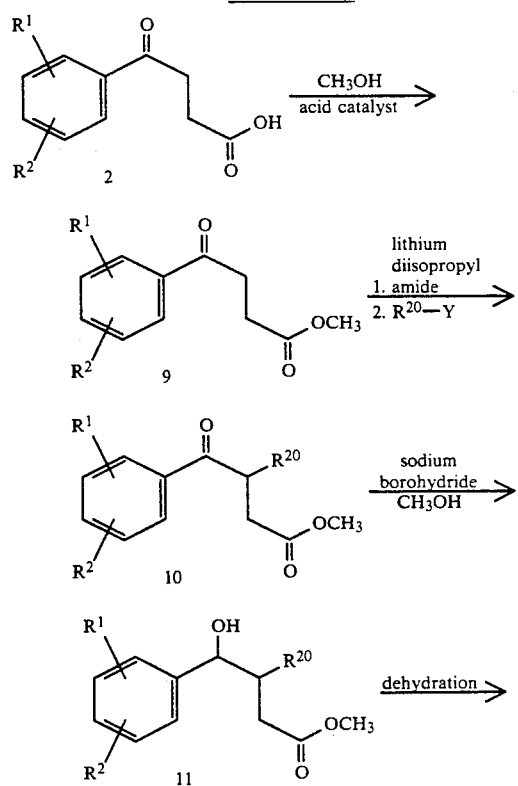

-continued
SCHEME 3

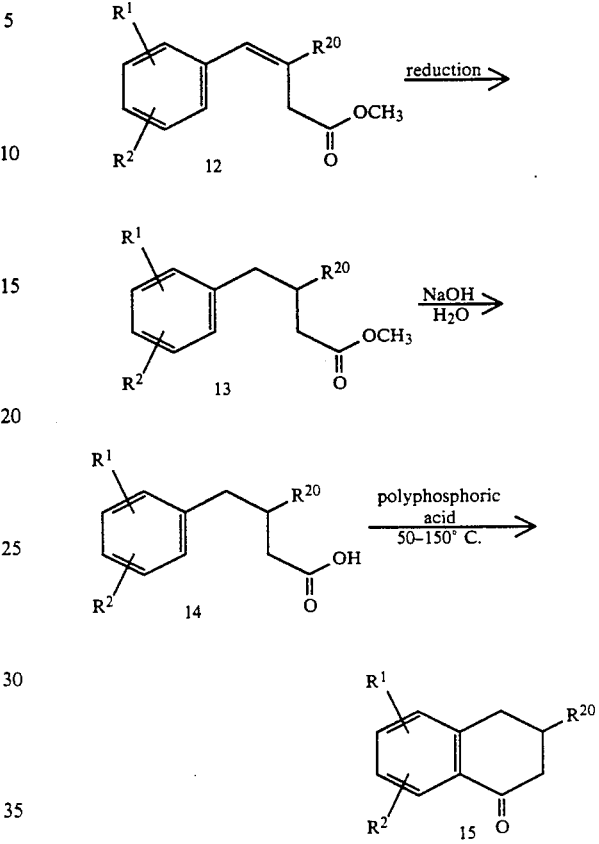

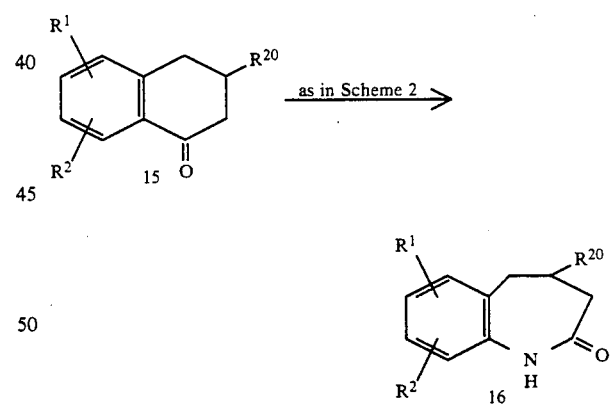

The subclass of analogs wherein X is —CH$_2$CH(R$^{20}$)— and R$^{20}$ is substituted phenyl (22) are prepared according to the procedure of D. Floyd, et al [J. Med. Chem., 35, 756–772 (1992).] as illustrated in Scheme 4. Addition of the 2-nitrotolyl anion of 17 to 18 affords unsaturated diester 19 which is reduced and cyclized to give the intermediate benzolactam 21. De-esterification and decarboxylation are carried out by treatment of 21 with lithium iodide in pyridine at elevated temperature.

SCHEME 4

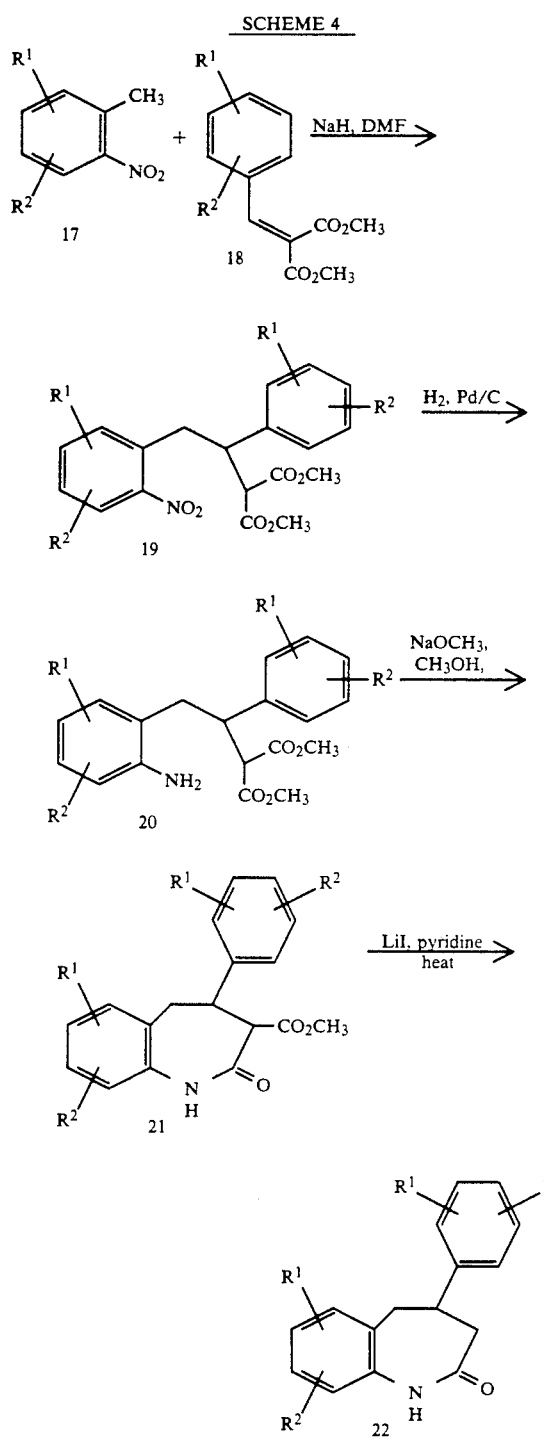

SCHEME 5

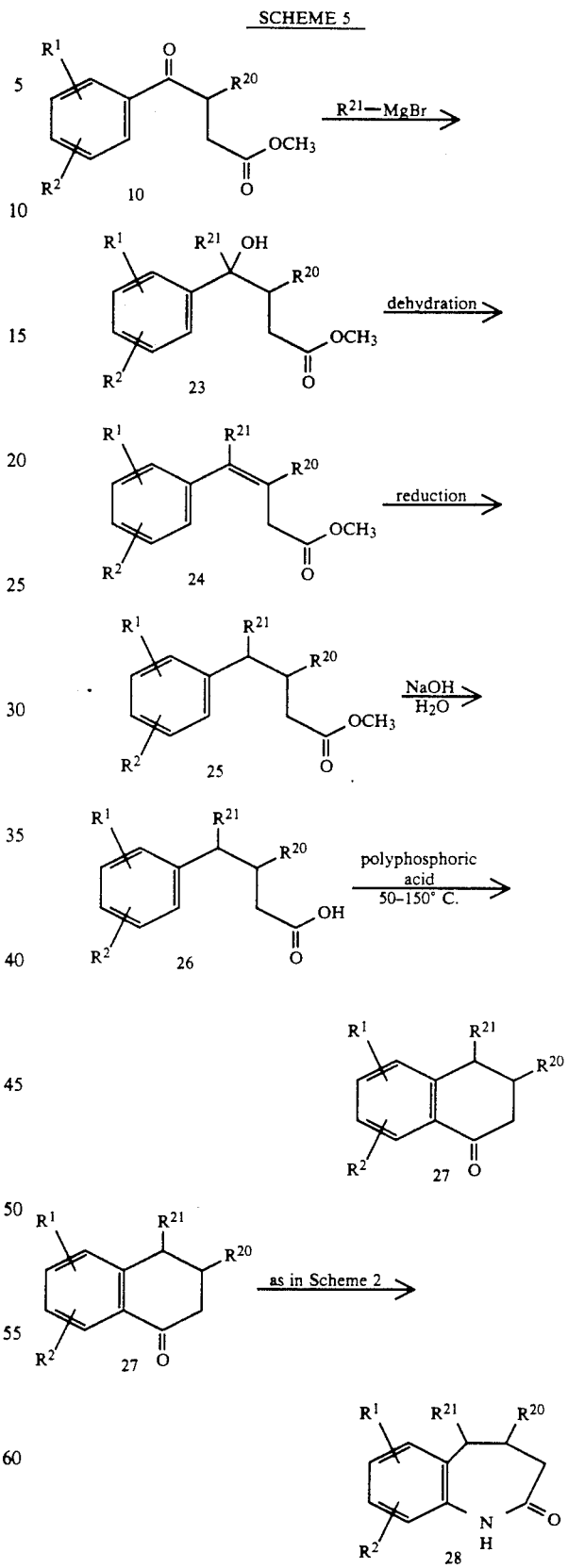

Compounds of formula I wherein X is —CH(R²¹)CH(R²⁰)— are prepared as described in Scheme 5. Intermediate 10, prepared as described in Scheme 3, is treated with a nucleophilic organometallic reagent, for example the Grignard reagent R²¹—MgBr, to afford alcohol 23. Conversion of 23 to the desired benzolactam 28 is carried out by the procedures described in Schemes 1 and 2. A different route may involve Wittig reaction of keto-ester 10, followed by elaboration to 25 by the steps described above.

Conversion of substituted benzo-fused lactams to the requisite 3-amino derivatives can be achieved by a number of methods familiar to those skilled in the art, including those described by Watthey, et al, J. Med. Chem., 28, 1511-1516 (1985) and references cited therein. One common route proceeds via the 3-halo(-chloro, bromo or iodo) intermediate which is subsequently displaced by a nitrogen nucleophile, typically azide. A useful method of forming the 3-iodobenzolactam 30 involves treating the benzolactam 29 with two equivalents each of iodotrimethylsilane and iodine at low temperature, as illustrated in Scheme 6.

SCHEME 6

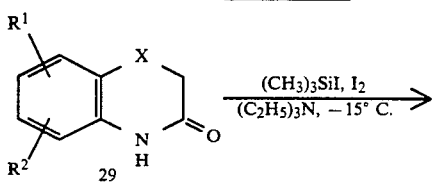

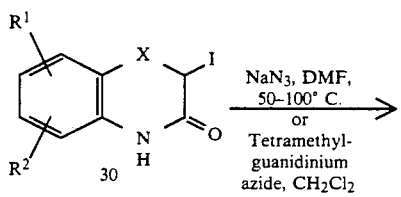

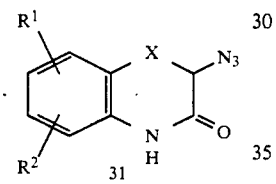

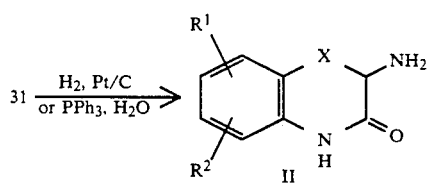

Elaboration of the iodo-benzolactams to the desired aminolactam intermediates II is achieved by a two-step procedure illustrated in Scheme 6. Typically, iodo-benzolactams 30 are treated with sodium azide in N,N-dimethylformamide at 50°-100° C. to give the 3-azido derivatives 31. Alternatively, tetramethylguanidinium azide in a solvent such as methylene chloride can be employed to achieve similar results. Hydrogenation with a metal catalyst, such as platinum on carbon, or alternatively, treatment with triphenylphosphine in wet toluene, results in formation of the amine derivative II.

Carbocyclic compounds of formula I containing a C-4/C-5 double bond can be prepared from suitably protected derivatives of the 5-keto analog 32. The synthesis of 32 (wherein G and G' are both hydrogen) from derivatives of tryptophan is described in the Australian Journal of Chemistry, 33, 633-640 (1980) and references cited therein. Treatment of 32 with a Grignard reagent, followed by dehydration and removal of protecting groups gives the desired unsaturated intermediate 35, substituted at C-5.

SCHEME 7

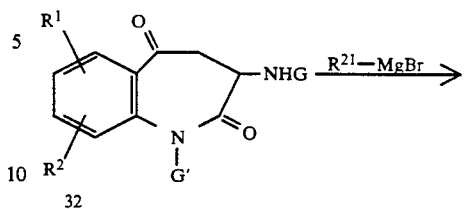

A similar route can be employed in the synthesis of the C-4 substituted compound 39. Alkylation of the lithium enolate of 32 with $R^{20}$—Y, followed by reduction of the 5-keto group gives alcohol 37. Conversion to the desired intermediate 39 is executed as described above.

SCHEME 8

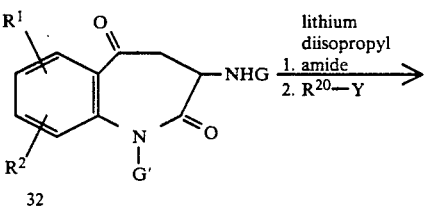

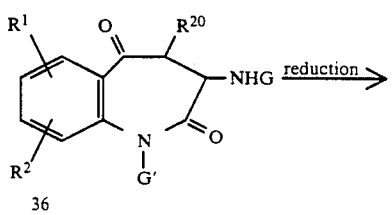

-continued
SCHEME 8

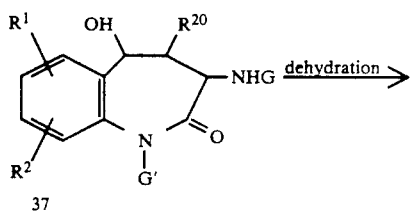
37

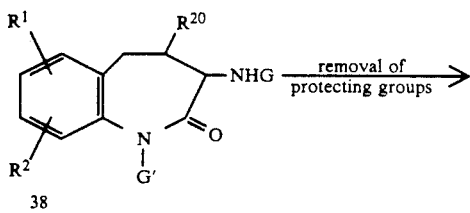
38

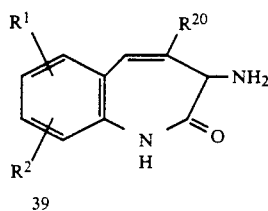
39

C-4, C-5 disubstituted analogs 42 can be prepared from the aforementioned intermediate 36 by addition of the Grignard $R^{21}$—MgBr, followed by dehydration and liberation of protecting groups.

SCHEME 9

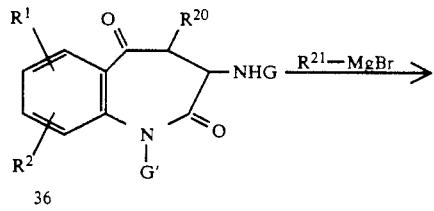
36

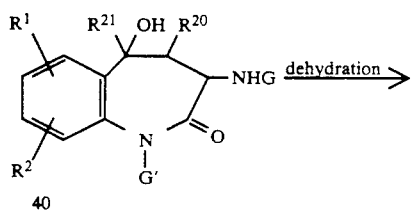
40

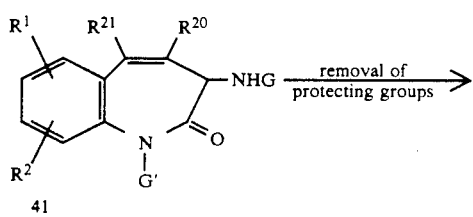
41

-continued
SCHEME 9

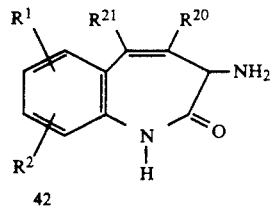
42

The sub-class of compounds of formula I wherein X is —SCH($R^{20}$)— and $R^{20}$ is a substituted phenyl residue is prepared by the method of H. Kugita, et al, as described in Chem. Pharm. Bull., 19, 595–602 (1971), and illustrated in Scheme 10. Reaction of the epoxide 44 with the 2-nitro-thiophenol derivative 43 gives hydroxy-ester 45 which is reduced and cyclized under basic conditions to generate the benzothiazepinone compound 47. Formation of the O-methanesulfonate derivative, followed by displacement with azide and reduction with triphenylphosphine gives the 3-aminobenzothiazepinone compound 49.

SCHEME 10

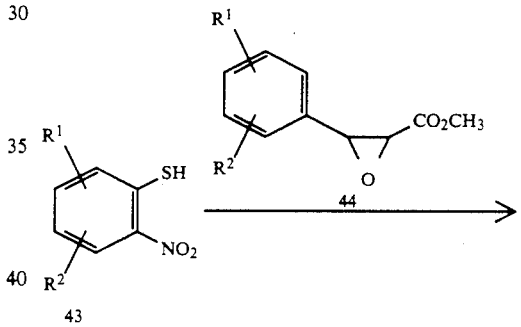
43    44

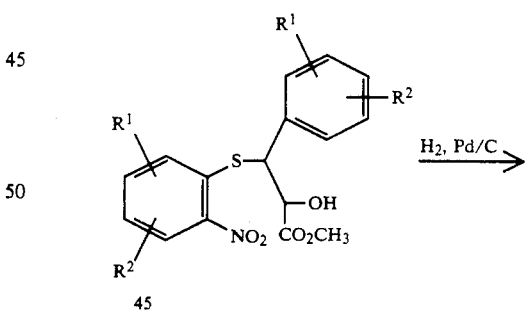
45

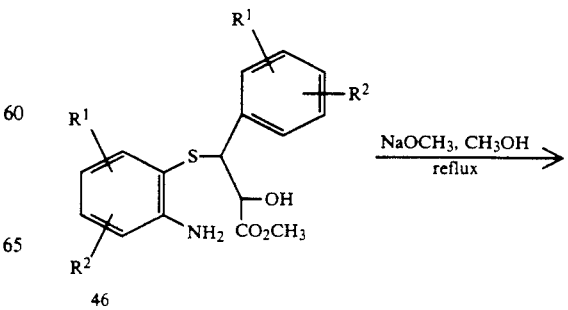
46

-continued
SCHEME 10

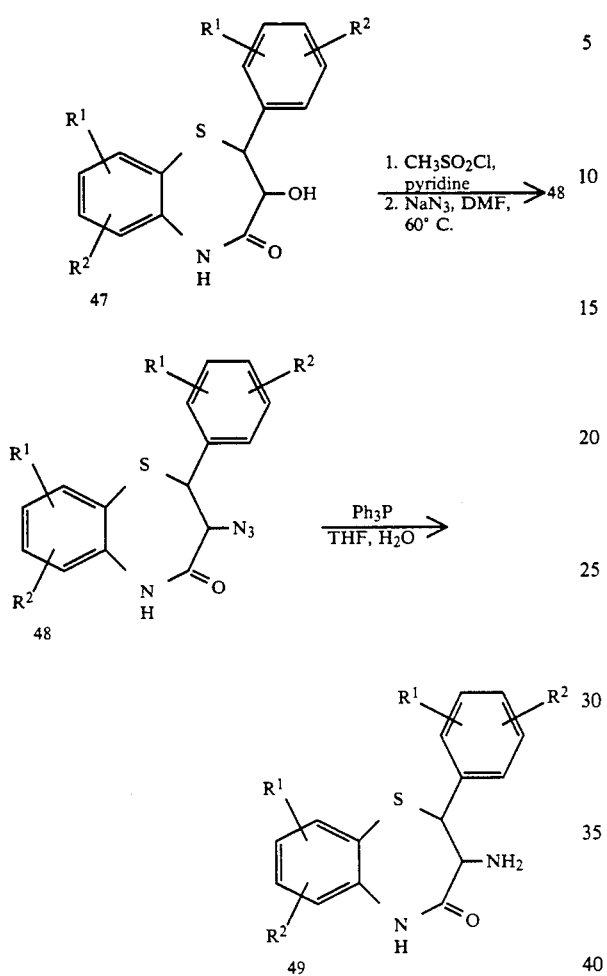

A similar route, shown in Scheme 11, may be envisioned for the analogous 3-amino-oxazepine intermediate 56, starting from a suitably substituted derivative of 2-nitro phenol 50.

SCHEME 11

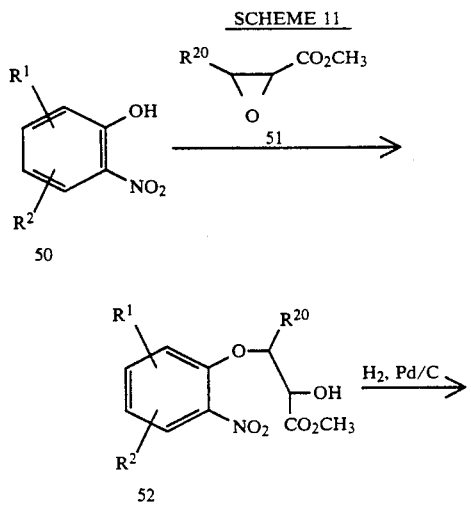

-continued
SCHEME 11

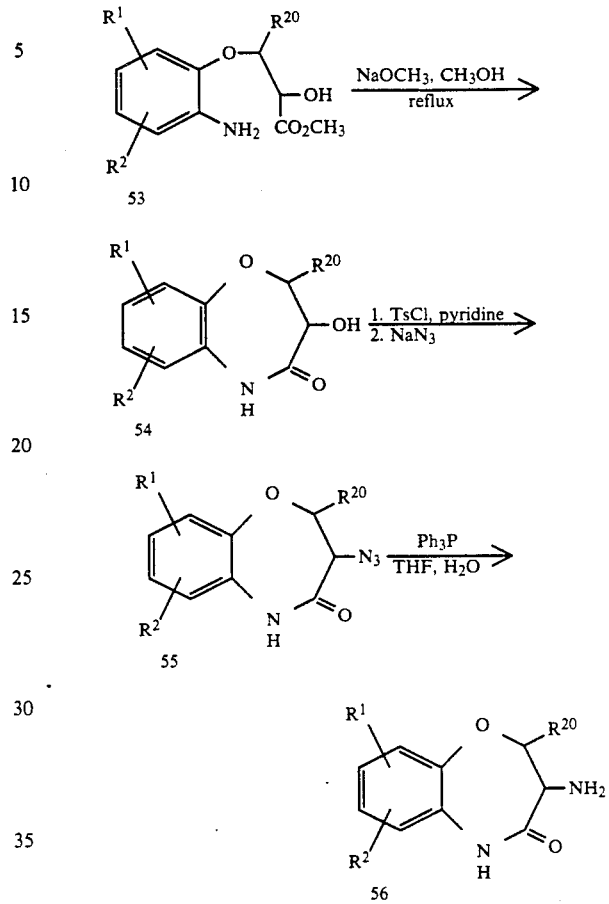

Chiral aminobenzolactams are obtained by resolution of the racemates by classical methods familiar to those skilled in the art. For example, resolution can be achieved by formation of diastereomeric salts of the racemic amines with optically active acids such as D- and L-tartaric acid. Determination of absolute stereochemistry can be achieved in a number of ways including X-ray analysis of a suitable crystalline derivative.

Intermediates of formula II can be further elaborated to new intermediates (formula III) which are substituted on the amino group (Scheme 12). Reductive alkylation of II with an aldehyde is carried out under conditions known in the art; for example, by catalytic hydrogenation with hydrogen in the presence of platinum, palladium or nickel catalysts or with chemical reducing agents such as sodium cyanoborohydride in an inert solvent such as methanol or ethanol.

SCHEME 12

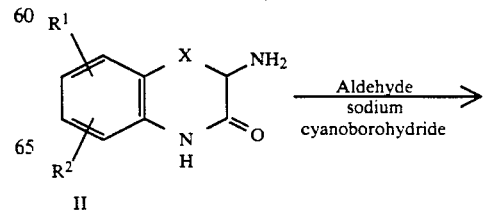

SCHEME 12 -continued

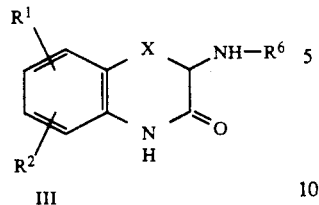

III

Attachment of the amino acid sidechain to intermediates of formula III is accomplished by the route shown in Scheme 13. coupling is conveniently carried out by the use of an appropriately protected amino acid derivative, such as that illustrated by formula IV, and a coupling reagent such as benzotriazol-1-yloxytris(dimethylamino)phosphonium hexafluorophosphate ("BOP") in an inert solvent such as methylene chloride. Separation of unwanted side products, and purification of intermediates is achieved by chromatography on silica gel, employing flash chromatography (W. C. Still, M. Kahn and Mitra, J. Org. Chem., 43, 2923 (1978)) or by medium pressure liquid chromatography.

SCHEME 13

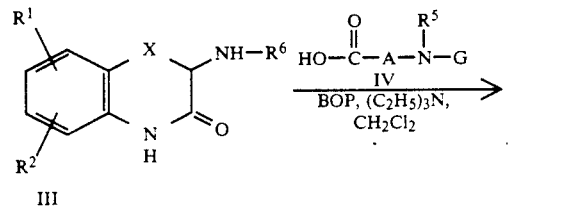

G = t-butoxycarbonyl or benzyloxycarbonyl

The protected amino acid derivatives IV are, in many cases, commercially available in t-butoxycarbonyl (BOC) or benzyloxycarbonyl (CBz) forms. A useful method to prepare the preferred sidechain 61 is shown in Scheme 14.

SCHEME 14

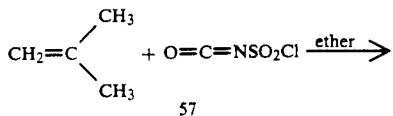

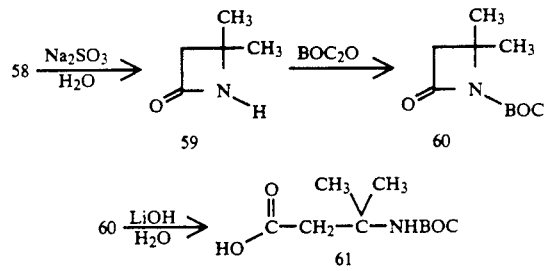

Reaction of isobutylene with N-chlorosulfonylisocyanate 57 in diethyl ether gives the azetidinone derivative 58. Removal of the chlorosulfonyl group with aqueous sodium sulfite followed by reaction with di-t-butyl-dicarbonate gives the BOC-protected intermediate 60. Alkaline hydrolysis gives the protected amino acid derivative 61 in good overall yield.

Intermediates of formula VII can be prepared as shown in Scheme 15 by treatment of the desired lactam intermediate V with an alkylating agent VI, wherein L is a good leaving group such as Cl, Br, I, O-methanesulfonyl or O-(p-toluenesulfonyl). Alkylation of intermediates of formula V is conveniently carried out in anhydrous dimethyl formamide (DMF) in the presence of bases such as sodium hydride or potassium t-butoxide for a period of 0.5 to 24 hours at temperatures of 20°-100° C. Substituents on the alkylating agent VI may need to be protected during alkylation. A description of such protecting groups may be found in: *Protective Groups in Organic Synthesis*, T. W. Greene, John Wiley and Sons, New York, 1981.

SCHEME 15

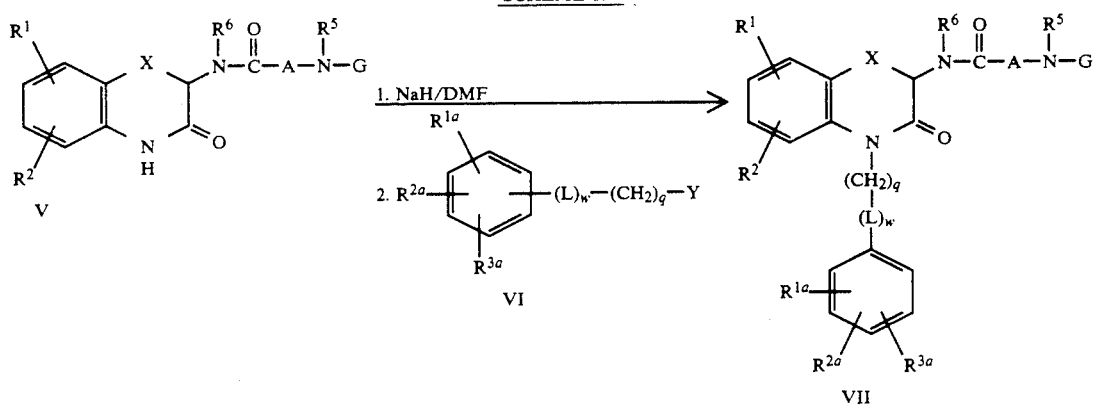

Y is a leaving group

-continued
SCHEME 15

G is t-butoxycarbonyl or benzyloxycarbonyl

Alkylating agents VI are, in some cases commercially available compounds or may be prepared as described in EPO publications 253,310; 291,969; 324,377 and the referenced cited therein.

Compounds of formula I wherein $R^{3a}$ or $R^{3b}$ is a tetrazole (64) are prepared as described in Scheme 16 by alkylation of V with a suitably substituted alkylating agent 62 containing a nitrile as tetrazole precursor. Elaboration to the desired product 64 is carried out by treatment with trimethyltin azide in boiling toluene.

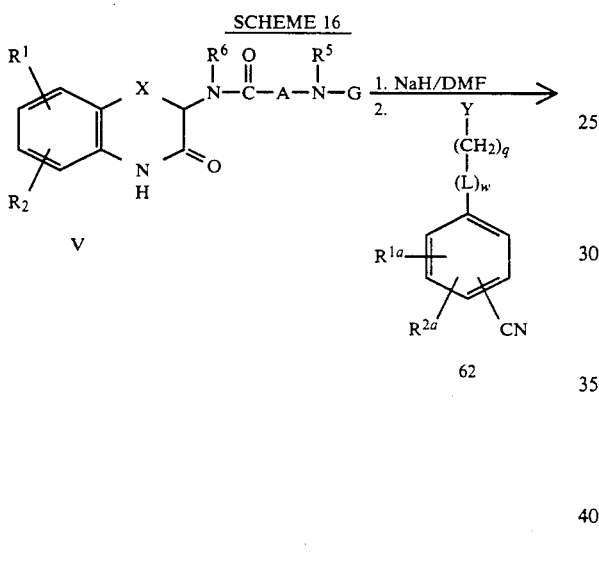

G = t-butoxycarbonyl or benzyloxycarbonyl
Y is a leaving group

A useful method to prepare the preferred alkylating agent 69 is shown in Scheme 17, and in U.S. Pat. No. 5,039,814.

SCHEME 17

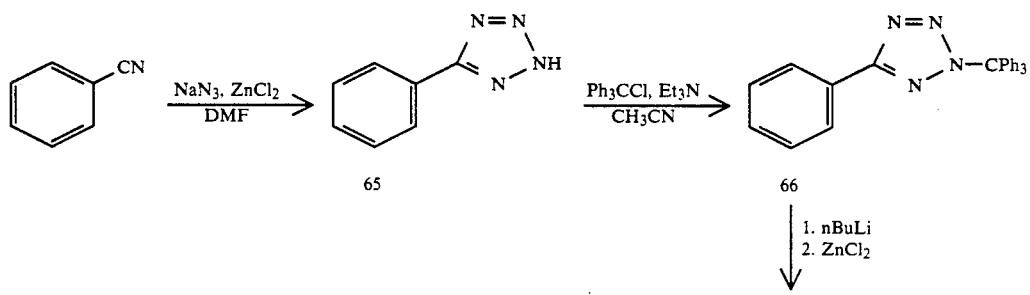

-continued
SCHEME 17

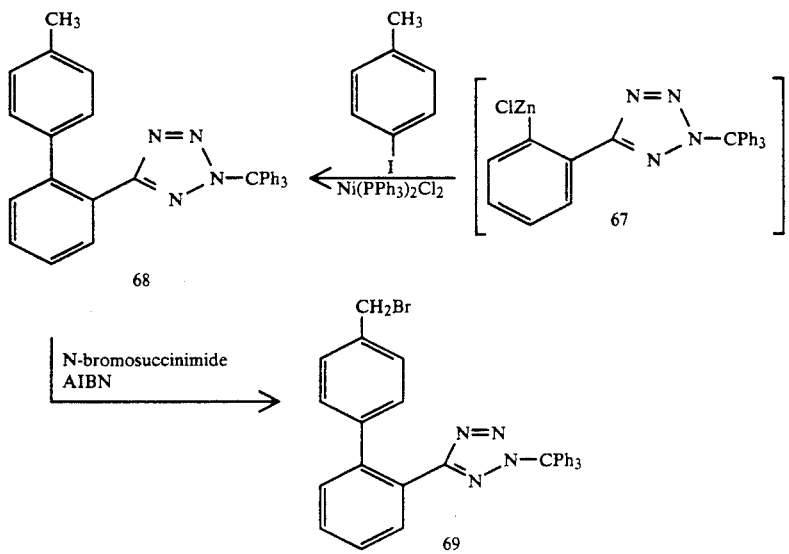

As outlined in Scheme 17, benzonitrile is treated with sodium azide and zinc chloride to give 5-phenyltetrazole 65 which is converted to the N-trityl derivative 66 by treatment with triphenylmethyl chloride and triethylamine. The zinc reagent 67 was prepared by treatment with n-butyl lithium followed by zinc chloride. Coupling with 4-iodotoluene using the catalyst bis(triphenylphosphine)nickel(II) dichloride gives the biphenyl product 68 high yield. Reaction with N-bromosuccinimide and AIBN gives bromide 69.

Compounds of Formula I wherein $R^{3a}$ or $R^{3b}$ are taken as $R^4R^5CNO(CH_2)_v$ and v is 0 can be prepared by several methods. For example, as shown in Scheme 18, compound 70 wherein $R^4$ and $R^5$ are both hydrogen is conveniently prepared by hydrolysis of a nitrile precursor 63.

SCHEME 18

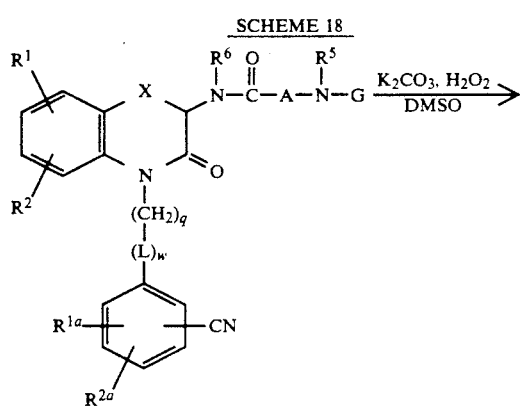

63

-continued
SCHEME 18

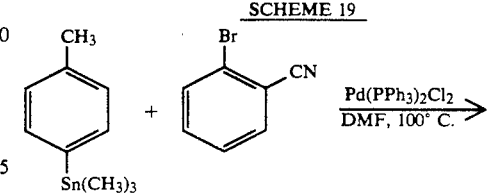

70

Thus, treatment of the nitrile 63 with hydrogen peroxide and a strong base, such as potassium carbonate, in a polar solvent, such as dimethylsulfoxide at temperatures of 25° C. to 150° C. results in formation of the amide derivative 70.

A useful method of preparing the alkylating agent 73 is outlined in Scheme 19.

SCHEME 19

71

SCHEME 19 -continued

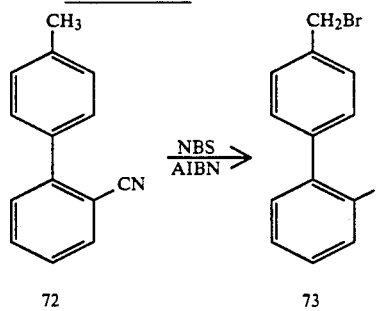

Thus, treatment of 4-(methylphenyl)trimethyl stannane 71 with 2-bromobenzonitrile in dimethylformamide at 100° C. in the presence of bis-triphenylphosphine palladium (II) chloride results in coupling to form the biphenyl nitrile 72 in high yield. Conversion to bromide 73 is achieved by treatment with N-bromosuccinimide and a radical initiator, such as azobisisobutyronitrile (AIBN), in refluxing carbon tetrachloride.

Compounds of Formula I wherein $R^{3a}$ or $R^{3b}$ are taken as $R^4R^5NCO(CH_2)_v$ and v is 0 and $R^4$ and/or $R^5$ are not hydrogen are prepared from the corresponding carboxylic acid derivatives 74 as shown in Scheme 20.

SCHEME 20

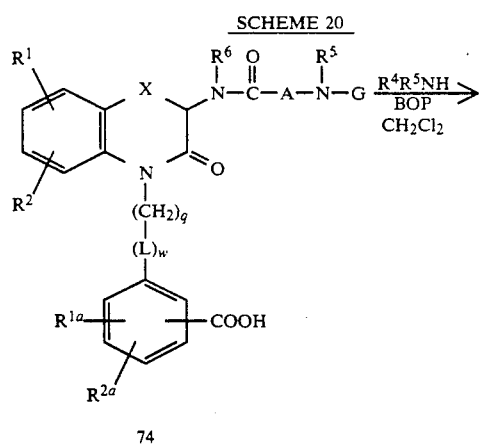

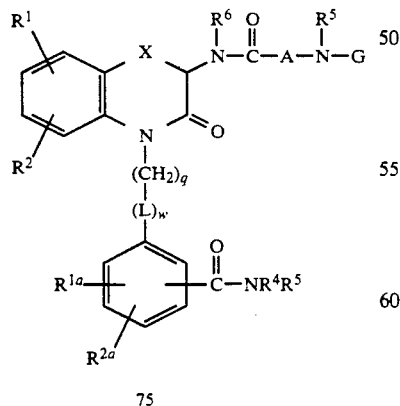

Coupling of the carboxylic acid derivative 74 with $R^4R^5NH$ is conveniently carried out by the use of a coupling reagent such as benzotriazol-1-yloxytris(dimethylamino)phosphonium hexafluorophosphate ("BOP") in an inert solvent such as methylene chloride.

The requisite carboxylic acid precursors can be prepared as illustrated in Scheme 21 for the biphenyl compound 74.

SCHEME 21

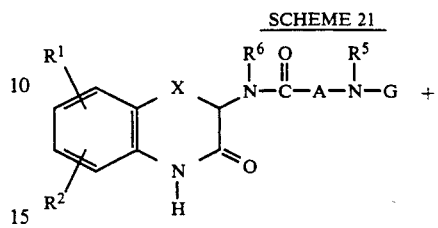

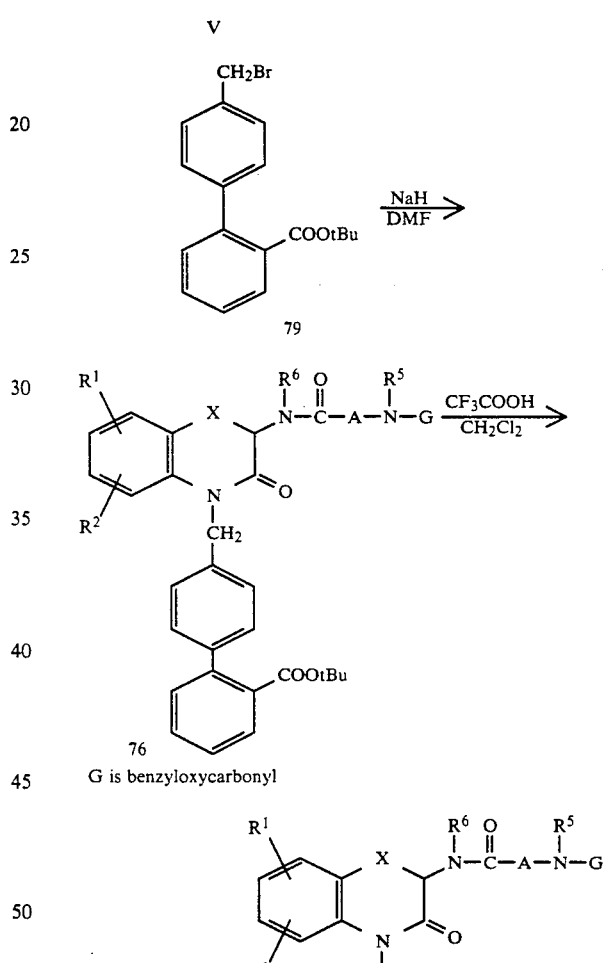

G is benzyloxycarbonyl

A convenient method to prepare the useful alkylating agent 79 is shown in Scheme 22. Metallation of 4-iodotoluene with t-butyllithium in tetrahydrofuran, followed by treatment with zinc chloride gives the intermediate zinc reagent 77. Coupling of 77 with t-butyl 2-bromobenzoate in presence of bis(triphenylphosphine)nickel(II) chloride affords the biphenyl product 78 in high yield. Bromination to give the desired intermediate 79 is carried out under the aforementioned conditions.

SCHEME 22

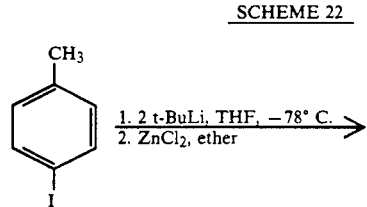

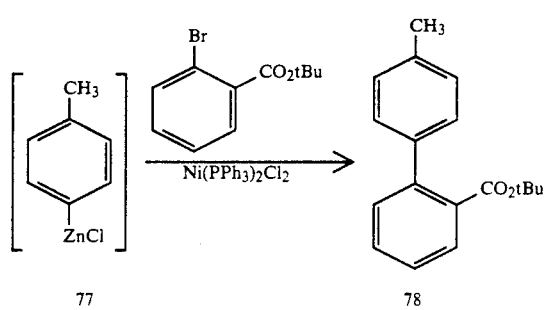

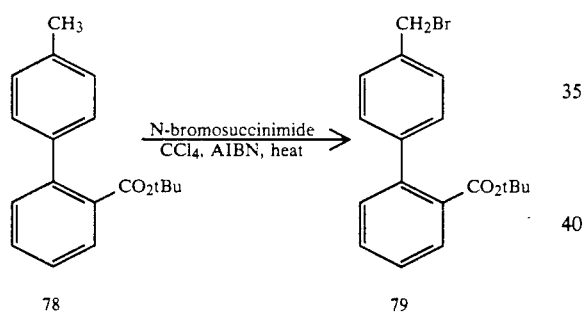

Compounds of formula I where $R^{3a}$ or $R^{3b}$ is a carbamate, semicarbazide or urea derivative, wherein this functionality is attached to the phenyl ring by a nitrogen atom are prepared from intermediates 80, obtained by alkylation with a derivative of formula VI wherein $R^{3a}$ or $R^{3b}$ is a nitro group as shown in Scheme 23.

SCHEME 23

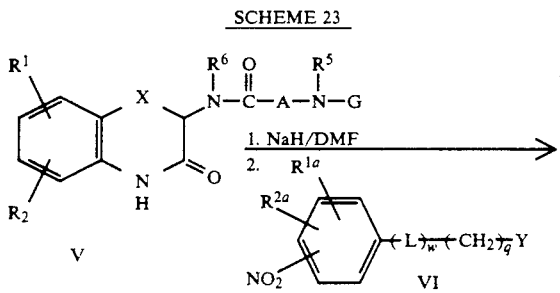

-continued
SCHEME 23

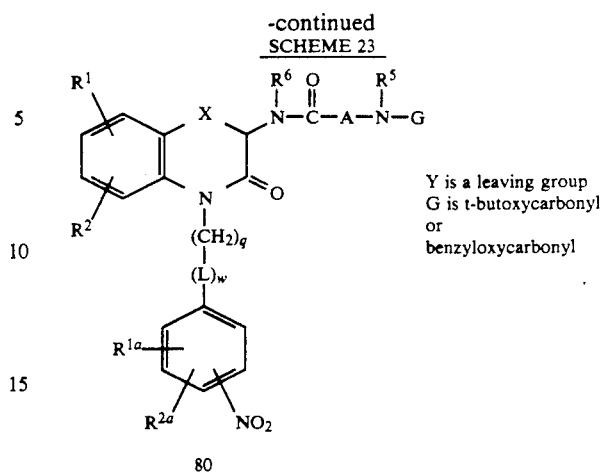

Y is a leaving group
G is t-butoxycarbonyl or benzyloxycarbonyl

A useful method of synthesizing the preferred alkylating agent 84 is shown in reaction Scheme 24.

SCHEME 24

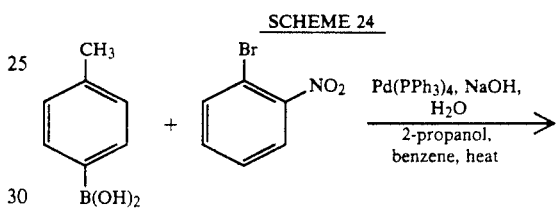

Reaction of 4-tolylboronic acid 81 with 2-bromonitrobenzene 82 in the presence of a transition metal catalyst such as (tetrakis)triphenylphosphine palladium (0) in a mixed solvent system containing aqueous sodium hydroxide, water, 2-propanol and benzene at elevated temperatures for several hours gives the coupled product 83 in good overall yield. Chromatographic purification and separation of unwanted by-products is conveniently performed on silica, eluting with common organic solvents such as hexane, ethyl acetate and methylene chloride. Conversion of 83 to the bromide derivative 84 is accomplished by treatment with N-bromosuccinimide in refluxing carbon tetrachloride in the presence of a radical initiator such as benzoyl peroxide or 2,2-azobisisobutyronitrile (AIBN).

As shown in Scheme 25, reduction of the nitro group of 80 is achieved by hydrogenation in the presence of a metal catalyst, such as palladium on carbon, in a protic solvent such as methanol or ethanol. It may be appreciated by one skilled in the art that for certain compounds where catalytic hydrogenation is incompatible with existing functionality, alternative methods of reduction are indicated, such as chemical reduction with stannous chloride under acidic conditions. It should also be noted that the protecting group G in intermediate 80 must be compatible with the experimental conditions anticipated for reduction. For example, intermediates 80 wherein G is t-butoxycarbonyl (BOC) are stable to the conditions of catalytic reduction employed in the conversion to 85. Intermediates 85 may also be further elaborated to new intermediates 86 by reductive alkylation with an aldehyde by the aforementioned procedures.

SCHEME 25

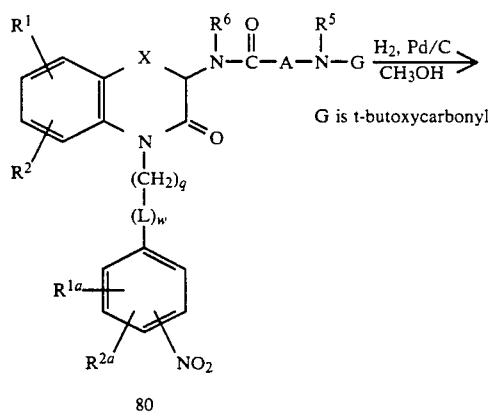

80

-continued
SCHEME 25

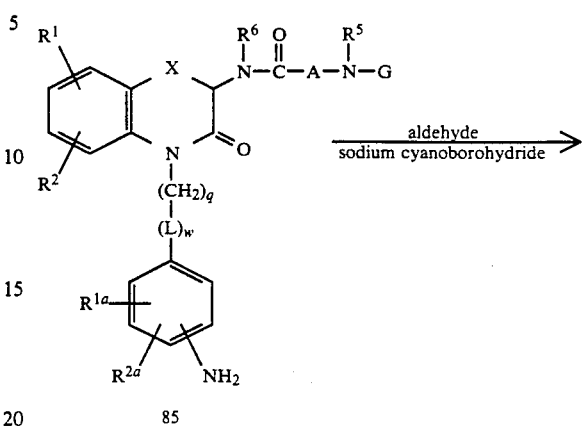

85

86

Elaboration of 86 to carbamate compounds is achieved by reaction with the appropriate chloroformate reagent in pyridine or in methylene chloride with triethylamine as shown in Scheme 26.

SCHEME 26

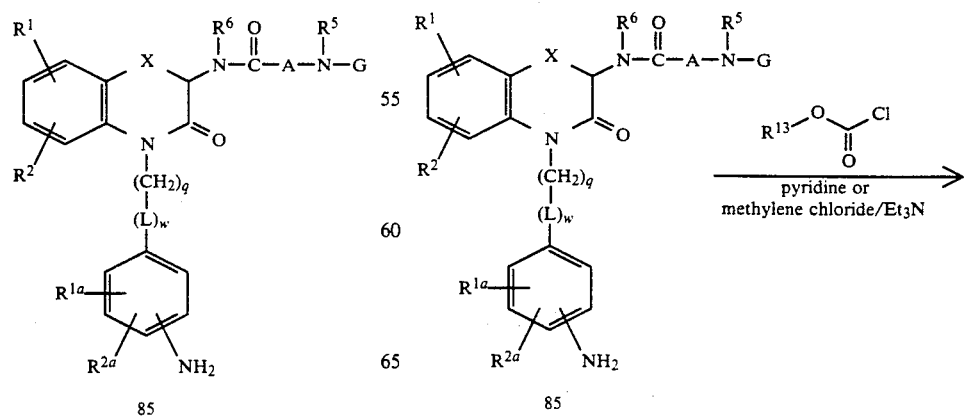

85

-continued
SCHEME 26

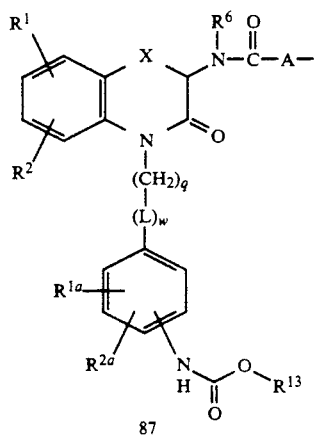

87

Transformation of amine intermediate 85 to urea derivatives is accomplished in several ways. Terminally disubstituted compounds 88 can be obtained directly by reaction of 85 with a disubstituted carbamoyl chloride in an inert solvent such as methylene chloride in the presence of triethylamine or 4-dimethylaminopyridine. In addition, monosubstituted compounds 89 wherein either $R^{4b}$ or $R^{12a}$ is hydrogen are obtained from 85 by reaction with an isocyanate as shown in Scheme 27.

SCHEME 27

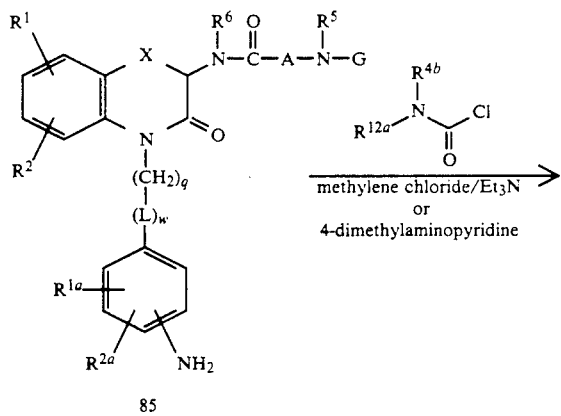

85

88

-continued
SCHEME 27

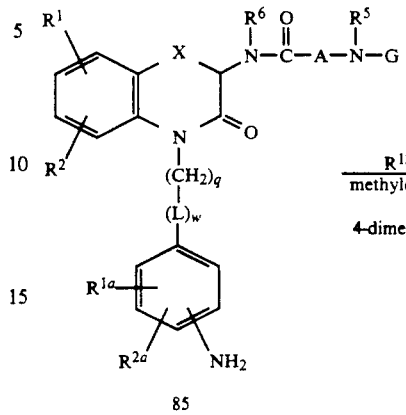

85

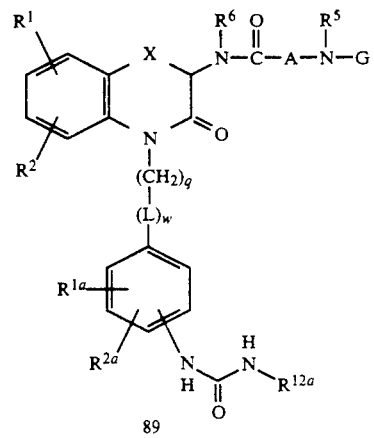

89

Alternatively, amine 85 is converted to an isocyanate 90 by treatment with phosgene or an equivalent reagent such as bis(trichloromethyl)carbonate (triphosgene) as indicated in Scheme 28. Subsequent reaction of with primary or secondary amines in an inert solvent such as methylene chloride gives the corresponding urea derivates 91 in good yield. Isocyanate 90 is also converted to substituted semicarbazides 92 or hydroxy- or alkoxyureas 93 by reaction with substituted hydrazines or hydroxy- or alkoxylamines, respectively.

SCHEME 28

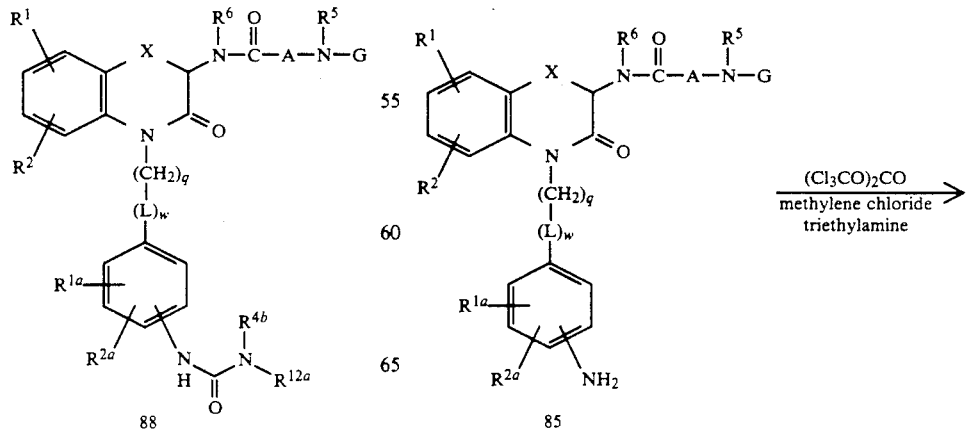

85

-continued
SCHEME 28
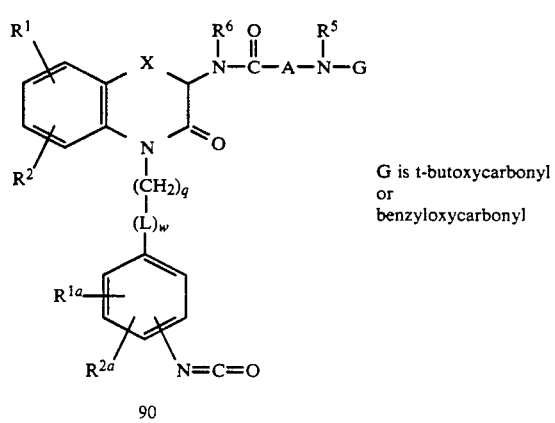
90
G is t-butoxycarbonyl or benzyloxycarbonyl
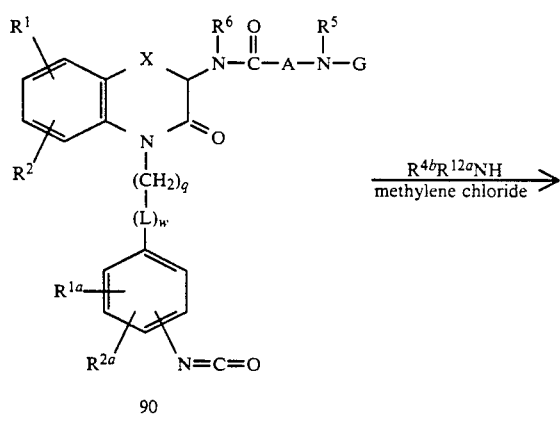
90
$\xrightarrow{R^{4b}R^{12a}NH}_{\text{methylene chloride}}$
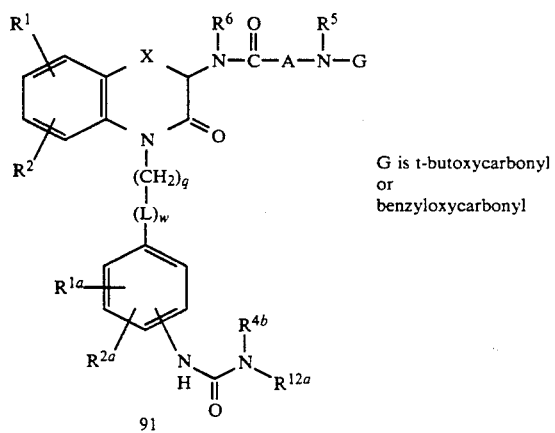
91
G is t-butoxycarbonyl or benzyloxycarbonyl
-continued
SCHEME 28
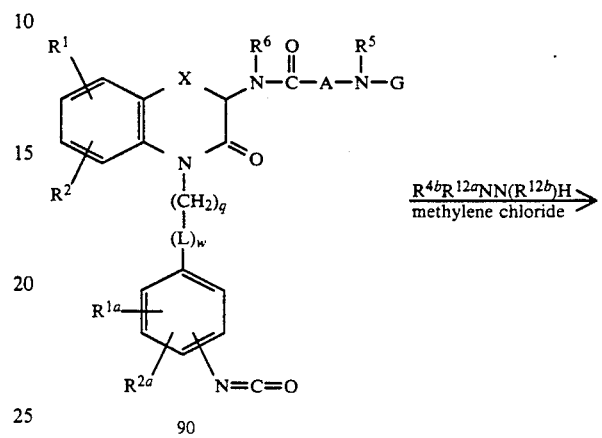
90
$\xrightarrow{R^{4b}R^{12a}NN(R^{12b})H}_{\text{methylene chloride}}$
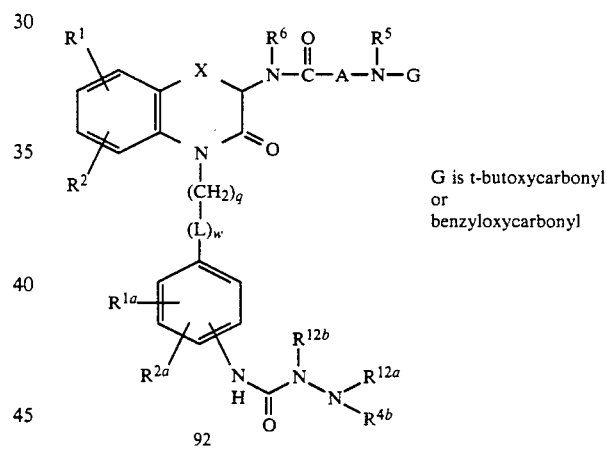
92
G is t-butoxycarbonyl or benzyloxycarbonyl
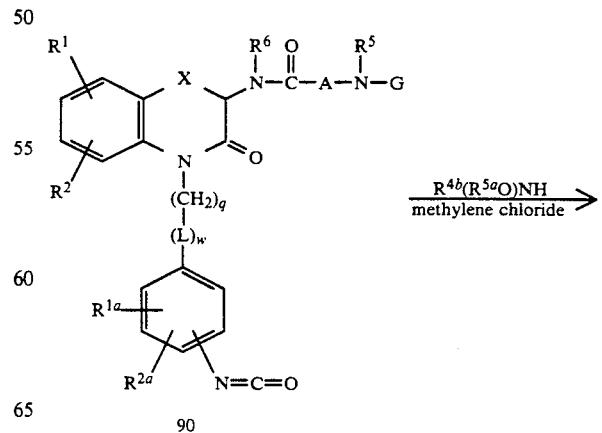
90
$\xrightarrow{R^{4b}(R^{5a}O)NH}_{\text{methylene chloride}}$ -continued
SCHEME 28

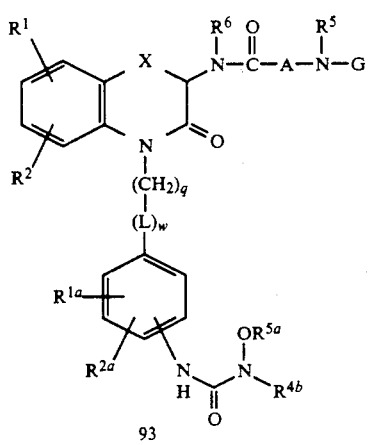
93

G is t-butoxycarbonyl
or
benzyloxycarbonyl

Compounds of formula I where $R^{3a}$ or $R^{3b}$ is a carbazate or carbamate derivative where attachment to the phenyl ring is through the oxygen atom of the carbazate or carbamate linkage are prepared from acetophenone intermediates 94 as indicated in Scheme 29.

SCHEME 29

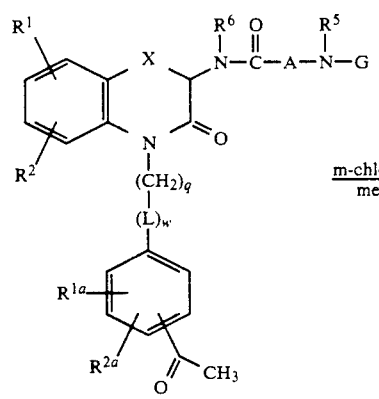
94

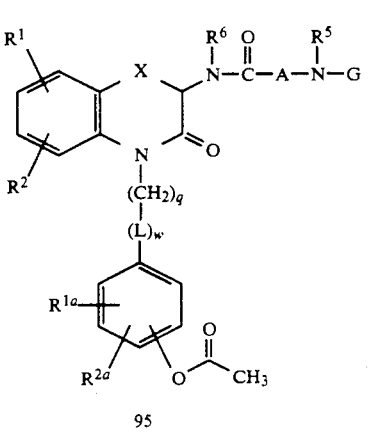
95

-continued
SCHEME 29

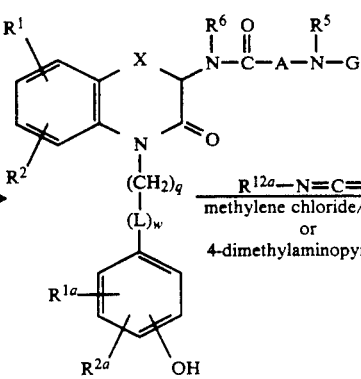
96

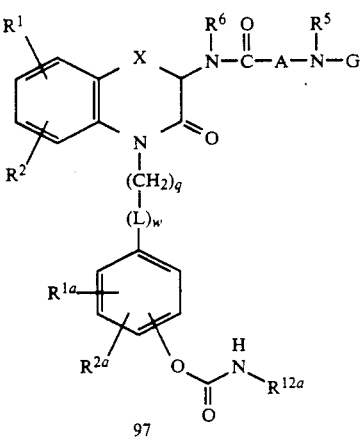
97

G is t-butoxycarbonyl
or
benzyloxycarbonyl

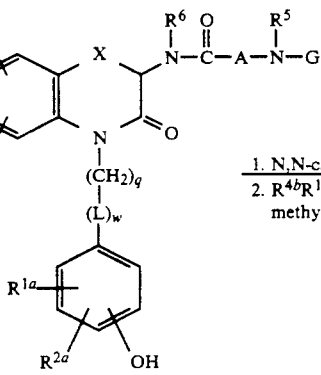
96

-continued
SCHEME 29

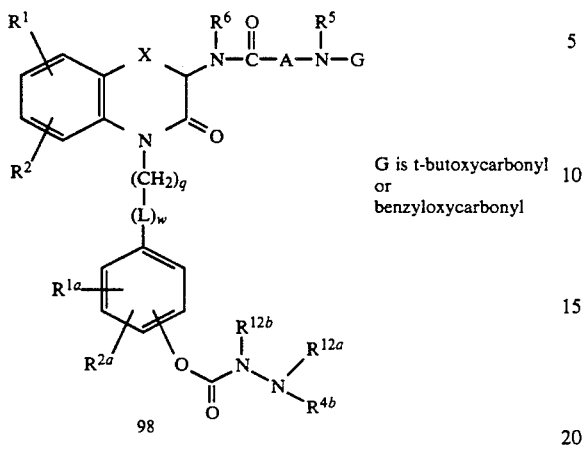

G is t-butoxycarbonyl or benzyloxycarbonyl

Oxidative rearrangement of 94 through the use of a peroxy-carboxylic acid (Baeyer-Villager reaction) such as m-chloroperbenzoic acid gives the ester 95 which is hydrolyzed in the presence of a strong base such as sodium or lithium hydroxide to give phenol 96.

Reaction of 96 with an isocyanate leads directly to carbamate analogs 97. Additionally, treatment of 96 with N,N'-carbonyldiimidazole in dimethylformamide can form an activated intermediate which will react with substituted hydrazine reagents to give carbazate products 98.

Compounds of formula I wherein $R^{3a}$ or $R^{3b}$ contains the linkage $-CH_2N(R^{12b})-$ can be prepared from the t-butyl ester intermediate 76 as described in Scheme 30. Removal of the t-butyl ester through the use of trifluoroacetic acid gives the carboxylic acid 74. It may be appreciated by one skilled in the art that the protecting group G in 76 must therefore be compatible with the strongly acidic conditions employed for ester cleavage, hence G is taken as benzyloxycarbonyl. Conversion of the carboxylic acid to the benzylamine derivative can be achieved by a five-step sequence consisting of: 1) formation of a mixed anhydride with isobutyl chloroformate; 2) reduction with sodium borohydride to the benzyl alcohol; 3) formation of the mesylate with methanesulfonyl chloride; 4) formation of the azide by reaction with sodium azide, and finally, 5) reduction of the azide with tin(II) chloride. The benzylamine intermediate can be further elaborated to 100 by the aforementioned reductive amination procedure.

SCHEME 30

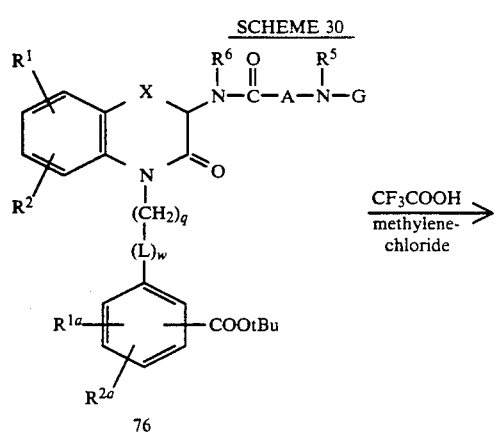

$\xrightarrow{CF_3COOH}{\text{methylene-chloride}}$

-continued
SCHEME 30

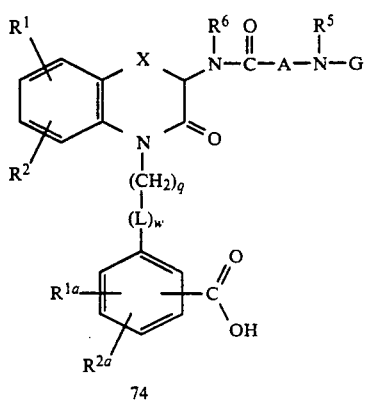

1. iBu—O—C(=O)—Cl, N-methylmorpholine
2. sodium borohydride
3. CH$_3$SO$_2$Cl
4. sodium azide
5. SnCl$_2$, aqueous dioxane

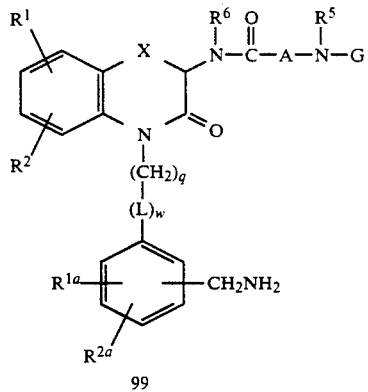

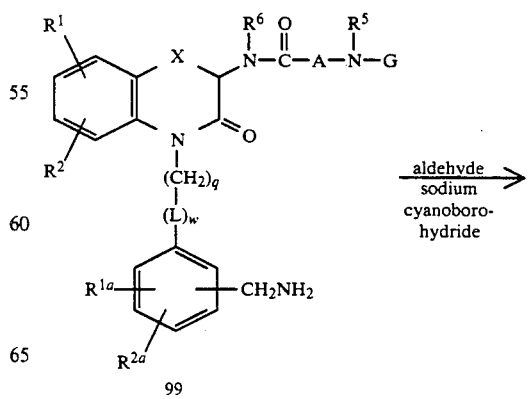

$\xrightarrow[\text{sodium cyanoborohydride}]{\text{aldehyde}}$

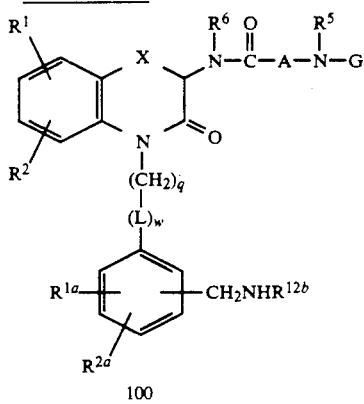
100
G is benzyloxycarbonyl
Reaction of amine 100 with the appropriate reagents to form urea-linked compounds 101 and 102 carbamate-linked compounds 103, and amide-linked structures 104 are illustrated in Scheme 31.
SCHEME 31
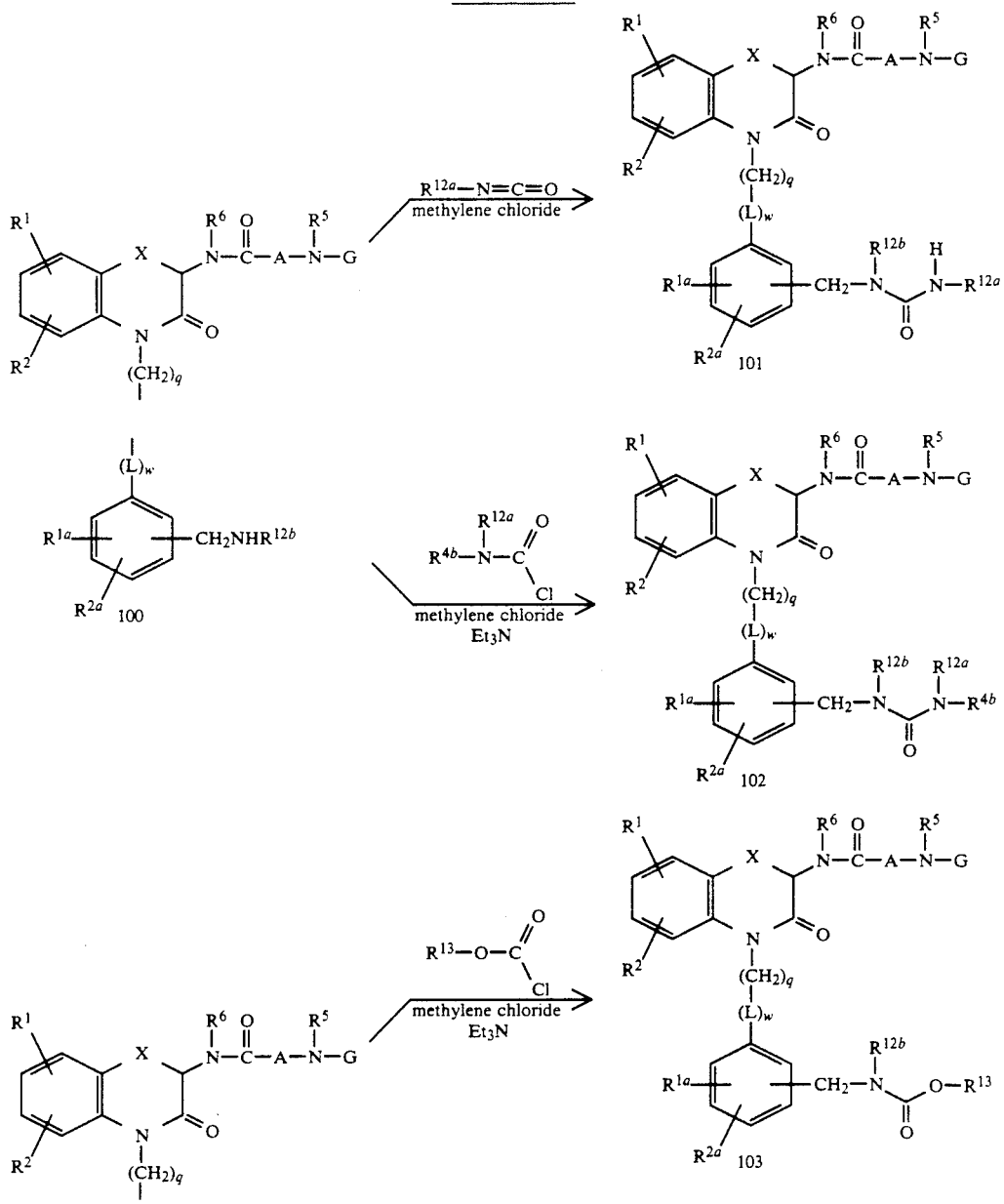

SCHEME 31

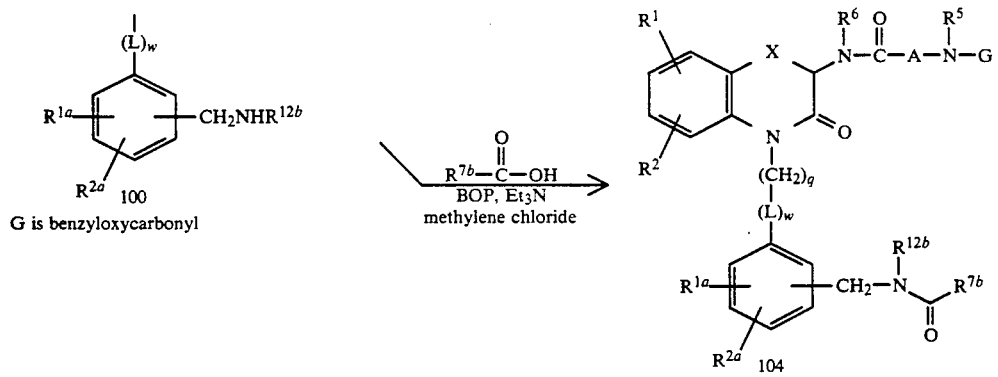

G is benzyloxycarbonyl

A useful preparation of the protected benzylamine intermediate 109 is shown in Scheme 32. Metallation of 4-bromobenzyl t-butyldimethylsilylether 105 with n-butyllithium followed by treatment with trimethyl borate gives the aryl boronic acid 106. Reaction of 106 with 2-bromo-N-(t-butoxycarbonyl)benzylamine 107 in the presence of tetrakis(triphenylphosphine)palladium(O) and barium hydroxide in aqueous 1,2-dimethoxyethane at elevated temperature gives the coupled product 108 in good yield. Desilylation is carried out by treatment with tetra-n-butylammonium fluoride; conversion to the O-methanesulfonate 109 is achieved by reaction of the intermediate benzyl alcohol with methanesulfonic anhydride. Reaction of 109 with compounds of formula V is carried out using the conditions described in Scheme 15.

SCHEME 32

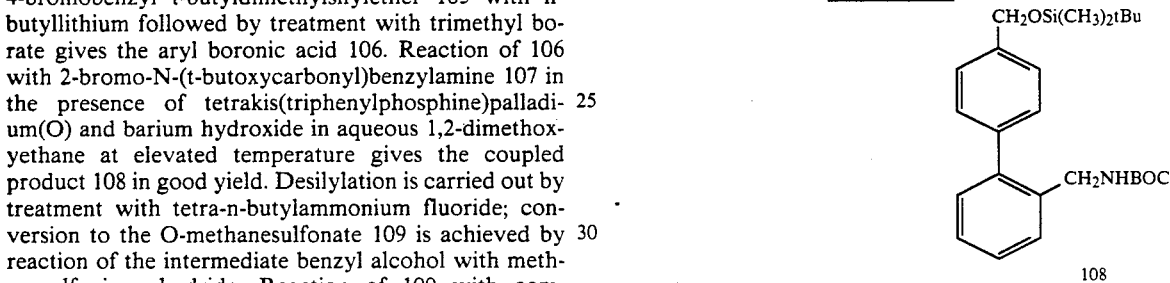

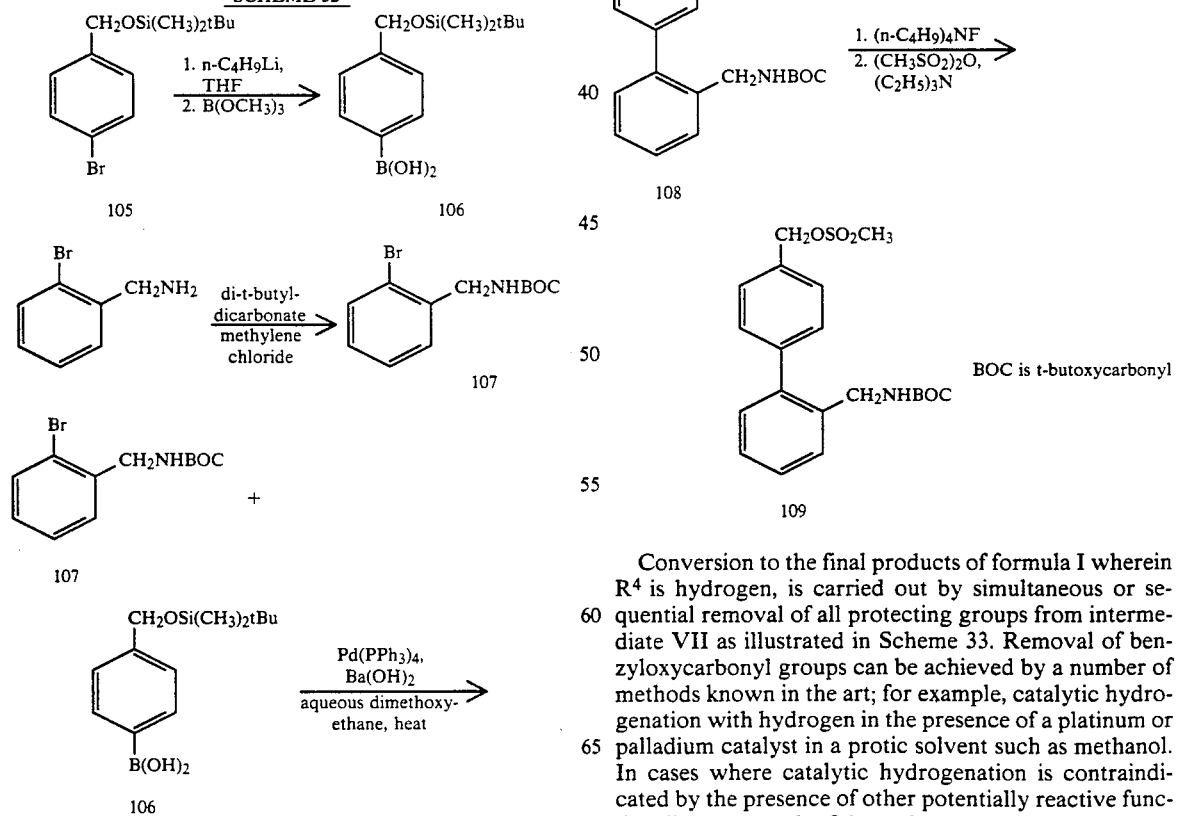

BOC is t-butoxycarbonyl

Conversion to the final products of formula I wherein $R^4$ is hydrogen, is carried out by simultaneous or sequential removal of all protecting groups from intermediate VII as illustrated in Scheme 33. Removal of benzyloxycarbonyl groups can be achieved by a number of methods known in the art; for example, catalytic hydrogenation with hydrogen in the presence of a platinum or palladium catalyst in a protic solvent such as methanol. In cases where catalytic hydrogenation is contraindicated by the presence of other potentially reactive functionality, removal of benzyloxycarbonyl groups can also be achieved by treatment with a solution of hydrogen bromide in acetic acid. Catalytic hydrogenation is also employed in the removal of N-triphenylmethyl (trityl) protecting groups. Removal of t-butoxycarbonyl (BOC) protecting groups is carried out by treatment of a solution in a solvent such as methylene chloride or methanol, with a strong acid, such as hydrochloric acid or trifluoroacetic acid. Conditions required to remove other protecting groups which may be present can be found in *Protective Groups in Organic Synthesis*.

SCHEME 33

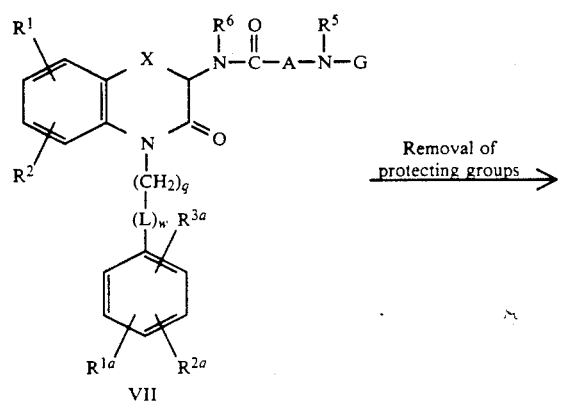

Compounds of formula I wherein $R^4$ and $R^5$ are each hydrogen can be further elaborated by reductive alkylation with an aldehyde by the aforementioned procedures or by alkylations such as by reaction with various epoxides as shown in Scheme 34. The products, obtained as hydrochloride or trifluoroacetate salts, are conveniently purified by reverse phase high performance liquid chromatography (HPLC) or by recrystallization.

SCHEME 34

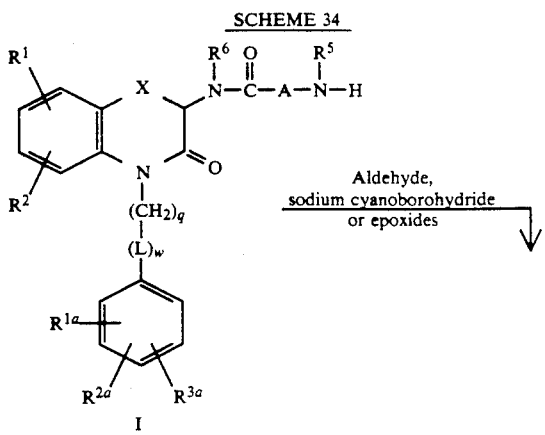

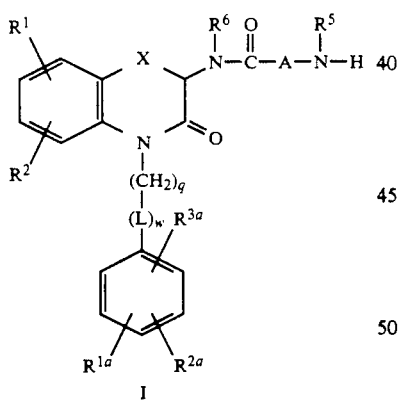

It is noted that the order of carrying out the foregoing reaction schemes is not significant and it is within the skill of one skilled in the art to vary the order of reactions to facilitate the reaction or to avoid unwanted reaction products.

The growth hormone releasing compounds of Formula I are useful in vitro as unique tools for understanding how growth hormone secretion is regulated at the pituitary level. This includes use in the evaluation of many factors thought or known to influence growth hormone secretion such as age, sex, nutritional factors, glucose, amino acids, fatty acids, as well as fasting and non-fasting states. In addition, the compounds of this invention can be used in the evaluation of how other hormones modify growth hormone releasing activity. For example, it has already been established that somatostatin inhibits growth hormone release. Other hormones that are important and in need of study as to their effect on growth hormone release include the gonadal hormones, e.g., testosterone, estradiol, and progesterone; the adrenal hormones, e.g., cortisol and other corticoids, epinephrine and norepinephrine; the pancreatic and gastrointestinal hormones, e.g., insulin, glucagon, gastrin, secretin; the vasoactive intestinal peptides, e.g., bombesin; and the thyroid hormones, e.g., thyroxine and triiodothyronine. The compounds of Formula I can also be employed to investigate the possible negative or positive feedback effects of some of the pituitary hormones, e.g., growth hormone and endorphin peptides, on the pituitary to modify growth hormone release. Of particular scientific importance is the use of these compounds to elucidate the subcellular mechanisms mediating the release of growth hormone.

The compounds of Formula I can be administered to animals, including man, to release growth hormone in vivo. For example, the compounds can be administered to commercially important animals such as swine, cattle, sheep and the like to accelerate and increase their rate and extent of growth, and to increase milk production in such animals. In addition, these compounds can be administered to humans in vivo as a diagnostic tool to directly determine whether the pituitary is capable of releasing growth hormone. For example, the compounds of Formula I can be administered in vivo to children. Serum samples taken before and after such administration can be assayed for growth hormone. Comparison of the amounts of growth hormone in each of these samples would be a means for directly determining the ability of the patient's pituitary to release growth hormone.

Accordingly, the present invention includes within its scope pharmaceutical compositions comprising, as an active ingredient, at least one of the compounds of Formula I in association with a pharmaceutical carrier or diluent. Optionally, the active ingredient of the pharmaceutical compositions can comprise a growth promoting agent in addition to at least one of the compounds of Formula I or another composition which exhibits a different activity, e.g., an antibiotic or other pharmaceutically active material.

Growth promoting agents include, but are not limited to, TRH, diethylstilbesterol, theophylline, enkephalins, E series prostaglandins, compounds disclosed in U.S. Pat. No. 3,239,345, e.g., zeranol, and compounds disclosed in U.S. Pat. No. 4,036,979, e.g., sulbenox or peptides disclosed in U.S. Pat. No. 4,411,890.

A still further use of the disclosed novel benzo-fused lactam growth hormone secretagogues is in combination with other growth hormone secretagogues such as GHRP-6, GHRP-1 as described in U.S. Pat. Nos. 4,411,890; and publications WO 89/07110 and WO 89/07111 and B-HT920 or growth hormone releasing factor and its analogs or growth hormone and its analogs or somatomedins including IGF-1 and IGF-2.

Additionally, the disclosed novel benzo-fused lactam growth hormone secretagogues can be used in combination with a $\alpha_2$-adrenergic agonists in the treatment of obesity or in combination with parathyroid hormone in the treatment of osteoporosis.

As is well known to those skilled in the art, the known and potential uses of growth hormone are varied and multitudinous. Thus, the administration of the compounds of this invention for purposes of stimulating the release of endogenous growth hormone can have the same effects or uses as growth hormone itself. These varied uses of growth hormone may be summarized as follows: stimulating growth hormone release in elderly humans; Prevention of catabolic side effects of glucocorticoids, treatment of osteoporosis, stimulation of the immune system, treatment of retardation, acceleration of wound healing, accelerating bone fracture repair, treatment of growth retardation, treating renal failure or insufficiency resulting in growth retardation, treatment of physiological short stature, including growth hormone deficient children, treating short stature associated with chronic illness, treatment of obesity and growth retardation associated with obesity, treating growth retardation associated with Prader-Willi syndrome and Turner's syndrome; Accelerating the recovery and reducing hospitalization of burn patients; Treatment of intrauterine growth retardation, skeletal dysplasia, hypercortisolism and Cushings syndrome; Induction of pulsatile growth hormone release; Replacement of growth hormone in stressed patients; Treatment of osteochondrodysplasias, Noonans syndrome, schizophrenia, depression, Alzheimer's disease, delayed wound healing, and psychosocial deprivation; treatment of pulmonary dysfunction and ventilator dependency; Attenuation of protein catabolic response after a major operation; reducing cachexia and protein loss due to chronic illness such as cancer or AIDS. Treatment of hyperinsulinemia including nesidioblastosis; Adjuvant treatment for ovulation induction; To stimulate thymic development and prevent the age-related decline of thymic function; Treatment of immunosuppressed patients; Improvement in muscle strength, mobility, maintenance of skin thickness, metabolic homeostasis, renal hemeostasis in the frail elderly; Stimulation of osteoblasts, bone remodelling, and cartilage growth; Stimulation of the immune system in companion animals and treatment of disorders of aging in companion animals; Growth promotant in livestock; and stimulation of wool growth in sheep.

The compounds of this invention can be administered by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents, They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal or vaginal administration are preferably suppositories which may contain, in addition to the active substance, excipients such as cocoa butter or a suppository wax.

Compositions for nasal or sublingual administration are also prepared with standard excipients well known in the art.

The dosage of active ingredient in the compositions of this invention may be varied; however, it is necessary that the amount of the active ingredient be such that a suitable dosage form is obtained. The selected dosage depends upon the desired therapeutic effect, on the route of administration, and on the duration of the treatment. Generally, dosage levels of between 0.0001 to 100 mg/kg. of body weight daily are administered to patients and animals, e.g., mammals, to obtain effective release of growth hormone.

The following examples are provided for the purpose of further illustration only and are not intended to be limitations on the disclosed invention.

EXAMPLE 1

3-Amino-3-methyl-N--[2,3,4,5-tetrahydro-2-oxo-4-(4-methoxyphenyl)-1-[[2¹-(1H-tetrazol-5-yl)[1,1′-biphenyl]-4-yl]methyl]-1H-1-benzazepin-3-yl]-butanamide, trifluoroacetate

Step A:
2,3,4,5-Tetrahydro-4-(4-methoxyphenyl)-1H-1-benzazepin-2-one

A solution of 1.0 g (3.08 mmol) of 2,3,4,5-tetrahydro-3-(methoxycarbonyl)-4-(4-methoxyphenyl)-1H-1-benzazepin-2-one [prepared by the method of Floyd, et al., J. Med. Chem., 35, 756-772 (1992)]in 10 mL of pyridine was treated with 1.65g (12.3 mmol, 4eq) of lithium iodide and the resulting mixture refluxed in an oil bath under a nitrogen atmosphere for 20 hours. The dark brown mixture was cooled to room temperature and diluted with ethyl acetate. The organic layer was washed with 1N HCl (3×50 mL) and water, dried over anhydrous magnesium sulfate and filtered. Evaporation of the solvent followed by column chromatography on silica gel gave 520mg (63%) of the product. $^1$H NMR (200 MHz, CDCl$_3$): 257 (dd; 4,8 Hz; 2H), 2.81 (dd; 7, 13 Hz; 1H), 3.13 (dd; 8, 14 Hz; 1H), 3.63 (dt; 14, 7 Hz; 1H), 3.74 (s, 3H), 6.82 (d, 8 Hz, 2H), 7.02 (d, 8 Hz, 1H), 7.14–7.34 (m, 5H), 8.03 (br s, 1H). FAB-MS: calculated for C$_{17}$H$_{17}$NO$_2$ 267; found 267 (100%).

Step B:
2,3,4,5-Tetrahydro-3-iodo-4-(4-methoxy-phenyl)-1H-1-benzazepin-2-one To a cooled (−20° C.) solution of 500mg (1.87mmole) of 2,3,4,5-tetrahydro-4-(4-methoxyphenyl)-1H-1-benzazepin-2-one in 10 mL of methylene chloride was added triethylamine (1.04g, 9.35 mmol, 5eq.) followed by trimethylsilyl iodide (749mg, 3.74mmol, 2eq.). After 15 minutes, 950 mg (3,74 mmol, 2eq) of iodine was added and the brown mixture was stirred at 0° C. for one hour. The reaction mixture was diluted with methylene chloride, washed with aqueous sodium bisulfite solution, water and brine and then dried (MgSO$_4$). Filtration followed by evaporation of the solvent under vacuum gave the product as a mixture of cis and trans isomers (675 mg,92%). FAB-MS: calculated for C$_{17}$H$_{16}$NO$_2$I 393; found 393 (100%), 394 (20%).

Step C:
2,3,4,5-Tetrahydro-3-azido-4-(4-methoxyphenyl)-1H-1-benzazepin-2-one A solution of 2,3,4,5-tetrahydro-3-iodo-4-(4-methoxyphenyl)-1H-1-benzazepin-2-one (270 mg, 0.687 mmol) in 2mL of dimethylformamide was treated with sodium azide (65 mg, 1.0 mmol, 1.5eq) and the mixture was heated at 60° C. in an oil bath for 14 hours. The reaction mixture was diluted with ethyl acetate, washed with water and brine, dried (MgSO$_4$) and filtered. Removal of the solvent under vacuum followed by column chromatography on silica gel (eluant 2:1; hexane/ethyl acetate) gave 148 mg (70%) of the product as a single isomer. $^1$H NMR (400 MHz, CDCl$_3$): 295 (dd; 7,14 Hz; 1H), 3.15 (dd; 13, 14 Hz; 1H), 3.75 (m, 1H), 3.80 (s, 3H), 4.11 (d, 7Hz, 1H), 6.89 (d, 8Hz, 2H), 7.04 (d, 8Hz, 1H), 7.20–7.30 (m, 5H), 7.88 (br s, 1H). FAB-MS: calculated for C$_{17}$H$_{16}$N$_4$O$_2$ 308; found 309 (40%).

Step D:
2,3,4,5-Tetrahydro-3-amino-4-(4-methoxyphenyl)-1H-1-benzazepin-2-one A solution of 2,3,4,5-tetrahydro-3-azido-4-(4-methoxyphenyl)-1H-1-benzazepin-2-one (170 mg, 0.552 mmol) in 5 mL of wet tetrahydrofuran was treated with triphenylphosphine (256 mg, 1 mmol, 1.8eq) and the resulting mixture heated at reflux for 6 hours, then cooled to room temperature. The solvent was removed under vacuum and the residue was purified on a silica gel column (eluant 10% MeOH/CH$_2$Cl$_2$) to give the product in quantitative yield. $^1$H NMR (400 MHz, CDCl$_3$): 1.35 (br s, 2H), 2.90 (dd; 6,13 Hz; 1H), 3.05 (dd; 12, 13 Hz; 1H), 3.67 (m, 2H), 3.77 (s, 3H), 6.84 (d, 8Hz, 2H), 7.01 (d, 8 Hz, 1H), 7.13–7.30 (m, 5H), 8.22 (br s, 1H). FAB-MS: calculated for C$_{17}$H$_{18}$N$_2$O$_2$ 282; found 283 (40%).

Step E: 4.4-Dimethylazetidin-2-one

A 3-neck 3L round bottom flask equipped with a magnetic stirrer, thermometer, cold finger condenser and nitrogen bubbler was charged with 1L of ether. The flask was cooled to −65° C. and into it was condensed 500–600 mL of isobutylene. The cold finger condenser was replaced with a dropping funnel and 200 mL (325 g, 2.30 mol) of chlorosulfonyl isocyanate was added dropwise over 1.5 hours. The mixture was maintained at −65° C. for 1.5 hours then the dry ice/acetone cooling bath replaced with methanol/ice and the internal temperature slowly increased to −5° C. at which time the reaction initiated and the internal temperature rose to 15° C. with evolution of gas. The internal temperature remained at 15° C. for several minutes then dropped back down to −5° C. and the mixture stirred at −5° C. for 1 hour. The methanol/ice bath was removed and the reaction mixture warmed to room temperature and stirred overnight.

The reaction mixture was transferred to a 3-neck 12L round bottom flask fitted with a mechanical stirrer and diluted with 2L of ether. The well stirred reaction mixture was treated with 2L of saturated aqueous sodium sulfite. After 1 hour, an additional 1L of saturated aqueous sodium sulfite was added followed by sufficient sodium bicarbonate to adjust the pH to approximately 7. The mixture was stirred another 30 minutes then the layers allowed to separate. The ether layer was removed and the aqueous layer reextracted with 2×1 L of ether. The combined ether extracts were washed once with 500 mL of saturated aqueous sodium bicarbonate and once with 500 mL of saturated aqueous sodium chloride. The ether layer was removed, dried over magnesium sulfate, filtered and concentrated under vacuum to give 33g of a pale yellow oil. The aqueous layer was made basic by the addition of solid sodium bicarbonate and extracted with 3×1 L of ether. The combined ether extracts were washed and dried as described above, then combined with the original 33g of pale yellow oil and concentrated under vacuum to give 67.7g of product. Further extraction of the aqueous layer with 4×1 L of methylene chloride and washing and drying as before gave an additional 74.1 g of product. Still further extraction of the aqueous layer with 4×1 L of methylene chloride gave an additional 21.9g of product. The combined product (163.7g, 1.65 mol, 72%) was used in Step F without purification. $^1$H NMR (200 MHz, CDCl$_3$): 1.45 (s, 6H), 2.75 (d,3Hz, 2H), 5.9 (br s, 1H).

Step F:
N-(t-Butoxycarbonyl)-4,4-dimethylazetidin-2-one

A 5L, 3-neck round bottom flask equipped with a magnetic stirrer, thermometer, nitrogen bubbler and addition funnel was charged with 88.2g (0.89 mol) of 4,4-dimethylazetidin-2-one, 800 mL of methylene chloride, 150 mL of triethylamine (1.08 mol) and 10.9g (0.089 mol) of 4-dimethylaminopyridine. To the stirred solution at room temperature was added dropwise over 15 minutes a solution of 235g (1.077 mol) of di-t-butyldicarbonate in 300 mL of methylene chloride. The reaction mixture was stirred at room temperature overnight then diluted with 1L of methylene chloride and washed with 500 mL of saturated aqueous ammonium chloride, 500 mL of water, and 500 mL of saturated aqueous sodium chloride. The organic layer was separated, dried over magnesium sulfate, filtered and concentrated under vacuum to afford 180.3g of crude product as an orange solid. The material was used directly in Step G without purification.

$^1$H NMR (200 MHz, CDCl$_3$): 1.50 (s,9H), 1.54 (s,6H), 2.77 (s,2H).

Step G: 3-t-Butoxycarbonylamino-3-methylbutanoic acid

A 3L, 3-neck round bottom flask equipped with a magnetic stirrer, thermometer, nitrogen bubbler and addition funnel was charged with 180.3g (0.89 mol) of N-(t-butoxycarbonyl)-4,4-dimethylazetidin-2-one dissolved in 1L of tetrahydrofuran. The solution was cooled to 0°–5° C. and treated dropwise with 890 mL of 1.0M aqueous lithium hydroxide over 30 minutes. The reaction mixture was stirred at 0°–5° C. for 2 hours then diluted with 1L of ether and 1L of water. The layers were allowed to separate and the aqueous layer reextracted with an additional 1L of ether. The aqueous layer was acidified by the addition of 1L of saturated aqueous sodium bisulfate, then extracted with 1×1 L and 2×500 mL of ether. The combined organic layer and ether extracts were washed with 500 mL of saturated aqueous sodium chloride, dried over magnesium sulfate and concentrated under vacuum to 173g of a yellow oil that solidified upon standing. The material was slurried with warm hexane then filtered and dried under high vacuum to afford 168.5g (0.775 mol, 87%) of product as a white solid. $^1$H NMR (200 MHz, CDCl$_3$): 1.39 (s,6H), 1.44 (s,9H), 2.72 (s,2H). FAB-MS: calculated for C$_{10}$H$_{19}$NO$_4$ 217; Found: 218 (M+H,54%).

Step H:
3-t-Butoxycarbonylamino-3-methyl-N-[2,3,4,5-tetrahydro-2-oxo-4-(4-methoxyphenyl)-1H-1-benzazepin-3-yl-butanamide A solution of 150 mg (0.53 mmol) of 2,3,4,5-tetrahydro-3-amino-4-(4-methoxyphenyl)-1H-1-benzazepin-2-one in 2mL of methylene chloride was treated with 127mg (0.58 mmol, 1.1 eq) of 3-t-butoxycarbonylamino-3-methylbutanoic acid and 0.24 mL of triethylamine (175 mg, 1.59 mmol, 3eq.) followed by 352 mg of benzotriazol-1-yloxytris(dimethylamino)phosphonium hexafluorophosphate (0.79 mmol, 1.5eq). After stirring at room temperature for 2 hours, the solvent was removed under reduced pressure and the residue was purified by chromatography on silica gel (eluant 3:2 ethyl acetate/hexane) to give 240 mg (97%) of the product as a white solid. $^1$H NMR (400 MHz, CDCl$_3$): 1.15 (s, 1H), 1.16 (s, 3H), 1.40 (s, 9H), 2.23 (s, 1H), 2.91 (dd; 7,13 Hz, H), 3.08 (dd; 9, 13 Hz 1H), 3.80 (s, 3H), 4.02 (m, 1H), 4.76 (t, 8 Hz, 1H), 5.20 (br s, 1H), 6.12 (d, 8Hz, 1H), 6.83 (d, 8 Hz, 2H), 7.01 (d, 8 Hz, 1H), 7.12≅7.30 (m, 5H), 7.59 (s, 1H) FAB-MS: calculated for C$_{27}$H$_{35}$N$_3$O$_5$ 481; found 482 (35%).

Step I: 5-Phenyltetrazole

Zinc chloride (3.3g, 24.3 mmol, 0.5eq) was added to 15mL of N,N-dimethylformamide in small portions while maintaining the temperature below 60° C. The suspension of zinc chloride was cooled to room temperature and treated with 5.0 g of benzonitrile (48.5 mmol, 1.0 eq) followed by 3.2g of sodium azide (48.5 mmol, 1.0 eq). The heterogeneous mixture was heated at 115° C. with agitation for 18 hours. The mixture was cooled to room temperature, water (30 mL) was added and the mixture acidified by the addition of 5.1 mL of concentrated hydrochloric acid. The mixture was cooled to 0° C. and aged for one hour, then filtered and the filter cake washed with 15 mL of cold 0.1 N HCl then dried at 60° C. under vacuum to afford 6.38g (43.7 mmol, 90%) of the product.

Step J: 5-Phenyl-2-trityltetrazole

To a suspension of 5.0 g (34.2 mmol) of 5-phenyltetrazole in 55 mL of acetone was added 5.0 mL of triethylamine (3.6g, 35.6 mmol, 1.04eq). After 15 minutes, a solution of 10.0 g of triphenylmethyl chloride (35.9 mmol, 1.05eq) in 20 mL of tetrahydrofuran was added and the mixture stirred at room temperature for one hour. Water (75 mi) was slowly added and the mixture stirred for one hour at room temperature. The product was collected by filtration, washed with 75 mL of water and dried at 60° C. under vacuum to give 13.3g (34.2 mmol, 100%) of the product.

Step K:
N-Triphenylmethyl-5-[2-(41-methylbiphen-4-yl)]tetrazole

A solution of zinc chloride (6.3g, 46.2 mmol, 0.6eq) in 35mL of tetrahydrofuran was dried over molecular sieves. 5-Phenyl-2-trityltetrazole (30.0g, 77.3 mmol, 1.0 eq) was dissolved in 300 mL of dry tetrahydrofuran and the solution gently stirred while being degassed three times by alternating vacuum and nitrogen purges. The stirred solution was cooled to −15° C. and treated slowly with 50.5 mL of 1.6M n-butyllithium in hexane (80.0 mmol, 1.05 eq) so as to maintain the temperature below −5° C. The solution was maintained at −5° to −15° C. for 1.5 hours then treated with the dried zinc chloride solution and allowed to warm to room temperature.

In a separate flask, 4-iodotoluene (20.17g, 92.5 mmol, 1.2eq) and bis(triphenylphosphine)nickel(II) dichloride (1.5g, 2.3 mmol, 0.03 eq) were-dissolved in 60 mL of tetrahydrofuran, then degassed and left under an atmosphere of nitrogen. The mixture was cooled to 5° C. and treated with 1.5 mL of 3.0 M solution of methylmagnesium chloride in tetrahydrofuran (4.5 mmol, 0.06eq) so as to keep the temperature below 10° C. The solution was warmed to room temperature and added, under nitrogen purge, to the arylzinc solution. The reaction mixture was stirred vigorously for 8 hours at room temperature then quenched by the slow addition of a solution of 10 mL of glacial acetic acid (1.6 mmol, 0.02 eq) in 60 mL of tetrahydrofuran at a rate so that the temperature was maintained below 40° C. The mixture was stirred for 30 minutes and 150 mL of 80% saturated aqueous sodium chloride was added; the reaction mixture was extracted for 30 minutes and the layers allowed to separate. The organic layer was removed and washed with 150 mL of 80% saturated aqueous sodium chloride buffered to pH>10 by the addition of ammonium hydroxide. The organic phase was removed and concentrated under vacuum to approximately 50 mL then 250 mL of acetonitrile was added. The mixture was again concentrated under vacuum to 50 mL and acetonitrile added to make the final volume 150 mL. The resulting slurry was cooled at 5° C. for 1 hour then filtered and washed with 50 mL of cold acetonitrile followed by 150 mL of distilled water. The filter cake was air dried to a free flowing solid then further dried under vacuum at 50° C. for 12 hours to afford 30.0g (62.8 mmol, 81%) of the product.

$^1$H NMR (200 MHz, CDCl$_{13}$): 2.28 (s, 3H), 6.9–7.05 (m, 10H), 7.2–7.5 (m, 12H), 7.9 (m, 1H).

Step L:
N-Triphenylmethyl-5-[2-(4¹-bromomethylbiphen-4-yl)] tetrazole

A solution of 3.15g (6.6 mmol) of N-triphenylmethyl-5-[2-(4¹-methylbiphen-4-yl)]tetrazole in 25 mL of methylene chloride was treated with 1.29g (7.25 mmol, 1.1 eq) of N-bromosuccinimide, 80mg (0.5 mmol, 0.07eq) of AIBN, 200 mg of sodium acetate and 200 mg of acetic acid. The mixture was heated at reflux for 16 hours then cooled and washed with saturated aqueous sodium bicarbonate. The organic layer was removed, dried over sodium sulfate, filtered and concentrated to a minimum volume by atmospheric distillation. Methyl t-butyl ether was added and distillation continued until almost all the methylene chloride was removed the the total volume reduce to approximately 12 mL and 12 mL of hexanes was then added. The mixture was kept at room temperature for 2 hours and the product isolated by filtration, washed with hexanes then dried under vacuum at 50° C. to give 2.81 g (5.04 mmol, 76%) of the product. $^1$H NMR (200 MHz, CDCl$_3$): 4.38 (s, 2H), 6.9–8.0 (m, 23H). NMR indicates presence of approximately 1% of the starting material and 7% of the dibromo derivative.

Step M:
3-t-Butoxycarbonylamino-3-methyl-N-[2,3,4,5-tetrahydro-2-oxo-4-(4-methoxyphenyl)-1-[[2'-(N-triphenylmethyl)-tetrazol-5-yl][1,1'-biphenyl]-4-yl]methyl-1H-1-benzazepin-3-yl]butanamide To a solution of 213 mg (0.457 mmol) of 3-t-butoxycarbonylamino-3-methyl-N-[2,3,4,5-tetrahydro-2-oxo-4-(4-methoxyphenyl)-1H-1-benzazepin-3-yl]butanamide in 6mL of tetrahydrofuran/dimethylformamide (5:1) under a nitrogen atmosphere at room temperature was added 24 mg (0.6 mmol,1.3 eq) of 60% sodium hydride oil dispersion. After 30 minutes, a solution of 280 mg (0.503 mmol, 1.1 eq) of N-triphenylmethyl-5-[2-(4'-bromomethylbiphen- 4-yl)] tetrazole in 2mL of dry tetrahydrofuran was added and the mixture was stirred for 2 hours. The reaction mixture was poured into ethyl acetate and washed with water and brine. The organic layer was separated, dried over magnesium sulfate, filtered and the solvent was removed under vacuum. Purification by column chromatography on silica gel (eluant 1:1; ethyl acetate/hexane) afforded 360 mg (84%) of the product. $^1$H NMR (400 MHz, CDCl$_3$): 1.14 (s, 1H), 1.18 (s, 3H), 1.39 (s, 9H), 2.14 (d, 12 Hz, 1H), 2.20 (d, 12 Hz, 1H), 2.65 (m, 2H), 3.76 (s, 3H), 3.82 (m, 1H), 4.69 (t, 7 Hz), 4.76 (d, 16 Hz, 1H), 5.22 (d, 16 Hz, 1H), 5.40 (br s, 1H), 6.13 (d, 7 Hz), 6.78 (d, 8 Hz, 2H), 6.88 (d, 8 Hz, 6H), 6.97 (d, 8 Hz, 2H), 7.02–7.35 (m, 18H), 7.44 (m, 2H), 7.86 (dd; 3, 9Hz; 1H).

Step N:
3-Amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide, trifluoroacetate A solution of 350 mg (0.371 mmol) of the intermediate obtained in Step M in 10 mL of methanol was treated with 3 mL of 9N hydrochloric acid and 5 mL of hexane. After stirring at room temperature for 3 hours, the methanol layer was separated and concentrated under vacuum. The residue was purified by reverse phase medium pressure liquid chromatography on C8, eluting with methanol/0.1% aqueous trifluoroacetic acid (65/35), to give 229 mg (85%) of the title compound as a white solid $^1$H NMR (400 MHz, CD$_3$OD): 1.21 (s, 3H), 1.24 (s, 3H), 2.28 (d, 16 Hz, 1H), 2.39 (d, 16 Hz, 1H), 2.72 (m, 2H), 3.73 (m, 1H), 3.79 (s, 3H), 4.70 (d, 8 Hz, 1H), 4.94 (d, 15 Hz, 1H), 5.39 (d, 15 Hz, 1H), 6.88 (d, 8 Hz, 2H), 7.06 (m, 4H), 7.22–7.39 (m, 6H), 7.52 (m, 2H), 7.62 (m, 2H). FAB-MS: calculated for C$_{36}$H$_{37}$N$_7$O$_3$ 615 found 616 (100%).

EXAMPLE 2

3-Amino-3-methyl-N-[2,3,4,5-tetrahydro-2-oxo-4-(4-hydroxyphenyl)-1-[[2'-(1H-tetrazol-5-yl)[1,1'-biphenyl]-4-yl]methyl]-1H-1-benzazepin-3-yl]-butanamide, trifluoroacetate A solution of 25 mg (0.034 mmol) of 3-amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide, trifluoroacetate (Example 1) in 5 mL of dichloroethane was treated with excess boron tribromide-dimethyl sulfide complex (100 mL of 1.0 M solution in methylene chloride) and the resulting mixture was heated at reflux in an oil bath for 16 hours. The solvent was removed under vacuum and the residue was purified by reverse phase medium pressure liquid chromatography on C-18, eluting with methanol/0.1% aqueous trifluoroacetic acid (60/40), to give 14mg (58%) of the title compound. $^1$H NMR (400 MHz, CD$_3$OD): 1.20 (s, 3H), 1.23 (s, 3H), 2.28 (d, 16 Hz, 1H), 2.39 (d, 16 Hz, 1H), 2.72 (m, 2H), 3.70 (m, 1H), 4.69 (d, 9 Hz, 1H), 4.96 (d, 15 Hz, 1H), 5.38 (d, 15 Hz, 1H), 6.73 (d, 8 Hz, 2H) 6.98 (d, 8 Hz, 2H), 7.05 (d, 8 Hz, 2H), 7.25–7.39 (m, 6H), 7.54 (m, 2H), 7.64 (m, 2H). FAB-MS: calculated for C$_{36}$H$_{37}$N$_7$O$_3$ 601; found 602 (100%).

EXAMPLE 3

3-Amino-3-methyl-N-[2,3,4,5-tetrahydro-2-oxo-4-phenyl-1-[[2'-(1H-tetrazol-5-yl)[1,1'-biphenyl]-4-yl]methyl-1H-1-benzazepin-3-yl]-butanamide, trifluoroacetate The title compound was prepared from 2,3,4,5-tetrahydro-3-(methoxycarbonyl)-4-phenyl-1H-1-benzazepin-2-one [prepared by the method of Floyd, et al., J. Med. Chem., 35, 756–772 (1992)] by the methods described in Example 1. $^1$H NMR (400 MHz, CD$_3$OD): 1.17 (s, 3H), 1.21 (s, 3H), 2,28 (d, 16 Hz, 1H), 2.38 (d, 16 Hz, 1H), 2.75 (m, 2H), 3.83 (m, 1H), 4.73 (d, 7 Hz, 1H), 4.96 (d, 15 Hz, 1H), 5.41 (d, 15 Hz, 1H), 7.06 (d, 8 Hz, 2H), 7.15–7.45 (m, 10H), 7.54 (m,2H), 7.64 (m,2H). FAB-MS: calculated for C$_{35}$H$_{35}$N$_7$O2 585; found 587 (100%).

EXAMPLE 4

3-Amino-3-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-butanamide, trifluoroacetate Step A: 4-Methyl-1-tetralone oxime A solution of 801 mg (5.0 mmol) of 4-methyl-1-tetralone in 20 mL of dry methanol was treated with 417 mg of hydroxylamine hydrochloride (6.0 mmol, 1.2 eq) and 504 mg (6.0 mmol, 1.2 eq) of sodium bicarbonate and the resulting mixture was stirred at room temperature for 16 hours. The solid was filtered off and the solvent was removed under vacuum. The white residue was redissolved in 10 mL of methylene chloride and filtered. The filtrate was evaporated to dryness under vacuum to give the product in quantitative yield. $^1$H NMR (400 MHz, CDCl$_3$): 1.30 (d, 8 Hz, 3H), 1.69 (m, 1H), 2.45 (m, 1H), 2.88 (m, 3H), 7.15–7.35 (m, 3H), 7.86 (d, 8 Hz, 1H).

Step B: 2,3,4,5-Tetrahydro-5-methyl-1H-1-benzazepin-2-one

A mixture of 800 mg (4.57 mmol) of 4-methyl-1-tetralone oxime and 4.0 g of polyphosphoric acid was heated at 120° C. in an oil bath for 20 minutes. The dark brown mixture was cooled to 80° C. and poured into ice water. The solution was neutralized by the addition of 10% aqueous sodium carbonate then extracted chloroform (3×50 mL). The combined extracts were washed with water, dried over magnesium sulfate and filtered. Evaporation of the solvent followed by column chromatography on silica gave the product as an off-white solid (670 mg, 84%). $^1$H NMR (200 MHz, CDCl$_3$): 1.30 (d, 8 Hz, 3H), 1.68 (m, 1H), 2.30 (m, 3H), 3.11 (m, 1H), 6.98 (m, 1H), 7.15–7.30 (m, 3H), 8.55 (br s, 1H). $^{13}$C NMR: 18.22, 32.89, 32.98, 37.28, 121.95, 125.67, 125.93, 126.98, 137.69, 137.80, 176.04.

Step C: 3-Amino-3-methyl-N--[2,3,4,5-tetrahydro-2-oxo-5-methyl-1-[[2'-(1H-tetrazol-5-yl)[1,1'-biphenyl]-4-yl]methyl-1H-1-benzazepin-3-yl]-butanamide trifluoroacetate The title compound is prepared from 2,3,4,5-tetrahydro-5-methyl-1H-1-benzazepin-2-one by the methods described in Example 1.

Example 5

3-Amino-3-methyl-N-[2,3,4,5-tetrahydro-4-oxo-2-(4-methoxyphenyl)-5-[[2'-(1H-tetrazol-5-yl)[1,1'-biphenyl]-4-yl]methyl-5H-1,5-benzothiazepin-3-yl]-butanamide, trifluoroacetate Step A: 2,3,4,5-Tetrahydro-2-(4-methoxyphenyl)-3-methanesulfonyloxy-5H-1,5-benzothiazepin-4-one To a cooled solution (0° C.) of 259 mg (1.0 mmol) of 2,3,4,5-tetrahydro-2-(methoxyphenyl)-3-hydroxy-5H-1,5-benzothiazepin-4-one [prepared by the method of Kugita, H. et al., Chem. Pharm. Bull., 19, 595–602, (1971)] in 10 mL of methylene chloride is added 0.140 mL of triethylamine (101 mg, 1 eq) followed by 0.078 mL of methanesulfonyl chloride (115 mg, 1 eq.). The reaction mixture is stirred at room temperature for 30 minutes and the solvent is removed under vacuum. The product is used without further purification.

Step B: 2,3,4,5-Tetrahydro-2-(methoxyphenyl)-3-azido-5H-1,5-benzothiazeyine-4-one A solution of 337 mg (1.0 mmol) of 2,3,4,5-tetrahydro-2-(4 -methoxyphenyl)-3-methanesulfonyloxy-5H-1,5-benzothiazepin-4-one in 5 mL of dry dimethylformamide and 195 mg (3 mmol, 3 eq) of sodium azide is heated at 60° C. in an oil bath for 14 hours. The reaction is diluted with ethyl acetate, washed with water and brine, dried over magnesium sulfate and filtered. Removal of the solvent under vacuum followed by column chromatography on silica gel gives the desired product.

Step C: 3-Amino-3-methyl-N-[2,3,4,5-tetrahydro-4-oxo-2-(4-methoxyphenyl)-5-[[2'-(1H-tetrazol-5-yl)[1,1'-biphenyl]-4-yl]methyl-5H-1,5-benzothiazepin-3-yl]-butanamide, trifluoroacetate The title compound is prepared from 2,3,4,5-tetrahydro-2-(4-methoxyphenyl)-3-azido-5H-1,5-benzothiazepin-4-one by the methods described in Example 1.

Example 6

3-[2(R)-Hydroxypropyl]amino-3-methyl-N [2,3,4,5-tetrahydro-2-oxo-4-(4-methoxyphenyl)-1-[[2'-(1H-tetrazol-5-yl)[1,1'-biphenyl]-4-yl]methyl-1H-1-benzazepin-3-yl]-butanamide, trifluoroacetate Step A: 3-[2(R)-Benzyloxypropyl]amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl-1H-1-benzazepin-3-yl]-butanamide, trifluoroacetate A solution of 100 mg (0.14 mmol) of 3-amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide, trifluoroacetate (Example 1) in 3 mL of dry methanol was treated with activated powdered molecular sieves (100 mg) and 225 mg (1.37 mmol, 10 eq) of freshly prepared (R)-2-benzyloxypropanal (prepared from ethyl-D-lactate according to the procedure of Hanessian and Kloss, Tetrahedron Lett. 1985, 26, 1261–1264) and the resulting mixture was stirred at room temperature under a nitrogen atmosphere. After 30 minutes, a solution of sodium cyanoborohydride (1.0 mL of 1M solution in tetrahydrofuran, 1 mmol, 7.3 eq) was added and stirring was continued overnight. The reaction mixture was filtered and the solids washed with 10 mL of methanol. The filtrate was treated with 1 mL of trifluoroacetic acid to quench excess sodium cyanoborohydride. The solvent was removed under vacuum and the the residue was purified by reverse phase medium pressure liquid chromatography on C8, eluting with methanol/0.1% aqueous trifluoroacetic acid (70:30) to give 86 mg (72%) of the product. FAB-MS: calculated for $C_{46}H_{49}N_7O_4$ 763; found 764 (100%).

Step B:
3-[2(R)-Hydroxypropyl]amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl-1H-1-benzazepin-3-yl]-butanamide, trifluoroacetate A solution of 80 mg (0.91 mmol) of the intermediate obtained in Step A in 1 mL of acetic acid was treated with 3 mL of 30% hydrogen bromide/acetic acid solution and the resulting mixture stirred at room temperature for 2 hours. The solvent was removed under vacuum and the residue was treated with 2 mL of a 10% solution of sodium methoxide in methanol. After stirring for 30 minutes, the reaction mixture was treated with 1 mL of trifluoroacetic acid and the solvent was removed under vacuum. Purification by reverse phase medium pressure liquid chromatography on C8, eluting with methanol/0.1% aqueous trifluoroacetic acid (65:35), gave 50 mg (70%) of the title compound as a white solid. FAB-MS: calculated for $C_{39}H_{43}N_7O_4$ 673; found 674 (100%).

What is claimed is:
1. A compound having the formula:

form 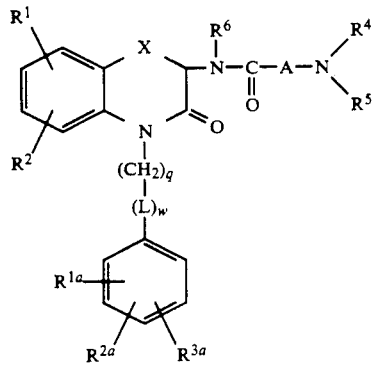

where
L is

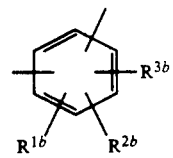

q is 0 to 4;
w is 0 or 1;
$R^1$, $R^2$, $R^{1a}$, $R^{2a}$, $R^{1b}$, and $R^{2b}$ are independently hydrogen, halogen, $C_1$-$C_7$ alkyl, $C_1$-$C_3$ perfluoroalkyl, $C_1$-$C_3$ perfluoroalkoxy, —S(O)$_m$R$^{7a}$, cyano, nitro, $R^{7b}$O(CH$_2$)$_v$—, $R^{7b}$COO(CH$_2$)$_v$—, $R^{7b}$OCO(CH$_2$)$_v$—, $R^4R^5$N(CH$_2$)$_v$—, $R^{7b}$CON(R$^4$)(CH$_2$)$_v$—, $R^4R^5$NCO(CH$_2$)$_v$—, phenyl or substituted phenyl where the substituents are from 1 to 3 of halogen, $C_1$-$C_6$ alkyl, $C_1$-$C_6$ alkoxy, or hydroxy; $R^{7a}$ and $R^{7b}$ are independently hydrogen, $C_1$-$C_3$ perfluoroalkyl, $C_1$-$C_6$ alkyl, substituted $C_1$-$C_6$ alkyl, where the substituents are phenyl or substituted phenyl; phenyl or substituted phenyl where the phenyl substituents are from 1 to 3 of halogen, $C_1$-$C_6$ alkyl, $C_1$-$C_6$ alkoxy, or hydroxy and v is 0 to 3;
$R^{3a}$ and $R^{3b}$ are independently hydrogen, $R^9$, $C_1$-$C_6$ alkyl substituted with $R^9$, phenyl substituted with $R^9$, or phenoxy substituted with $R^9$;
m is 0 to 2;
$R^9$ is

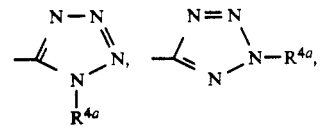

$R^{7b}$O(CH$_2$)$_v$—, $R^{7b}$COO(CH$_2$)$_v$—, $R^{7b}$OCO(CH$_2$)$_v$—, $R^{7b}$CO(CH$_2$)$_v$—, $R^{7b}$(CH$_2$)$_v$CO—, $R^4R^5$N(CH$_2$)$_v$—, $R^{7b}$CON(R$^4$)(CH$_2$)$_v$—, $R^4R^5$NCO(CH$_2$)$_v$—, $R^4R^5$NCS(CH$_2$)$_v$—, $R^4R^5$NN(R$^5$)CO(CH$_2$)$_v$—, $R^4R^5$NN(R$^5$)CS(CH$_2$)$_v$—, $R^{7b}$CON(R$^4$)N(R$^5$)CO(CH$_2$)$_v$—, $R^{7b}$CON(R$^4$)N(R$^5$)CS(CH$_2$)$_v$—, $R^4$N(OR$^{7b}$)CO(CH$_2$)$_v$—, $R^{7a}$CON(OR$^{7b}$)CO(CH$_2$)$_v$—, $R^{4b}R^{12a}$NCON(R$^{12b}$)(CH$_2$)$_v$—, $R^{4b}R^{12a}$NCSN(R$^{12b}$)(CH$_2$)$_v$—, $R^{4b}R^{12a}$NN(R$^{12b}$)CSN(R$^{12c}$)(CH$_2$)$_v$—, $R^{4b}R^{12a}$NN(R$^{12b}$)CON(R$^{12c}$)(CH$_2$)$_v$—, $R^{4b}R^{12a}$NN(R$^{12b}$)COO(CH$_2$)$_v$—, $R^{4b}R^{12a}$NCOO(CH$_2$)$_v$— or $R^{13}$OCON(R$^{12b}$)(CH$_2$)$_v$—,
where v is 0 to 3;
$R^{12a}$, $R^{12b}$ and $R^{12c}$ are independently $R^{5a}$, OR$^{5a}$, or COR$^{5a}$; $R^{12a}$ and $R^{12b}$, or $R^{12b}$ and $R^{12c}$, or $R^{13}$ and $R^{12b}$, or $R^{12a}$ and $R^{4b}$ when taken together form —(CH$_2$)$_r$—B—(CH$_2$)$_s$— where B is CHR$^1$, O, S(O)$_m$ or NR$^{10}$, m is 0, 1 or 2, r and s are independently 0 to 3 and $R^1$ and $R^{10}$ are as defined;
$R^{13}$ is $C_1$-$C_3$ perfluoroalkyl, $C_1$-$C_6$ alkyl, substituted $C_1$-$C_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, $C_1$-$C_6$ alkyl, $C_1$-$C_6$ alkoxy or hydroxy; where $R^{10}$ and $R^{11}$ are independently hydrogen, $C_1$-$C_6$ alkyl, phenyl, phenyl $C_1$-$C_6$ alkyl, $C_1$-$C_5$-alkoxycarbonyl, or $C_1$-$C_5$-alkanoyl-$C_1$-$C_6$ alkyl;

X is —CH$_2$CH(R$^{20}$)—, —CH(R$^{21}$)CH$_2$—, —CH(R$^{21}$)CH(R$^{20}$)—, —CH=C(R$^{20}$)—, —C(R$^{21}$)=CH—, —C(R$^{21}$)=C(R$^{20}$)—, —S(O)$_m$CH(R$^{20}$)— or —OCH(R$^{20}$)—;

R$^{20}$ and R$^{21}$ are independently hydrogen, R$^1$, R$^2$ independently disubstituted phenyl, R$^1$, R$^2$ independently disubstituted thiophenyl, C$_1$-C$_{10}$ alkyl, substituted C$_1$-C$_{10}$ alkyl, C$_2$-C$_{10}$ alkenyl, substituted C$_2$-C$_{10}$ alkenyl, C$_2$-C$_{10}$ alkynyl, substituted C$_2$-C$_{10}$ alkynyl where the substituents on the alkyl, alkenyl, alkynyl are from 1 to 3 of hydroxy, C$_1$-C$_6$ alkoxy, fluoro, R$^1$ substituted phenyl, —NR$^{10}$R$^{11}$, carboxy, C$_1$-C$_5$ alkoxycarbonyl, formyl or R$^{20}$ and R$^{21}$ when taken together form —(CH$_2$)$_r$B(CH$_2$)$_s$— where B, r, s, R$^1$, R$^2$, R$^{10}$ and R$^{11}$ are as defined above, with the proviso that R$^{20}$ and R$^{21}$ cannot both be hydrogen;

R$^4$, R$^{4a}$, R$^{4b}$, R$^5$ and R$^{5a}$ are independently hydrogen, phenyl, substituted phenyl, C$_1$-C$_{10}$ alkyl, substituted C$_1$-C$_{10}$ alkyl, C$_3$-C$_{10}$ alkenyl, substituted C$_3$-C$_{10}$ alkenyl, C$_3$-C$_{10}$ alkynyl, or substituted C$_3$-C$_{10}$ alkynyl where the substituents on the phenyl, alkyl, alkenyl or alkynyl are from 1 to 5 of hydroxy, C$_1$-C$_6$ alkoxy, C$_3$-C$_7$ cycloalkyl, fluoro, R$^1$, R$^2$ independently disubstituted phenyl C$_1$-C$_3$ alkoxy, R$^1$, R$^2$ independently disubstituted phenyl, C$_1$-C$_{20}$-alkanoyloxy, C$_1$-C$_5$ alkoxycarbonyl, carboxy, formyl, or —NR$^{10}$R$^{11}$; or R$^4$ and R$^5$ when taken to form —(CH$_2$)$_r$B(CH$_2$)$_s$— where B, r, s, R$^1$, R$^2$, R$^{10}$ and R$^{11}$ are as defined above;

R$^6$ is hydrogen, C$_1$-C$_{10}$ alkyl, phenyl or phenyl C$_1$-C$_{10}$ alkyl;

A is

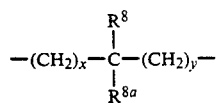

where x and y are independently 0-3;

R$^8$ and R$^{8a}$ are independently hydrogen, C$_1$-C$_{10}$ alkyl, trifluoromethyl, phenyl, substituted C$_1$-C$_{10}$ alkyl where the substituents are from 1 to 3 of imidazolyl, indolyl, hydroxy, fluoro, S(O)$_m$R$^{7a}$, C$_1$-C$_6$ alkoxy, C$_3$-C$_7$ cycloalkyl, R$^1$, R$^2$ independently disubstituted phenyl C$_1$-C$_3$ alkoxy, R$^1$, R$^2$ independently disubstituted phenyl, C$_1$-C$_5$-alkanoyloxy, C$_1$-C$_5$ alkoxycarbonyl, carboxy, formyl, or —NR$^{10}$R$^{11}$ where R$^{10}$ and R$^{11}$ are as defined above; or R$^8$ and R$^{8a}$ when taken together form —(CH$_2$)$_t$— where t is 2 to 6; and R$^8$ and R$^{8a}$ when independently joined to one or both of R$^4$ and R$^5$ form alkylene bridges between the terminal nitrogen and the alkyl portion of the A group wherein the bridge contains from 1 to 5 carbon atoms;

or pharmaceutically acceptable salts thereof.

2. A compound of claim 1 wherein:
q is 0 to 2;
w is 0 or 1;
R$^1$, R$^2$, R$^{1a}$, R$^{2a}$, R$^{1b}$, and R$^{2b}$ are independently hydrogen, halogen, C$_1$-C$_7$ alkyl, C$_1$-C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$-C$_6$ alkyl, C$_1$-C$_6$ alkoxy, or hydroxy;
m is 0 to 2;

R$^{7a}$ and R$^{7b}$ are independently hydrogen, C$_1$-C$_3$ perfluoroalkyl, C$_1$-C$_6$ alkyl, substituted C$_1$-C$_6$ alkyl, where the substituents are phenyl; phenyl and v is 0 to 2;

R$^{3a}$ and R$^{3b}$ are independently hydrogen, R$^9$, C$_1$-C$_6$ alkyl substituted with R$^9$, phenyl substituted with R$^9$, or phenoxy substituted with R$^9$;

R$^9$ is

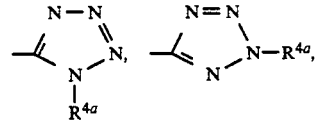

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$R$^5$NN(R$^5$)CO(CH$_2$)$_v$—, R$^{7b}$CON(R$^4$)N(R$^5$)CO(CH$_2$)$_v$—, R$^4$N(OR$^{7b}$)CO(CH$_2$)$_v$—, R$^{7a}$CON(OR$^{7b}$)CO(CH$_2$)$_v$—, R$^{4b}$R$^{12a}$NCON(R$^{12b}$)(CH$_2$)$_v$—, R$^{4b}$R$^{12a}$NCSN(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 3;

R$^{12a}$, R$^{12b}$ and R$^{12c}$ are independently R$^{5a}$, OR$^{5a}$, or COR$^{5a}$; R$^{12a}$ and R$^{12b}$, or R$^{12b}$ and R$^{12c}$, or R$^{13}$ and R$^{12b}$, or R$^{12a}$ and R$^{4b}$ when taken together form —(CH$_2$)$_r$—B—(CH$_2$)$_s$— where B is CHR$^1$, O, S(O)$_m$ or NR$^{10}$, m is 0, 1 or 2, r and s are independently 0 to 3, R$^1$ is as defined above and R$^{10}$ is hydrogen, C$_1$-C$_6$ alkyl, phenyl C$_1$-C$_6$ alkyl or C$_1$-C$_5$ alkanoyl-C$_1$-C$_6$ alkyl.

R$^{13}$ is C$_1$-C$_3$ perfluoroalkyl, C$_1$-C$_6$ alkyl, substituted C$_1$-C$_6$ alkyl, where the substitutents are hydroxy, —NR$^{10}$R$^{11}$, carboxy, phenyl or substituted phenyl; phenyl or substituted phenyl where the substituents on the phenyl are from 1 to 3 of halogen, C$_1$-C$_6$ alkyl, C$_1$-C$_6$ alkoxy or hydroxy;

where X is as defined in claim 1;

R$^4$, R$^{4a}$, R$^{4b}$, R$^5$ and R$^{5a}$ are independently hydrogen, phenyl, substituted phenyl, C$_1$-C$_{10}$ alkyl, substituted C$_1$-C$_{10}$ alkyl, where the substituents on the alkyl or phenyl are from 1 to 5 of hydroxy, C$_1$-C$_6$ alkoxy, C$_3$-C$_7$ cycloalkyl, fluoro, R$^1$, R$^2$ independently disubstituted phenyl C$_1$-C$_3$ alkoxy, R$^1$, R$^2$ independently disubstituted phenyl, C$_1$-C$_{20}$-alkanoyloxy, C$_1$-C$_5$ alkoxycarbonyl, carboxy, formyl;

R$^4$ and R$^5$ where taken together to form —(CH$_2$)$_r$B(CH$_2$)$_s$— where B is CHR$^1$, O, S(O)$_m$ or N-R—$^{10}$, r and s are independently 1 to 3 and R$^1$ and R$^{10}$ are as defined above;

R$^6$ is hydrogen, C$_1$-C$_{10}$ alkyl or phenyl C$_1$-C$_{10}$ alkyl;

A is

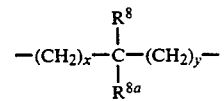

where x and y are independently 0-2;

R$^8$ and R$^{8a}$ are independently hydrogen, C$_1$-C$_{10}$ alkyl, substituted C$_1$-C$_{10}$ alkyl where the substituents are from 1 to 3 of imidazolyl, indolyl, hydroxy, fluoro, S(O)$_m$R$^{7a}$, C$_1$-C$_6$ alkoxy, R$^1$, R$^2$ independently disubstituted phenyl, C$_1$-C$_5$-alkanoyloxy, C$_1$-C$_5$ alkoxycarbonyl, carboxy, formyl, or —NR$^{10}$R$^{11}$ where R$^{10}$ and R$^{11}$ are independently hydrogen, C$_1$-C$_6$ alkyl or C$_1$-C$_5$ alkanyol-C$_1$-C$_6$ alkyl; or R$^8$ and R$^{8a}$ when taken together form —(CH$_2$)$_t$— where t is 2 to 4; and R$^8$ and R$^{8a}$ when independently joined to one or both of R$^4$ and R$^5$ form alkylene bridges between the terminal nitrogen and the alkyl portion of the A group wherein the bridge contains from 1 to 5 carbon atoms;

or pharmaceutically acceptable salts thereof.

3. A compound of claim 2 wherein:

q is 0 to 2;

w is 0 or 1;

R$^1$, R$^2$, R$^{1a}$, R$^{2a}$, R$^{1b}$, and R$^{2b}$ are independently hydrogen, halogen, C$_1$-C$_7$ alkyl, C$_1$-C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$-C$_6$ alkyl, C$_1$-C$_6$ alkoxy, or hydroxy;

m is 0 to 1;

R$^{7a}$ and R$^{7b}$ are independently hydrogen, C$_1$-C$_6$ alkyl, substituted C$_1$-C$_6$ alkyl, where the substituents are phenyl; phenyl and v is 0 to 2;

R$^{3a}$ and R$^{3b}$ are independently hydrogen, R$^9$, C$_1$-C$_6$ alkyl substituted with R$^9$, phenyl substituted with R$^9$ or phenoxy substituted with R$^9$;

R$^9$ is

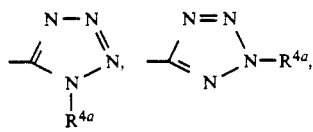

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^4$R$^5$N(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$N(OR$^{7b}$)CO(CH$_2$)$_v$—, R$^{7a}$CON(OR$^{7b}$)CO(CH$_2$)$_v$—, R$^{4b}$R$^{12a}$NCON(R$^{12b}$)(CH$_2$)$_v$—, R$^{4b}$R$^{12a}$NCSN(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 2;

R$^{12a}$, R$^{12b}$ and R$^{12c}$ are independently R$^{5a}$ or OR$^{5a}$ R$^{12a}$ and R$^{12b}$, or R$^{12b}$ and R$^{12c}$, or R$^{13}$ and R$^{12b}$, or R$^{12a}$ and R$^{4b}$ when taken together form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$-C$_6$ alkyl or C$_1$-C$_5$ alkanoyl-C$_1$-C$_6$ alkyl.

R$^{13}$ is C$_1$-C$_6$ alkyl, substituted C$_1$-C$_6$ alkyl, where the substitutents are phenyl or substituted phenyl; phenyl or substituted phenyl where the substituents on the phenyl are from 1 to 3 of halogen, C$_1$-C$_6$ alkyl, C$_1$-C$_6$ alkoxy or hydroxy;

R$^4$, R$^{4a}$, R$^{4b}$, R$^5$ and R$^{5a}$ are independently hydrogen, C$_1$-C$_{10}$ alkyl, substituted C$_1$-C$_{10}$ alkyl, where the substituents on the alkyl are from 1 to 5 of hydroxy, C$_1$-C$_6$ alkoxy, fluoro, R$^1$, R$^2$ independently disubstituted phenyl C$_1$-C$_{20}$-alkanoyloxy, C$_1$-C$_5$ alkoxycarbonyl or carboxy;

R$^6$ is hydrogen or C$_1$-C$_{10}$ alkyl;

A is

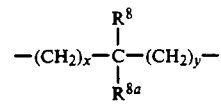

where x and y are independently 0-2;

R$^8$ and R$^{8a}$ are independently hydrogen, C$_1$-C$_{10}$ alkyl, substituted C$_1$-C$_{10}$ alkyl where the substituents are from 1 to 3 of imidazolyl, indolyl, hydroxy, fluoro, S(O)$_m$R$^{7a}$, C$_1$-C$_6$ alkoxy, R$^1$, R$^2$ independently disubstituted phenyl, C$_1$-C$_5$-alkanoyloxy, C$_1$-C$_5$ alkoxycarbonyl, carboxy; or R$^8$ and R$^{8a}$ when taken together form —(CH$_2$)$_t$— where t is 2; or R$^8$ and R$^{8a}$ when independently joined to one or both of R$^4$ and R$^5$ form alkylene bridges between the terminal nitrogen and the alkyl portion of the A group wherein the bridge contains from 1 to 5 carbon atoms;

or pharmaceutically acceptable salts thereof.

4. A compound of claim 3 wherein:

q is 1 w is 1;

R$^1$, R$^2$, R$^{1a}$, R$^{2a}$, R$^{1b}$, and R$^{2b}$ are independently hydrogen, halogen, C$_1$-C$_7$ alkyl, C$_1$-C$_3$ perfluoroalkyl, —S(O)$_m$R$^{7a}$, R$^{7b}$O(CH$_2$)$_v$—, R$^{7b}$COO(CH$_2$)$_v$—, R$^{7b}$OCO(CH$_2$)$_v$—, phenyl or substituted phenyl where the substituents are from 1 to 3 of halogen, C$_1$-C$_6$ alkyl, C$_1$-C$_6$ alkoxy, or hydroxy;

m is 0 to 1;

R$^{7a}$ and R$^{7b}$ are independently hydrogen, C$_1$-C$_6$ alkyl, substituted C$_1$-C$_6$ alkyl, where the substituents are phenyl; phenyl and v is 0 to 1;

R$^{3a}$ and R$^{3b}$ are independently hydrogen, R$^9$, C$_1$-C$_6$ alkyl substituted with R$^9$;

R$^9$ is

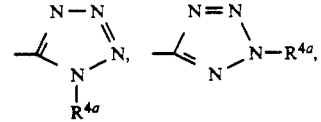

R$^{7b}$O(CH$_2$)$_v$—, R$^{7b}$COO(CH$_2$)$_v$—, R$^{7b}$OCO(CH$_2$)$_v$—, R$^{7b}$CO(CH$_2$)$_v$—, R$^{7b}$CON(R$^4$)(CH$_2$)$_v$—, R$^4$R$^5$NCO(CH$_2$)$_v$—, R$^4$R$^5$NCS(CH$_2$)$_v$—, R$^4$N(OR$^{7b}$)CO(CH$_2$)$_v$—, R$^{4b}$R$^{12a}$NCON(R$^{12b}$)(CH$_2$)$_v$—, R$^{4b}$R$^{12a}$NN(R$^{12b}$)CON(R$^{12c}$)(CH$_2$)$_v$—, R$^{4b}$R$^{12a}$NN(R$^{12b}$)COO(CH$_2$)$_v$—, R$^{4b}$R$^{12a}$NCOO(CH$_2$)$_v$— or R$^{13}$OCON(R$^{12b}$)(CH$_2$)$_v$—, where v is 0 to 1;

R$^{12a}$, R$^{12b}$ and R$^{12c}$ are independently R$^{5a}$. R$^{12a}$ and R$^{12b}$, or R$^{12b}$ and R$^{12c}$, or R$^{13}$ and R$^{12b}$ or R$^{12a}$ and R$^{4b}$ when taken together form —(CH$_2$)$_r$—B—(CH$_2$)$_s$— where B is CHR$^1$, O, S(O)$_m$ or NR$^{10}$, m is 0, 1 or 2, r and s are independently 0 to 2, R$^1$ is as defined above and R$^{10}$ is hydrogen, C$_1$-C$_6$ alkyl or C$_1$-C$_5$ alkanoyl-C$_1$-C$_6$ alkyl;

R$^{13}$ is C$_1$-C$_6$ alkyl, substituted C$_1$-C$_6$ alkyl, where the substitutents are phenyl or substituted phenyl; phenyl or substituted phenyl where the substituents on the phenyl are from 1 to 3 of halogen, C$_1$-C$_6$ alkyl, C$_1$-C$_6$ alkoxy or hydroxy;

R$^4$, R$^{4a}$, R$^{4b}$, R$^5$ and R$^{5a}$ are independently hydrogen, C$_1$-C$_{10}$ alkyl, substituted C$_1$-C$_{10}$ alkyl, where the substituents on the alkyl are from 1 to 3 of hydroxy, C₁-C₃ alkoxy, fluoro, R¹, R² independently disubstituted phenyl C₁-C₂₀ alkanoyloxy, C₁-C₅ alkoxycarbonyl or carboxy;
R⁶ is hydrogen;
A is

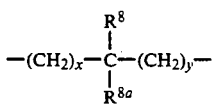

where x and y are independently 0-1;
R⁸ and R⁸ᵃ are independently hydrogen, C₁-C₁₀ alkyl, substituted C₁-C₁₀ alkyl where the substituents are from 1 to 3 of imidazolyl, indolyl, hydroxy, fluoro, S(O)ₘR⁷ᵃ, C₁-C₆ alkoxy, R¹, R² independently disubstituted phenyl, C₁-C₅-alkanoyloxy, C₁-C₅ alkoxycarbonyl, carboxy; or R⁸ and R⁸ᵃ when taken together form —(CH₂)ₜ— where t is 2; and R⁸ and R⁸ᵃ when independently joined to one or both of R⁴ and R⁵ form alkylene bridges between the terminal nitrogen and the alkyl portion of the A group wherein the bridge contains from 1 to 5 carbon atoms;
or pharmaceutically acceptable salts thereof.

5. A stereospecific compound of claim 1 having the following structural formula:

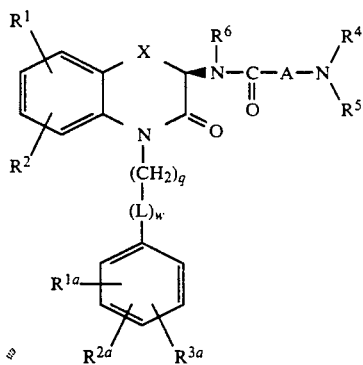

where R¹, R², X, q, L, w, R¹ᵃ, R²ᵃ, R³ᵃ, R⁴, R⁵, R⁶, and A are as defined in claim 1

6. A compound of claim 1 which is:
3-Amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide;
3-Amino-3-methyl-N-[2,3,4,5-tetrahydro-2-oxo-4-phenyl-1-[[2'-(1H-tetrazol-5-yl)[1,1'-biphenyl]-4-yl]methyl]-1H-1-benzazepin-3-yl]-butanamide;
3-Amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide;
3-[2(R)-Hydroxypropyl]amino-3-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide;
3-Amino-3-methyl-N-[2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide;
3-Amino-3-methyl-N-[7-trifluoromethyl-2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide;
3-Amino-3-methyl-N-[7-fluoro-2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide;
3-Amino-3-methyl-N-[7-methylthio-2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide;
3-[2(R)-Hydroxypropyl]amino-3-methyl-N-[2,3,4,5-tetrahydro-2-oxo-4-phenylthio-1-[[2'-(1H-tetrazol-5-yl)[1,1'-biphenyl]-4-yl]methyl]-1H-1-benzazepin-3-yl]-butanamide;
3-[2(R)-Hydroxypropyl]amino-3-methyl-N-[2,3,4,5-tetrahydro-2-oxo-5-phenylthio-1-[[2'-(1H-tetrazol-5-yl)[1,1'-biphenyl]-4-yl]methyl]-1H-1-benzazepin-3-yl]-butanamide;
3-[2(R)-Hydroxypropyl]amino-3-methyl-N-[2,3,4,5-tetrahydro-2-oxo-5-methyl-1-[[2'-(1H-tetrazol-5-yl)[1,1'-biphenyl]-4-yl]methyl]-1H-1-benzazepin-3-yl]-butanamide;
3-[2(S),3-Dihydroxypropyl]amino-3-methyl-N-[2,3,4,5-tetrahydro-2-oxo-4-phenylthio-1-[[2'-(1H-tetrazol-5-yl)[1,1'-biphenyl]-4-yl]methyl]-1H-1-benzazepin-3-yl]-butanamide;
3-Amino-3-methyl-N-[2,3,4,5-tetrahydro-2-oxo-4-methyl-1-[[2'-(1H-tetrazol-5-yl)[1,1'-biphenyl]-4-yl]methyl-1H-1-benzazepin-3-yl]-butanamide;
3-[2(R)-Hydroxypropyl]amino-3-methyl-N-[2,3,4,5-tetrahydro-2-oxo-4-methyl-1-[[2'-(1H-tetrazol-5-yl)[1,1'-biphenyl]-4-yl]methyl]-1H-1-benzazepin-3-yl]-butanamide;
3-Amino-3-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-butanamide;
3-[2(R)-Hydroxypropyl]amino-3-methyl-N-[2,3,4,5-tetrahydro-2-oxo-4-phenylthio-1-[[2'-(1H-tetrazol-5-yl)[1,1'-biphenyl]-4-yl]methyl]-1H-1-benzazepin-3-yl]-butanamide;
3-[2(S)-Dihydroxypropyl]amino-3-methyl-N-[2,3,4,5-tetrahydro-2-oxo-4-methyl-1-[[2'-(1H-tetrazol-5-yl)[1,1'-biphenyl]-4-yl]methyl]-1H-1-benzazepin-3-yl]-butanamide;
2-Amino-2-methyl-N-[2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-propanamide;
2-Amino-2-methyl-N-[7-methylthio-2,3,4,5-tetrahydro-2-oxo-4-(4-methoxyphenyl)-1-[[2'-(1H-tetrazol-5-yl)[1,1'-biphenyl]-4-yl]methyl]-1H-1-benzazepin-3-yl]-propanamide;
2-Amino-2-methyl-N-[2,3,4,5-tetrahydro-2-oxo-4-phenyl-1-[[2'-(1H-tetrazol-5-yl)[1,1'-biphenyl]-4-yl]methyl-1H-1-benzazepin-3-yl]-propanamide;
2-Amino-2-methyl-N-[2,3,4,5-tetrahydro-2-oxo-5-methyl-1-[[2'-(1H-tetrazol-5-yl)[1,1'-biphenyl]-4-yl]methyl-1H-1-benzazepin-3-yl]-propanamide;
2-Amino-2-methyl-N-[2,3,4,5-tetrahydro-2-oxo-4-methyl-1-[[2'-(1H-tetrazol-5-yl)[1,1'-biphenyl]-4-yl]methyl-1H-1-benzazepin-3-yl]-propanamide;
2-Amino-2-methyl-N-[2,3,4,5-tetrahydro-2-oxo-4,5-dimethyl-1-[[2'-(1H-tetrazol-5-yl)[1,1'-biphenyl]-4-yl]methyl-1H-1-benzazepin-3-yl]-propanamide;
2-Amino-2-methyl-N-[7-fluoro-2,3,4,5-tetrahydro-2-oxo-5-methyl-1-[[2'-(1H-tetrazol-5-yl)[1,1'-biphenyl]-4-yl]methyl-1H-1-benzazepin-3-yl]-propanamide;
2-Amino-2-methyl-N-[7-trifluoromethyl-2,3,4,5-tetrahydro-2-oxo-4-methyl-1-[[2'-(1H-tetrazol-5- yl)[1,1'-biphenyl]-4-yl]methyl-1H-1-benzazepin-3-yl]-propanamide;

N-Ethyl-4'-[[3-[(3-amino-3-methyl-1-oxobutyl)-amino]-2,3,4,5-tetrahydro-2-oxo-4-methyl-1H-1-benzazepin-1-yl]methyl][1,1'-biphenyl]-2-carboxamide;

4'-[[3-[(3-Amino-3-methyl-1-oxobutyl)-amino]-2,3,4,5-tetrahydro-2-oxo-5-methyl-1H-1-benzazepin-1-yl]methyl][1,1'-biphenyl]-2-carboxamide;

N-Ethyl-4'-[[3-[(3-amino-3-methyl-1-oxobutyl)-amino]-2,3,4,5-tetrahydro-2-oxo-4,5-dimethyl-1H-1-benzazepin-1-yl]methyl][1,1'-biphenyl]-2-carboxamide;

N-Ethyl-4'-[[3-[(3-amino-3-methyl-1-oxobutyl)-amino]-2,3,4,5-tetrahydro-2-oxo-4-(4-methoxyphenyl)-1H-1-benzazepin-1-yl]methyl][1,1'-biphenyl]-2-carboxamide;

4'-[[3-[(3-Amino-3-methyl-1-oxobutyl)-amino]-2,3,4,5-tetrahydro-2-oxo-5-phenylthio-1H-1-benzazepin-1-yl]methyl][1,1'-biphenyl]-2-carboxamide;

N-Ethyl-4'-[[3-[(3-amino-3-methyl-1-oxopropyl)-amino]-2,3,4,5-tetrahydro-2-oxo-4-(4-methyl)-1H-1-benzazepin-1-yl]methyl][1,1'-biphenyl]-2-carboxamide;

N-Ethyl-4'-[[3-[(3-amino-3-methyl-1-oxopropyl)-amino]-2,3,4,5-tetrahydro-2-oxo-5-methyl-1H-1-benzazepin-1-yl]methyl][1,1'-biphenyl]-2-carboxamide;

N-Ethyl-4'-[[3-[(3-amino-3-methyl-1-oxopropyl)-amino]-7-fluoro-2,3,4,5-tetrahydro-2-oxo-5-methyl-1H-1-benzazepin-1-yl]methyl][1,1'-biphenyl]-2-carboxamide;

N-Ethyl-4'-[[3-[(3-amino-3-methyl-1-oxopropyl)-amino]-2,3,4,5-tetrahydro-2-oxo-4,5-dimethyl-1H-1-benzazepin-1-yl]methyl][1,1'-biphenyl]-2-carboxamide;

N-Ethyl-4'-[[3-[(3-amino-3-methyl-1-oxopropyl)-amino]-2,3,4,5-tetrahydro-2-oxo-4-(4-methoxyphenyl)-1H-1-benzazepin-1-yl]methyl][1,1'-biphenyl]-2-carboxamide;

N-Ethyl-4'-[[3-[[3-[2(R)-hydroxypropylamino]-3-methyl-1-oxobutyl]amino]-2,3,4,5-tetrahydro-2-oxo-4-methyl-1H-1-benzazepin-1-yl]methyl][1,1'-biphenyl]-2-carboxamide;

N-4'-[[3-[[3-[2(R)-Hydroxypropylamino]-3-methyl-1-oxobutyl]amino]-2,3,4,5-tetrahydro-2-oxo-5-phenyl-1H-1-benzazepin-1-yl]methyl][1,1'-biphenyl]-2-carboxamide;

N-4'-[[3-[[3-[2(R)-Hydroxypropylamino]-3-methyl-1-oxobutyl]amino]-7-fluoro-2,3,4,5-tetrahydro-2-oxo-5-methyl-1H-1-benzazepin-1-yl]methyl][1,1'-biphenyl]-2-carboxamide;

N-Ethyl-4'-[[3-[[3-[2(R)-hydroxypropylamino]-3-methyl-1-oxobutyl]amino]-2,3,4,5-tetrahydro-2-oxo-4,5-dimethyl-1H-1-benzazepin-1-yl]methyl]1,1'-biphenyl]-2-carboxamide;

N-Ethyl-4'-[[3-[(3-[3-[2(R)-hydroxypropylamino]-3-methyl-1-oxobutyl)amino]-2,3,4,5-tetrahydro-2-oxo-4-(4-methoxyphenyl)-1H-1-benzazepin-1-yl]-methyl]-[1,1'-biphenyl]-2-carboxamide;

4'-[[3-[(3-[3-[2(R)-Hydroxypropylamino]-3-methyl-1-oxobutyl)amino]-2,3,4,5-tetrahydro-2-oxo-5-phenylthio-1H-1-benzazepin-1-yl]-methyl]-[1,1'-biphenyl]-2-carboxamide;

N-Ethyl-4'-[[3-[(3-[2(S),3-dihydroxypropylamino]-3-methyl-1-oxobutyl)amino]-2,3,4,5-tetrahydro-2-oxo-4-methyl-1H-1-benzazepin-1-yl]-methyl]-[1,1'-biphenyl]-2-carboxamide;

4'-[[3-[(3-[2(S),3-Dihydroxypropylamino]-3-methyl-1-oxobutyl)amino]-2,3,4,5-tetrahydro-2-oxo-5-methyl-1H-1-benzazepin-1-yl]-methyl]-[1,1'-biphenyl]-2-carboxamide;

N-Ethyl-4'-[[3-[(3-[2(S),3-dihydroxypropylamino]--3-methyl-1-oxobutyl)amino]-2,3,4,5-tetrahydro-2-oxo-4-(4-methoxyphenyl)-1H-1-benzazepin-1-yl]methyl]-[1,1'-biphenyl]-2-carboxamide;

N-[1-[[2'-[(Methylaminocarbonyl)amino][1,1'-biphenyl]-4-yl]methyl]-2,3,4,5-tetrahydro-2-oxo-4-methyl-1H-1-benzazepin-3-yl]-3-amino-3-methylbutanamide;

N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-3-amino-3-methylbutanamide;

N-[1-[[2'-[(Morpholinocarbonyl)amino][1,1'-biphenyl]-4-yl]methyl]-2,3,4,5-tetrahydro-2-oxo-4-methyl-1H-1-benzazepin-3-yl]-3-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-4-methyl-1H-1-benzazepin-3-yl]-3-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-5-methyl-1H-1-benzazepin-3-yl]-3-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-4-(4-methoxyphenyl)-1H-1-benzazepin-3-yl]-3-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-5-phenyl-1H-1-benzazepin-3-yl]-3-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-4,5-dimethyl-1H-1-benzazepin-3-yl]-3-amino-3-methylbutanamide;

N-[1-[[2'-[(Methylaminocarbonyl)oxy][1,1'-biphenyl]-4-yl]methyl]-2,3,4,5-tetrahydro-2-oxo-5-methyl-1H-1-benzazepin-3-yl]-3-amino-3-methylbutanamide;

N-[1-[[2'-[2-[(Methylaminocarbonyl)amino]phenoxy]-1,1'-biphenyl]-4-yl]methyl]-2,3,4,5-tetrahydro-2-oxo-4-methyl-1H-1-benzazepin-3-yl]-3-amino-3-methylbutanamide;

N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-3-(2(R)-hydroxypropyl)amino-3-methylbutanamide;

N-[1-[[2'-[(Methylaminocarbonyl)amino][1,1'-biphenyl]-4-yl]methyl]-2,3,4,5-tetrahydro-2-oxo-5-methyl-1H-1-benzazepin-3-yl]-3-[2(S),3-dihydroxypropyl]-amino-3-methylbutanamide;

N-[1-[[2'-[(Morpholinocarbonyl)amino][1,1'-phenyl]-4-yl]methyl]-2,3,4,5-tetrahydro-2-oxo-5-methyl-1H-1-benzazepin-3-yl]-3-(2(R)-hydroxypropyl)amino-3-methylbutanamide;

N-[1-[[2'-[(Morpholinocarbonyl)amino][1,1'-phenyl]-4-yl]methyl]-2,3,4,5-tetrahydro-2-oxo-5-methyl-1H-1-benzazepin-3-yl]-3-[2(S),3-dihydroxypropyl]-amino-3-methylbutanamide;

N-[1-[[2'-[[(2-Hydroxyethylamino)carbonyl]amino]-[1,1'-biphenyl]-4-yl]methyl]-2,3,4,5-tetrahydro-2-oxo-5-methyl-1H-1-benzazepin-3-yl]-3-(2(R)-hydroxypropyl)amino-3-methylbutanamide;

N-[1-[[2'-[[(2-Hydroxyethylamino)carbonyl]amino]-[-1,1'-biphenyl]-4-yl]methyl]-2,3,4,5-tetrahydro-2-oxo-5-methyl-1H-1-benzazepin-3-yl]-3-[2(S),3-dihydroxypropyl]-amino-3-methylbutanamide;

N-[1-[[2'-[(Methylaminocarbonyl)amino][1,1'-biphenyl]-4-yl]methyl]-2,3,4,5-tetrahydro-2-oxo-5- methyl-1H-1-benzazepin-3-yl]-2-amino-2-methyl-propanamide;

N-[1-[[2'-[(Methylaminocarbonyl)amino][1,1'-biphenyl]-4-yl]methyl]-7-fluoro-2,3,4,5-tetrahydro-2-oxo-5-methyl-1H-1-benzazepin-3-yl]-2-amino-2-methylpropanamide;

N-[1-[[2'-[(Methylaminocarbonyl)amino][1,1'-biphenyl]-4-yl]methyl]-7-2,3,4,5-tetrahydro-2-oxo-5-phenyl-1H-1-benzazepin-3-yl]-2-amino-2-methyl-propanamide;

N-[1-[[2'-[(Methylaminocarbonyl)amino][1,1'-biphenyl]-4-yl]methyl]-7-2,3,4,5-tetrahydro-2-oxo-4-methyl-1H-1-benzazepin-3-yl]-2-amino-2-methyl-propanamide;

N-[1-[[2'-[(Morpholinocarbonyl)amino][1,1'-biphenyl]-4-yl]methyl]-2,3,4,5-tetrahydro-2-oxo-4-(4-methoxyphenyl)-1H-1-benzazepin-3-yl]-2-amino-2-methylpropanamide;

N-[1-[[2'-[[(2-Hydroxyethylamino)carbonyl]amino]-[1,1'-biphenyl]-4-yl]methyl]-2,3,4,5-tetrahydro-2-oxo-4-(4-methoxyphenyl)-1H-1-benzazepin-3-yl]-2-amino-2-methylpropanamide;

N-[1-[[2'-[(Methylaminocarbonyl)amino][1,1'-biphenyl]-4-yl]methyl]-7-fluoro-2,3,4,5-tetrahydro-2-oxo-4-methyl-1H-1-benzazepin-3-yl]-3-(2(R)-hydroxypropyl)amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-5-methyl-1H-1-benzazepin-3-yl]-3-(2(R)-hydroxypropyl)amino-3-methylbutanamide;

N-[1-[[2'-[(Methylaminocarbonyl)amino][1,1'-biphenyl]-4-yl]methyl]-7-fluoro-2,3,4,5-tetrahydro-2-oxo-4-phenyl-1H-1-benzazepin-3-yl]-3-[2(S)-dihydroxypropyl]amino-3-methylbutanamide;

N-[1-[[2'-[[(2-Hydroxyethylamino)carbonyl]amino]-[1,1'-biphenyl]-4-yl]methyl]-7-fluoro-2,3,4,5-tetrahydro-2-oxo-5-methyl-1H-1-benzazepin-3-yl]-3-(2(R)-hydroxypropyl)amino-3-methylbutanamide;

3-Amino-3-methyl-N-[2,3,4,5-tetrahydro-2-oxo-4-(4-methoxyphenyl)-1-[[2'-hydroxymethyl[1,1'-biphenyl]-4-yl]methyl]-1H-1-benzazepin-3-yl]-butanamide;

3-Amino-3-methyl-N-[2,3,4,5-tetrahydro-2-oxo-5-methyl-1-[[2'-hydroxymethyl[1,1'-biphenyl]-4-yl]-methyl]-1H-1-benzazepin-3-yl]-butanamide;

3-Amino-3-methyl-N-[2,3,4,5-tetrahydro-2-oxo-4-methyl-1-[[2'-hydroxymethyl[1,1'-biphenyl]-4-yl]-methyl]-1H-1-benzazepin-3-yl]-butanamide;

3-[2(R)-Hydroxypropyl]amino-3-methyl-N-[2,3,4,5-tetrahydro-2-oxo-5-methyl-1-[[2'-hydroxymethyl[1,1'-biphenyl]-4-yl]-methyl]-1H-1-benzazepin-3-yl]-butanamide;

2-Amino-2-methyl-N-[2,3,4,5-tetrahydro-2-oxo-5-methyl-1-[[2'-hydroxymethyl[1,1'-biphenyl]-4-yl]-methyl]-1H-1-benzazepin-3-yl]-butanamide;

3-Amino-3-methyl-N-[2,3-dihydro-2-oxo-5-methyl-1-[[2'-(1H-tetrazol-5-yl)[1,1'-biphenyl]-4-yl]methyl]-1H-1-benzazepin-3-yl]-butanamide;

3-Amino-3-methyl-N-[2,3-dihydro-2-oxo-4-(4-methoxyphenyl)-1-[[2'-(1H-tetrazol-5-yl)[1,1'-biphenyl]-4-yl]methyl]-1H-1-benzazepin-3-yl]-butanamide;

3-[2(R)-Hydroxypropyl]amino-3-methyl-N-[2,3-dihydro-2-oxo-5-methyl-1-[[2'-(1H-tetrazol-5-yl)-[1,1'-biphenyl]-4-yl]-methyl]-1H-1-benzazepin-3-yl]-butanamide;

2-Amino-2-methyl-N-[2,3-dihydro-2-oxo-5-methyl-1-[[2'-(1H-tetrazol-5-yl)[1,1'-biphenyl]-4-yl]methyl]-1H-1-benzazepin-3-yl]-propanamide;

N-Ethyl-4'-[[3-[(3-amino-3-methyl-1-oxobutyl)-amino]-2,3-dihydro-2-oxo-5-methyl-1H-1-benzazepin-1-yl]methyl][1,1'-biphenyl]-2-carboxamide;

N-[1-[[2'-[Methylaminocarbonyl)amino][1,1'-biphenyl]-4-yl]methyl]-2,3-dihydro-2-oxo-5-methyl-1H-1-benzazepin-3-yl]-3-amino-3-methylbutanamide;

N-[1-[[2'-[Methylaminocarbonyl)oxy][1,1'-biphenyl]-4-yl]methyl]-2,3-dihydro-2-oxo-5-methyl-1H-1-benzazepin-3-yl]-3-amino-3-methylbutanamide;

3-Amino-3-methyl-N-[2,3-dihydro-2-oxo-5-methyl-1-[[2'-hydroxymethyl[1,1'-biphenyl]-4-yl]methyl-1H-1-benzazepin-3-yl]-butanamide;

3-Amino-3-methyl-N-[2,3,4,5-tetrahydro-4-oxo-2-(4-methoxyphenyl)-5-[[2'-(1H-tetrazol-5-yl)[1,1'-biphenyl]-4-yl]methyl-5H-1,5-benzothiazepin-3-yl]-butanamide;

3-Amino-3-methyl-N-[2,3,4,5-tetrahydro-4-oxo-2-methyl-5-[[2'-(1H-tetrazol-5-yl)[1,1'-biphenyl]-4-yl]methyl-5H-1,5-benzothiazepin-3-yl]-butanamide;

2-Amino-3-methyl-N-[2,3,4,5-tetrahydro-4-oxo-2-methyl-5-[[2'-(1H-tetrazol-5-yl)[1,1'-biphenyl]-4-yl]methyl-5H-1,5-benzothiazepin-3-yl]-propanamide;

3-Amino-3-methyl-N-[2,3,4,5-tetrahydro-4-oxo-2-methyl-5-[[2'-hydroxymethyl[1,1'-biphenyl]-4-yl]-methyl-5H-1,5-benzothiazepin-3-yl]-butanamide;

N-Ethyl-4'-[[3-[(3-amino-3-methyl-1-oxobutyl)-amino]-2,3,4,5-tetrahydro-4-oxo-2-methyl-5H-5-benzothiazepin-5-yl]methyl][1,1'-biphenyl]-2-carboxamide;

4'-[[3-[(3-[2(S),3-Dihydroxypropylamino]-3-methyl-1-oxobutyl)amino]-2,3,4,5-tetrahydro-4-oxo-2-methyl-5H-5-benzothiazepin-5-yl]methyl][1,1'-biphenyl]-2-carboxamide;

N-[5-[[2'-[(Methylamino)carbonyl]amino][1,1'-biphenyl]-4-yl]methyl]-2,3,4,5-tetrahydro-2-methyl-4-oxo-5H-1,5-benzothiazepin-3-yl]-3-amino-3-methylbutanamide;

N-[5-[[2'-[(Hydroxyethylamino)carbonyl]amino][1,1'-biphenyl]-4-yl]methyl]-2,3,4,5-tetrahydro-4-oxo-1,5-benzothiazepin-3-yl]-3-amino-3-methylbutanamide;

N-[5-[[2'-[(Methylamino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide;

N-[5-[[2'-[(Morpholino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide;

N-[5-[[2'-[(Hydroxyethylamino)carbonyl]amino][1,1'-biphenyl]-4-yl]methyl]-2,3,4,5-tetrahydro-4-oxo-1,5-benzothiazepin-3-yl]-3-(2(R)-hydroxypropyl)amino-3-methylbutanamide;

N-[5-[[2'-[(Methylamino)carbonyl]amino][1,1'-biphenyl]-4-yl]methyl]-2,3,4,5-tetrahydro-4-oxo-1,5-benzothiazepin-3-yl]-3-(2(S),3-dihydroxypropyl]amino-3-methylbutanamide;

7. A method for increasing levels of endogenous growth hormone in a human or an animal which comprises administering to such human or animal an effective amount of a compound of claim 1.

8. A composition useful for increasing the endogenous production or release of growth hormone in a human or an animal which comprises an inert carrier and an effective amount of a compound of claim 1.

9. A composition useful for increasing the endogenous production/release of growth hormone in a human or an animal which comprises an inert carrier and an effective amount of a compound of claim 1 used in combination with other growth hormone secretagogues including GHRP-6 or GHRP-1, growth hormone releasing factor (GRF) or one of its analogs, IGF-1 or IGF-2, or B-HT920.

10. A method for the treatment of obesity which comprises administering to an obese patient a compound of claim 1 in combination with an $\alpha_2$ adrenergic agonist.

11. A composition for the treatment of obesity which comprises an inert carrier and a compound of claim 1 in combination with an $\alpha_2$ adrenergic agonist.

12. A method for the treatment of osteoporosis which comprises administering to a patient with osteoporosis a compound of claim 1 in combination with parathyroid hormone.

13. A composition for the treatment of osteoporosis which comprises an inert carrier and a compound of claim 1 in combination with parathyroid hormone.

* * * * *